United States Patent
Horne et al.

(10) Patent No.: US 12,173,000 B2
(45) Date of Patent: Dec. 24, 2024

(54) BERBAMINE DERIVATIVES AND METHODS OF USE THEREOF

(71) Applicant: CITY OF HOPE, Duarte, CA (US)

(72) Inventors: David Horne, Duarte, CA (US); Wendong Huang, Duarte, CA (US); Jun Xie, Duarte, CA (US); Binfeng Zhang, Duarte, CA (US); Senlin Xu, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 767 days.

(21) Appl. No.: 17/423,755

(22) PCT Filed: Jan. 17, 2020

(86) PCT No.: PCT/US2020/014148
§ 371 (c)(1),
(2) Date: Jul. 16, 2021

(87) PCT Pub. No.: WO2020/150638
PCT Pub. Date: Jul. 23, 2020

(65) Prior Publication Data
US 2022/0119389 A1    Apr. 21, 2022

Related U.S. Application Data

(60) Provisional application No. 62/794,361, filed on Jan. 18, 2019.

(51) Int. Cl.
*C07D 471/12* (2006.01)
*A61P 35/00* (2006.01)
*C07D 491/18* (2006.01)

(52) U.S. Cl.
CPC ............ *C07D 471/12* (2013.01); *A61P 35/00* (2018.01)

(58) Field of Classification Search
CPC ...... C07D 471/12; C07D 491/18; A61P 35/00
See application file for complete search history.

(56) References Cited

U.S. PATENT DOCUMENTS

| 2013/0178470 A1 | 7/2013 | Xu et al. |
| 2014/0155423 A1* | 6/2014 | Horne ..................... A61P 35/00 546/37 |
| 2014/0343047 A1 | 11/2014 | Xu et al. |
| 2018/0280379 A1 | 10/2018 | Menon et al. |

FOREIGN PATENT DOCUMENTS

| WO | WO-2017/066428 A1 | 4/2017 |
| WO | WO-2018/191171 A1 | 10/2018 |

OTHER PUBLICATIONS

Geng, L. et al. (Jul. 25, 2017). "GLI1 inhibitor GANT61 exhibits antitumor efficacy in T-cell lymphoma cells through down-regulation of p-STAT3 and SOCS3," *Oncotarget* 8(30):48701-48710.
Gu, Y. et al. (Dec. 6, 2012, e-published Oct. 16, 2012). "CaMKII γ, a critical regulator of CML stem/progenitor cells, is a target of the natural product berbamine," *Blood* 120(24):4829-4839.
International Search Report mailed on Mar. 19, 2020, for PCT Application No. PCT/US2020/014148, filed Jan. 17, 2020, 3 pages.
PubChem SID 103686689, CHEMBL554807 (Jun. 6, 2017). Located at <https://pubchem.ncbi.nlm.nih.gov/substance/103686689> 7 pages.
Written Opinion mailed on Mar. 19, 2020, for PCT Application No. PCT/US2020/014148, filed Jan. 17, 2020, 10 pages.

* cited by examiner

*Primary Examiner* — Sun Jae Yoo
(74) *Attorney, Agent, or Firm* — Mintz, Levin, Cohn, Ferris, Glovsky and Popeo, P.C.

(57) ABSTRACT

Provided herein are, inter alia, methods of treating cancer using compounds of the invention.

41 Claims, 8 Drawing Sheets

| Cell lines | IC50-BBM-24h(uM) | IC50-PA4-24h(uM) |
|---|---|---|
| NU-DHL1 | 25.36 | 2.88 |
| SU-DHL6 | 30.47 | 4.00 |
| LY19 | 38.68 | 3.29 |
| DOGKIT | 15.36 | 1.14 |
| VAL | 28.67 | 3.07 |

BERBAMINE DERIVATIVES AND METHODS OF USE THEREOF

CROSS REFERENCES TO RELATED APPLICATIONS

This application is the national stage filing under U.S.C. 371 of International Application No. PCT/US20/14148, filed on Jan. 17, 2020, which claims the benefit of priority of U.S. Provisional Application No. 62/794,361 filed on Jan. 18, 2019, which is incorporated herein by reference in its entirety and for all purposes.

BACKGROUND OF THE INVENTION

Berbamine is a natural product derived from the plant, *Berberis vulgaris*, which has been used previously in Asia and Europe for the treatment of various ailments. So far, only a handful of berbamine derivatives have been reported and no clinical use of berbamine in cancer treatments are available.

Therefore, there is a need to synthesize novel berbamine derivatives for potential therapeutic treatments, especially the cancer treatments. The present disclosure relates to new berbamine derivatives and pharmaceutical compositions thereof as well as a method of treating T-cell lymphoma and other cancers.

BRIEF SUMMARY OF THE INVENTION

Herein are provided, inter alia, a compound and a method of treating a cancer in a subject in need thereof. The method includes administering to the subject an effective amount of a compound or a salt (e.g. pharmaceutically acceptable salt) thereof as described herein.

In an aspect is provided a compound having a formula:

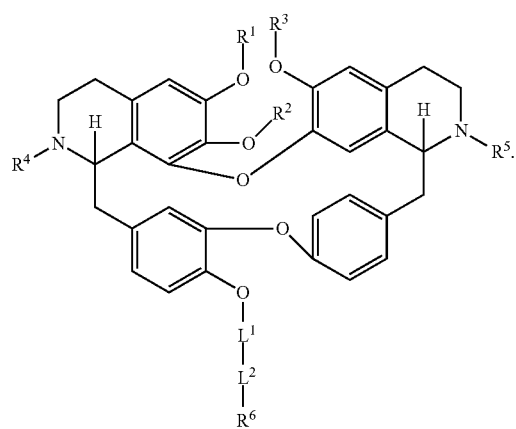

(I)

Each $R^1$, $R^2$, $R^3$, $R^4$, and $R^5$ is independently hydrogen, or substituted or unsubstituted $C_1$-$C_{10}$ alkyl.

$L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$L^2$ is —NR$^{2A}$S(O)$_2$— or —S(O)$_2$NR$^{2B}$—.

$R^6$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{2A}$ and $R^{2B}$ are independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

X is independently —F, —Cl, —Br or —I.

In an aspect is provided a pharmaceutical composition including a compound as described herein, and a pharmaceutically acceptable carrier thereof.

In an aspect is a method of treating cancer in a subject in need thereof, the method including administering to the subject an effective amount of a pharmaceutical composition including a compound, or a salt thereof, as described herein.

In an aspect is a method of treating cancer in a subject in need thereof, the method including administering to the subject an effective amount of a compound, or a salt thereof, as described herein.

BRIEF DESCRIPTION OF THE DRAWINGS

FIG. 2A shows that five DHL cell lines expressed phosphorylated CAMKII, phosphorylated c-Myc, c-Myc, Bcl2 and phosphorylated STAT3(s727) at different levels as shown by western blotting analysis. FIG. 2B shows that IC$_{50}$ of BBM and PA4 to five DHL cell lines were determined by MTS assay. FIGS. 2C-2D show that BBM and PA4 decreased cell viability in a dose-dependent manner. DHL cell lines were treated with BBM or PA4 at increasing concentrations as indicated. Cell viability were determined by MTS assay at 24 h and normalized to vehicle control.

DETAILED DESCRIPTION OF THE INVENTION

I. Definitions

Figure 1A:
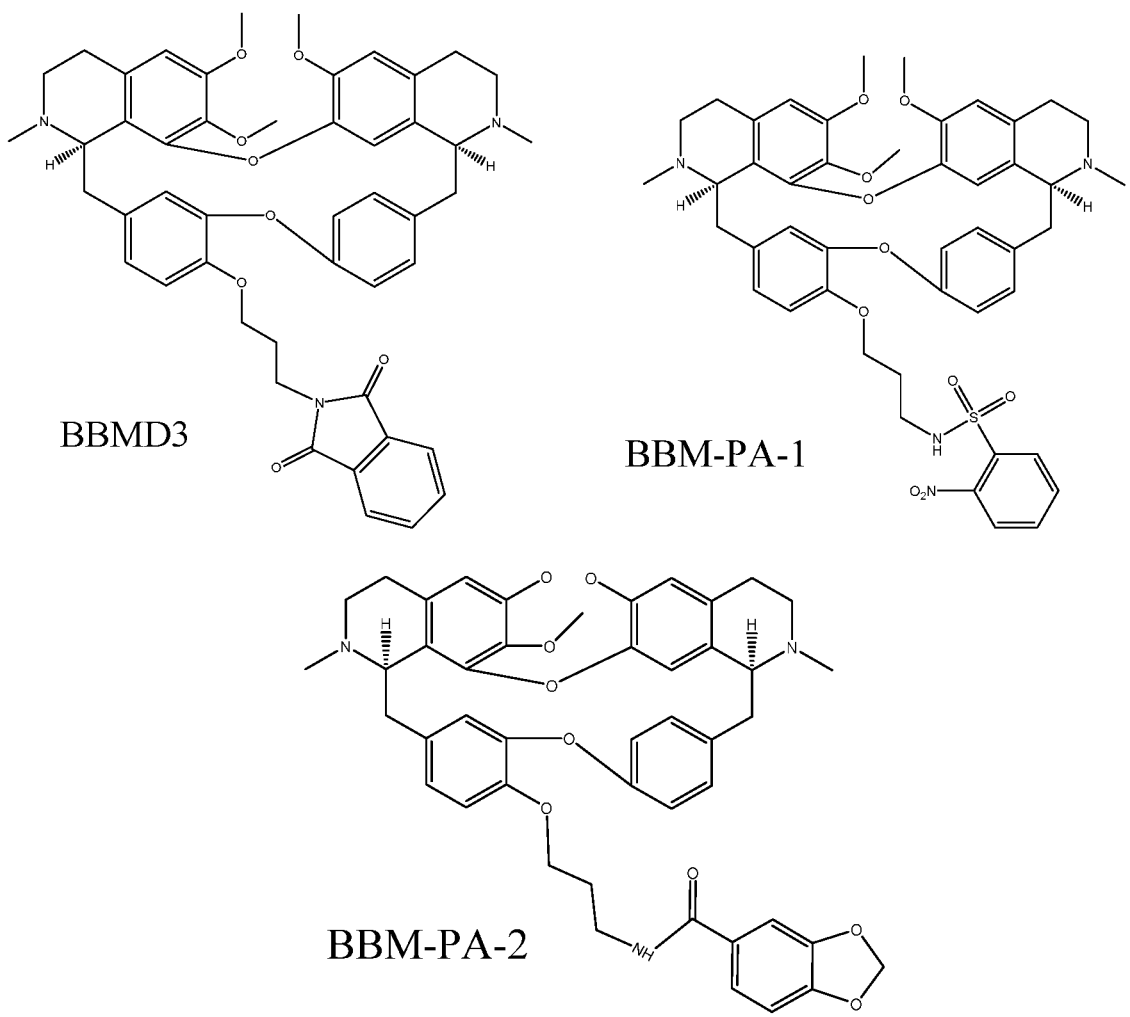
FIGS. 1A-1C show exemplary compounds of the invention and comparative compounds used in biological assay in Examples 2-3.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3 dioxanyl, 1,4 dioxanyl, 1,3 dioxolanyl, 1,3 dithiolanyl, 1,3 dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1 dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3 dihydrobenzofuran 2 yl, 2,3 dihydrobenzofuran 3 yl, indolin 1 yl, indolin 2 yl, indolin 3 yl, 2,3 dihydrobenzothien 2 yl, decahydroquinolinyl, decahydroisoquinolinyl, octahydro 1H indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring.

In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—O$CH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R'', —OR', —SR', and/or —SO₂R'. Where "heteroalkyl" is recited, followed by recitations of specific heteroalkyl groups, such as —NR'R'' or the like, it will be understood that the terms heteroalkyl and —NR'R'' are not redundant or mutually exclusive. Rather, the specific heteroalkyl groups are recited to add clarity. Thus, the term "heteroalkyl" should not be interpreted herein as excluding specific heteroalkyl groups, such as —NR'R'' or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C₁-C₄)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a poly-unsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "⁓" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

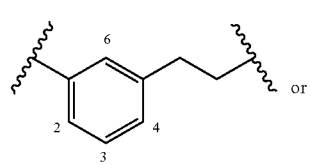

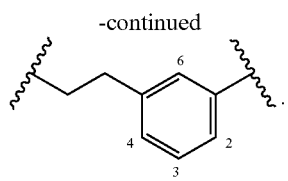

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'—$(C''R''R''')_d$—, where s and d are independently integers of from 0 to 3, and X' is —O—, —NR'—, —S—, —S(O)—, —$S(O)_2$—, or —$S(O)_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_3$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments of the compounds herein, each substituted or unsubstituted alkyl may be a substituted (e.g., substituted with a substituent group, a size-limited substituent group, or lower substituent group) or unsubstituted $C_1$-$C_{20}$ alkyl, each substituted or unsubstituted heteroalkyl is a substituted (e.g., substituted with a substituent group, a size-limited substituent group, or lower substituent group) or unsubstituted 2 to 20 membered heteroalkyl, each substituted or unsubstituted cycloalkyl is a substituted (e.g., substituted with a substituent group, a size-limited substituent group, or lower substituent group) or unsubstituted $C_3$-$C_8$ cycloalkyl, each substituted or unsubstituted heterocycloalkyl is a substituted (e.g., substituted with a substituent group, a size-limited substituent group, or lower substituent group) or unsubstituted 3 to 8 membered heterocycloalkyl, each or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 10 membered heteroaryl. In embodiments herein, each substituted or unsubstituted alkylene is a substituted (e.g., substituted with a substituent group, a size-limited substituent group, or lower substituent group) or unsubstituted $C_1$-$C_{20}$ alkylene, each substituted or unsubstituted heteroalkylene is a substituted (e.g., substituted with a substituent group, a size-limited substituent group, or lower substituent group) or unsubstituted 2 to 20 membered heteroalkylene, each substituted or unsubstituted cycloalkylene is a substituted (e.g., substituted with a substituent group, a size-limited substituent group, or lower substituent group) or unsubstituted $C_3$-$C_3$ cycloalkylene, each substituted or unsubstituted heterocycloalkylene is a substituted (e.g., substituted with a substituent group, a size-limited substituent group, or lower substituent group) or unsubstituted 3 to 8 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 10 membered heteroarylene.

In some embodiments, each substituted or unsubstituted alkyl is a substituted (e.g., substituted with a substituent group, a size-limited substituent group, or lower substituent group) or unsubstituted $C_1$-$C_8$ alkyl, each substituted or unsubstituted heteroalkyl is a substituted (e.g., substituted with a substituent group, a size-limited substituent group, or lower substituent group) or unsubstituted 2 to 8 membered heteroalkyl, each substituted or unsubstituted cycloalkyl is a substituted (e.g., substituted with a substituent group, a size-limited substituent group, or lower substituent group) or unsubstituted $C_3$-$C_7$ cycloalkyl, each substituted or unsubstituted heterocycloalkyl is a substituted (e.g., substituted with a substituent group, a size-limited substituent group, or lower substituent group) or unsubstituted 3 to 7 membered heterocycloalkyl, each substituted or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 9 membered heteroaryl. In some embodiments, each substituted or unsubstituted alkylene is a substituted (e.g., substituted with a substituent group, a size-limited substituent group, or lower substituent group) or unsubstituted $C_1$-$C_8$ alkylene, each substituted or unsubstituted heteroalkylene is a substituted (e.g., substituted with a substituent group, a size-limited substituent group, or lower substituent group) or unsubstituted 2 to 8 membered heteroalkylene, each substituted or unsubstituted cycloalkylene is a substituted (e.g., substituted with a substituent group, a size-limited substituent group, or lower substituent group) or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby including another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently. The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As defined herein, a term "$Ca^{2+}$/calmodulin-dependent protein kinase" or "CAMK" refers to an enzyme that is activated by increases in the concentration of intracellular calcium ions ($Ca^{2+}$) and transfers phosphates from ATP to defined serine or threonine residues in other proteins. Activated CAMK is also involved in the phosphorylation of transcription factors and therefore, in the regulation of expression of responding genes. Family of this enzyme class include: calcium/calmodulin-dependent protein kinase type I (CAMKI; e.g., UniPro ID: Q14012); calcium/calmodulin-dependent protein kinase type II (CAMKII); calcium/calmodulin-dependent protein kinase type III (CAMKIII; e.g., UniPro ID: Q9ZUZ2); and calcium/calmodulin-dependent protein kinase type IV (CAMKIV; e.g., UniPro ID: Q16566). CAMKI (e.g., UniPro ID: Q14012) may have isoforms of CAMKIα, CAMKIβ, CAMKIδ (e.g., UniPro ID: Q8IU85), and CAMKIγ (e.g., UniPro ID: Q96NX5); and CAMKII may have isoforms of CAMKIIα (e.g., UniPro ID: Q9UQM7), CAMKIIβ (e.g., UniPro ID: Q13554), CAMKIIδ (e.g., UniPro ID: Q13557), CAMKIIγ (e.g., UniPro ID: Q13555). For instance, CAMKIIγ functions autonomously after $Ca^{2+}$/calmodulin-binding and autophosphorylation, and is involved in sarcoplasmic reticulum $Ca^{2+}$ transport in skeletal muscle. In addition, CAMKIIγ may function in dendritic spine and synapse formation and neuronal plasticity. In slow-twitch muscles, is involved in regulation of sarcoplasmic reticulum (SR) $Ca^{2+}$ transport and in fast-twitch muscle participates in the control of $Ca^{2+}$ release from the SR through phosphorylation of the ryanodine receptor-coupling factor triadin. In neurons, this enzyme may participate in the promotion of dendritic spine and synapse formation and maintenance of synaptic plasticity which enables long-term potentiation (LTP) and hippocampus-dependent learning.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). The term "inhibitor" may include synthetic or biological molecule (e.g. small molecule, nucleic acid, peptide or antibody) inhibiting or negatively affecting (e.g. decreasing) the activity or function of the protein relative to the activity or function of the protein in the absence of the inhibitor. In embodiments, the inhibitor is a small molecule.

The term "small molecule" or the like as used herein refers, unless indicated otherwise, to a molecule having a molecular weight of less than about 700 Dalton, e.g., less than about 700, 650, 600, 550, 500, 450, 400, 350, 300, 250, 200, 100, or even 50 Dalton.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

The term "prevent" refers to a decrease in the occurrence of disease (e.g., $Ca^{2+}$/calmodulin-dependent protein kinase (e.g., CAMK, CAMKII (e.g., CAMKIIα, CAMKIIβ, CAMKIIδ, or CAMKIIγ), or CAMKIIγ) associated disease) symptoms in a patient. As indicated above, the prevention may be complete (no detectable symptoms) or partial, such that fewer symptoms are observed than would likely occur absent treatment.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a catabolic enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may also include allowing two species to react, interact, or physically touch, wherein the two species may be a compound as described herein and a protein or enzyme. Contacting may include allowing a compound described herein to interact with a protein or enzyme that is involved in a catabolism.

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be cystic fibrosis transmembrane conductance regulator. Thus, activation includes, at least in part, partially or totally increasing stimulation, increasing, promoting, or expediting activation, or activating, sensitizing, or up-regulating signal transduction or enzymatic activity or the amount of a protein.

The term "modulate" is used in accordance with its plain ordinary meaning and refers to the act of changing or varying one or more properties. "Modulation" refers to the process of changing or varying one or more properties. For example, as applied to the effects of a modulator on a target protein (e.g., CAMKII (e.g., CAMKIIα, CAMKIIβ, CAMKIIδ, or CAMKIIγ), or CAMKIIγ), to modulate means to change by increasing or decreasing a property or function (e.g., activity or catabolic activity) of the target molecule or the amount of the target molecule.

The term "modulate" also refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. cancer) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anticancer or antitumor agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anticancer or antitumor agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cancer (e.g., breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia).

As used herein, the term "cancer" refers to all types of cancer, neoplasm, or malignant tumors found in mammals, including leukemia, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, uterine cancer, urinary bladder cancer, bladder cancer, esophagus cancer, gastric cancer, head and neck cancer, cholangiocarcinoma, mesothelioma, premalignant skin lesions, testicular cancer, lymphomas, thyroid cancer, neuroblastoma, esophageal cancer, genitourinary tract cancer, malignant hypercalcemia, endometrial cancer, adrenal cortical cancer, fallopian tube cancer, neoplasms of the endocrine and exocrine pancreas cancer, prostate cancer, breast cancer including triple negative breast cancer, and cutaneous T-cell lymphoma.

The term "lymphoma" refers to a group of blood cell tumors that develop from cells of the immune system found in lymph, i.e. lymphocytes (e.g. natural killer cells (NK cells), T cells, and B cells). Lymphoma is typically classified into Hodgkin's lymphomas (HL) and the non-Hodgkin lymphomas (NHL) or based on whether it develops in B-lymphocytes (B-cells) or T-lymphocytes (T-cells). In embodiments, lymphoma is developed in B-cells. In embodiments, lymphoma is developed in T-cell. In embodiments, lymphoma is double-hit lymphoma (DHL).

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, largecell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In embodiments, anticancer agents herein may include epigenetic inhibitors and multi- or specific kinase inhibitors.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDE), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

As used herein, the term "inflammatory disease" refers to a disease or condition characterized by aberrant inflammation (e.g. an increased level of inflammation compared to a control such as a healthy person not suffering from a disease). Examples of inflammatory diseases include traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, and atopic dermatitis.

The term "infection" or "infectious disease" refers to a disease or condition that can be caused by organisms such as a bacterium, virus, fungi or any other pathogenic microbial agents. In embodiments, the infectious disease is caused by a pathogenic bacteria. Pathogenic bacteria are bacteria which cause diseases (e.g., in humans). In embodiments, the infectious disease is a bacteria associated disease (e.g., tuberculosis, which is caused by *Mycobacterium tuberculosis*). Non-limiting bacteria associated diseases include pneumonia, which may be caused by bacteria such as *Streptococcus* and *Pseudomonas*; or foodborne illnesses, which can be caused by bacteria such as *Shigella, Campylobacter*, and *Salmonella*. Bacteria associated diseases also includes tetanus, typhoid fever, diphtheria, syphilis, and leprosy. In embodiments, the disease is Bacterial vaginosis (i.e. bacteria that change the vaginal microbiota caused by an overgrowth of bacteria that crowd out the Lactobacilli species that maintain healthy vaginal microbial populations) (e.g., yeast infection, or *Trichomonas vaginalis*); Bacterial meningitis (i.e. a bacterial inflammation of the meninges); Bacterial pneumonia (i.e. a bacterial infection of the lungs); Urinary tract infection; Bacterial gastroenteritis; or Bacterial skin infections (e.g. impetigo, or cellulitis). In embodiments, the infectious disease is a *Campylobacter jejuni, Enterococcus faecalis, Haemophilus influenzae, Helicobacter pylori, Klebsiella pneumoniae, Legionella pneumophila, Neisseria gonorrhoeae, Neisseria meningitides, Staphylococcus aureus, Streptococcus pneumonia*, or *Vibrio cholera* infection.

The term "associated" or "associated with" in the context of a substance or substance activity or function associated with a disease (e.g. a protein associated disease, a cancer associated with CAMK, CAMKII (e.g., CAMKIIα, CAMKIIβ, CAMKIIδ, or CAMKIIγ), or CAMKIIγ activity, CAMK, CAMKII (e.g., CAMKIIα, CAMKIIβ, CAMKIIδ, or CAMKIIγ), or CAMKIIγ associated cancer, CAMK, CAMKII (e.g., CAMKIIα, CAMKIIβ, CAMKIIδ, or CAMKIIγ), or CAMKIIγ associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with CAMK, CAMKII (e.g., CAMKIIα, CAMKIIβ, CAMKIIδ, or CAMKIIγ), or CAMKIIγ activity or function may be a cancer that results (entirely or partially) from aberrant CAMK, CAMKII (e.g., CAMKIIα, CAMKIIβ, CAMKIIδ, or CAMKIIγ), or CAMKIIγ function (e.g. catabolic enzyme activity, protein-protein interaction, signaling pathway) or a cancer wherein a particular symptom of the disease is caused (entirely or partially) by aberrant CAMK, CAMKII (e.g., CAMKIIα, CAMKIIβ, CAMKIIδ, or CAMKIIγ), or CAMKIIγ activity or function. As used herein, what is described as being associated with a disease, if a causative agent, could be a target for treatment of the disease. For example, a cancer associated with CAMK, CAMKII (e.g., CAMKIIα, CAMKIIβ, CAMKIIδ, or CAMKIIγ), or CAMKIIγ activity or function or a CAMK, CAMKII (e.g., CAMKIIα, CAMKIIβ, CAMKIIδ, or CAMKIIγ), or CAMKIIγ associated disease (e.g., cancer, inflammatory disease, autoimmune disease, or infectious disease), may be treated with a CAMK, CAMKII (e.g., CAMKIIα, CAMKIIβ, CAMKIIδ, or CAMKIIγ), or CAMKIIγ modulator or CAMK, CAMKII (e.g., CAMKIIα, CAMKIIβ, CAMKIIδ, or CAMKIIγ), or CAMKIIγ inhibitor, in the instance where increased CAMK, CAMKII (e.g., CAMKIIα, CAMKIIβ, CAMKIIδ, or CAMKIIγ), or CAMKIIγ activity or function (e.g. enzyme activity such as regulating phosphorylation) causes the disease (e.g., cancer, inflammatory disease, autoimmune disease, or infectious disease). For example, an inflammatory disease associated with CAMK, CAMKII (e.g., CAMKIIα, CAMKIIβ, CAMKIIδ, or CAMKIIγ), or CAMKIIγ activity or function or a CAMK, CAMKII (e.g., CAMKIIα, CAMKIIβ, CAMKIIδ, or CAMKIIγ), or CAMKIIγ associated inflammatory disease, may be treated with a CAMK, CAMKII (e.g., CAMKIIα, CAMKIIβ, CAMKIIδ, or CAMKIIγ), or CAMKIIγ modulator or CAMK, CAMKII (e.g., CAMKIIα, CAMKIIβ, CAMKIIδ, or CAMKIIγ), or CAMKIIγ inhibitor, in the instance where increased CAMK, CAMKII (e.g., CAMKIIα, CAMKIIβ, CAMKIIδ, or CAMKIIγ), or CAMKIIγ activity or function (e.g. regulating phosphorylation) causes the disease.

"Disease" or "condition" refer to a state of being or health status of a patient or subject capable of being treated with the compounds or methods provided herein. In certain embodiments, disease as used herein may refer to cancer (e.g. breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia).

II. Compounds

Provided herein are compounds having a structure of Formula (I):

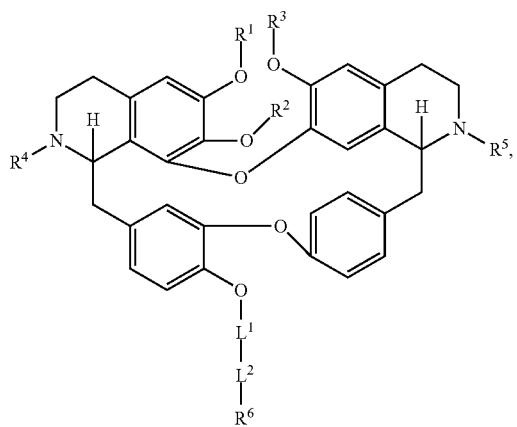

or a salt (e.g. pharmaceutically acceptable salt) thereof.

Each $R^1$, $R^2$, $R^3$, $R^4$, and $R^5$ is independently hydrogen, or substituted or unsubstituted $C_1$-$C_{10}$ alkyl.

$L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$L^2$ is —$NR^{2A}S(O)_2$— or —$S(O)_2NR^{2B}$—. In embodiments, $L^2$ is —$NR^{2A}S(O)_2$—. In embodiments, $L^2$ is —$S(O)_2 NR^{2B}$—.

$R^{2A}$ and $R^{2B}$ are independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is independently —F, —Cl, —Br or —I.

$R^6$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, $R^1$ is independently unsubstituted $C_1$-$C_{10}$ alkyl. In embodiments, $R^1$ is independently unsubstituted $C_1$-$C_8$ alkyl. In embodiments, $R^1$ is independently unsubstituted $C_1$-$C_6$ alkyl. In embodiments, $R^1$ is independently unsubstituted $C_1$-$C_5$ alkyl. In embodiments, $R^1$ is independently unsubstituted $C_1$-$C_4$ alkyl. In embodiments, $R^1$ is independently unsubstituted $C_1$-$C_3$ alkyl. In embodiments, $R^1$ is independently unsubstituted $C_1$-$C_2$ alkyl. In embodiments, $R^1$ is independently unsubstituted ethyl. In embodiments, $R^1$ is independently unsubstituted methyl. In embodiments, $R^1$ is hydrogen.

In embodiments, $R^2$ is independently unsubstituted $C_1$-$C_{10}$ alkyl. In embodiments, $R^2$ is independently unsubstituted $C_1$-$C_8$ alkyl. In embodiments, $R^2$ is independently unsubstituted $C_1$-$C_6$ alkyl. In embodiments, $R^2$ is independently unsubstituted $C_1$-$C_5$ alkyl. In embodiments, $R^2$ is independently unsubstituted $C_1$-$C_4$ alkyl. In embodiments, $R^2$ is independently unsubstituted $C_1$-$C_3$ alkyl. In embodiments, $R^2$ is independently unsubstituted $C_1$-$C_2$ alkyl. In embodiments, $R^2$ is independently unsubstituted ethyl. In embodiments, $R^2$ is independently unsubstituted methyl. In embodiments, $R^2$ is hydrogen.

In embodiments, $R^3$ is independently unsubstituted $C_1$-$C_{10}$ alkyl. In embodiments, $R^3$ is independently unsubstituted $C_1$-$C_8$ alkyl. In embodiments, $R^3$ is independently unsubstituted $C_1$-$C_6$ alkyl. In embodiments, $R^3$ is independently unsubstituted $C_1$-$C_5$ alkyl. In embodiments, $R^3$ is independently unsubstituted $C_1$-$C_4$ alkyl. In embodiments, $R^3$ is independently unsubstituted $C_1$-$C_3$ alkyl. In embodiments, $R^3$ is independently unsubstituted $C_1$-$C_2$ alkyl. In embodiments, $R^3$ is independently unsubstituted ethyl. In embodiments, $R^3$ is independently unsubstituted methyl. In embodiments, $R^3$ is hydrogen.

In embodiments, $R^4$ is independently unsubstituted $C_1$-$C_{10}$ alkyl. In embodiments, $R^4$ is independently unsubstituted $C_1$-$C_8$ alkyl. In embodiments, $R^4$ is independently unsubstituted $C_1$-$C_6$ alkyl. In embodiments, $R^4$ is independently unsubstituted $C_1$-$C_5$ alkyl. In embodiments, $R^4$ is independently unsubstituted $C_1$-$C_4$ alkyl. In embodiments, $R^4$ is independently unsubstituted $C_1$-$C_3$ alkyl. In embodiments, $R^4$ is independently unsubstituted $C_1$-$C_2$ alkyl. In embodiments, $R^4$ is independently unsubstituted ethyl. In embodiments, $R^4$ is independently unsubstituted methyl. In embodiments, $R^4$ is hydrogen.

In embodiments, $R^5$ is independently unsubstituted $C_1$-$C_{10}$ alkyl. In embodiments, $R^5$ is independently unsubstituted $C_1$-$C_8$ alkyl. In embodiments, $R^5$ is independently unsubstituted $C_1$-$C_6$ alkyl. In embodiments, $R^5$ is independently unsubstituted $C_1$-$C_5$ alkyl. In embodiments, $R^5$ is independently unsubstituted $C_1$-$C_4$ alkyl. In embodiments, $R^5$ is independently unsubstituted $C_1$-$C_3$ alkyl. In embodiments, $R^5$ is independently unsubstituted $C_1$-$C_2$ alkyl. In embodiments, $R^5$ is independently unsubstituted ethyl. In embodiments, $R^5$ is independently unsubstituted methyl. In embodiments, $R^5$ is hydrogen.

In embodiments, $R^6$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^6$ is substituted or unsubstituted $C_1$-$C_{20}$ alkyl. In embodiments, $R^6$ is substituted $C_1$-$C_{20}$ alkyl. In embodiments, $R^6$ is unsubstituted $C_1$-$C_{20}$ alkyl. In embodiments, $R^6$ is substituted or unsubstituted $C_1$-$C_{12}$ alkyl. In embodiments, $R^6$ is substituted $C_1$-$C_{12}$ alkyl. In embodiments, $R^6$ is unsubstituted $C_1$-$C_{12}$ alkyl. In embodiments, $R^6$ is substituted or unsubstituted $C_1$-$C_8$ alkyl. In embodiments, $R^6$ is substituted $C_1$-$C_8$ alkyl. In embodiments, $R^6$ is unsubstituted $C_1$-$C_8$ alkyl. In embodiments, $R^6$ is substituted or unsubstituted $C_1$-$C_6$ alkyl. In embodiments, $R^6$ is substituted $C_1$-$C_6$ alkyl. In embodiments, $R^6$ is unsubstituted $C_1$-$C_6$ alkyl. In embodiments, $R^6$ is substituted or unsubstituted $C_1$-$C_4$ alkyl. In embodiments, $R^6$ is substituted $C_1$-$C_4$ alkyl. In embodiments, $R^6$ is unsubstituted $C_1$-$C_4$ alkyl. In embodiments, $R^6$ is substituted or unsubstituted $C_1$-$C_2$ alkyl. In embodiments, $R^6$ is substituted $C_1$-$C_2$ alkyl. In embodiments, $R^6$ is unsubstituted $C_1$-$C_2$ alkyl.

In embodiments, $R^6$ is substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered). In embodiments, $R^6$ is substituted heteroalkyl (e.g., 2 to 20 membered, 2 to 12 membered, 2 to 8 membered, 2 to 6 membered, 4 to 6 membered, 2 to 3 membered, or 4 to 5 membered). In embodiments, $R^6$ is unsubstituted heteroalkyl (e.g., 2 to 20 membered, 2 to 12 membered, 2 to 8 membered, 2 to 6 membered, 4 to 6 membered, 2 to 3 membered, or 4 to 5 membered). In embodiments, $R^6$ is substituted or unsubstituted 2 to 20 membered heteroalkyl. In embodiments, $R^6$ is substituted 2 to 20 membered heteroalkyl. In embodiments, $R^6$ is unsubstituted 2 to 20 membered heteroalkyl. In embodiments, $R^6$ is substituted or unsubstituted 2 to 12 membered heteroalkyl. In embodiments, $R^6$ is substituted 2 to 12 membered heteroalkyl. In embodiments, $R^6$ is unsubstituted 2 to 12 membered heteroalkyl. In embodiments, $R^6$ is substituted or unsubstituted 2 to 8 membered heteroalkyl. In embodiments, $R^6$ is substituted 2 to 8 membered heteroalkyl. In embodiments, $R^6$ is unsubstituted 2 to 8 membered heteroalkyl. In embodiments, $R^6$ is substituted or unsubstituted 2 to 6 membered heteroalkyl. In embodiments, $R^6$ is substituted 2 to 6 membered heteroalkyl. In embodiments, $R^6$ is unsubstituted 2 to 6 membered heteroalkyl. In embodiments, $R^6$ is substituted or unsubstituted 4 to 6 membered heteroalkyl. In embodiments, $R^6$ is substituted 4 to 6 membered heteroalkyl. In embodiments, $R^6$ is unsubstituted 4 to 6 membered heteroalkyl. In embodiments, $R^6$ is substituted or unsubstituted 2 to 3 membered heteroalkyl. In embodiments, $R^6$ is substituted 2 to 3 membered heteroalkyl. In embodiments, $R^6$ is unsubstituted 2 to 3 membered heteroalkyl. In embodiments, $R^6$ is substituted or unsubstituted 4 to 5 membered heteroalkyl. In embodiments, $R^6$ is substituted 4 to 5 membered heteroalkyl. In embodiments, $R^6$ is unsubstituted 4 to 5 membered heteroalkyl.

In embodiments, $R^6$ is substituted or unsubstituted cycloalkyl (e.g., $C_3$-$C_{10}$, $C_3$-$C_8$, $C_3$-$C_6$, $C_4$-$C_6$, or $C_5$-$C_6$). In embodiments, $R^6$ is substituted cycloalkyl (e.g., $C_3$-$C_{10}$, $C_3$-$C_8$, $C_3$-$C_6$, $C_4$-$C_6$, or $C_5$-$C_6$). In embodiments, $R^6$ is unsubstituted cycloalkyl (e.g., $C_3$-$C_{10}$, $C_3$-$C_8$, $C_3$-$C_6$, $C_4$-$C_6$, or $C_5$-$C_6$). In embodiments, $R^6$ is substituted or unsubstituted $C_3$-$C_{10}$ cycloalkyl. In embodiments, $R^6$ is substituted $C_3$-$C_{10}$ cycloalkyl. In embodiments, $R^6$ is unsubstituted $C_3$-$C_{10}$ cycloalkyl. In embodiments, $R^6$ is substituted or unsubstituted $C_3$-$C_8$ cycloalkyl. In embodiments, $R^6$ is substituted $C_3$-$C_8$ cycloalkyl. In embodiments, $R^6$ is unsubstituted $C_3$-$C_8$ cycloalkyl. In embodiments, $R^6$ is substituted or unsubstituted $C_3$-$C_6$ cycloalkyl. In embodiments, $R^6$ is substituted $C_3$-$C_6$ cycloalkyl. In embodiments, $R^6$ is unsubstituted $C_3$-$C_6$ cycloalkyl. In embodiments, $R^6$ is substituted or unsubstituted $C_3$-$C_6$ cycloalkyl. In embodiments, $R^6$ is substituted $C_3$-$C_6$ cycloalkyl. In embodiments, $R^6$ is unsubstituted $C_3$-$C_6$ cycloalkyl. In embodiments, $R^6$ is substituted or unsubstituted $C_5$-$C_6$ cycloalkyl. In embodiments, $R^6$ is substituted $C_5$-$C_6$ cycloalkyl. In embodiments, $R^6$ is unsubstituted $C_5$-$C_6$ cycloalkyl. In embodiments, $R^6$ is substituted or unsubstituted cyclopropyl. In embodiments, $R^6$ is substituted cyclopropyl. In embodiments, $R^6$ is unsubstituted cyclopropyl. In embodiments, $R^6$ is substituted or unsubstituted cyclobutyl. In embodiments, $R^6$ is substituted cyclobutyl. In embodiments, $R^6$ is unsubstituted cyclobutyl. In embodiments, $R^6$ is substituted or unsubstituted cyclopentyl. In embodiments, $R^6$ is substituted cyclopentyl. In embodiments, $R^6$ is unsubstituted cyclopentyl. In embodiments, $R^6$ is substituted or unsubstituted cyclohexyl. In embodiments, $R^6$ is substituted cyclohexyl. In embodiments, $R^6$ is unsubstituted cyclohexyl. In embodiments, $R^6$ is substituted or unsubstituted cycloheptyl. In embodiments, $R^6$ is substituted cycloheptyl. In embodiments, $R^6$ is unsubstituted cycloheptyl. In embodiments, $R^6$ is substituted or unsubstituted cyclooctyl. In embodiments, $R^6$ is substituted cyclooctyl. In embodiments, $R^6$ is unsubstituted cyclooctyl.

In embodiments, $R^6$ is substituted or unsubstituted heterocycloalkyl (e.g., 3 to 10 membered, 3 to 8 membered, 3 to 6 membered, 4 to 6 membered, 4 to 5 membered, or 5 to 6 membered). In embodiments, $R^6$ is substituted heterocycloalkyl (e.g., 3 to 10 membered, 3 to 8 membered, 3 to 6 membered, 4 to 6 membered, 4 to 5 membered, or 5 to 6 membered). In embodiments, $R^6$ is unsubstituted heterocycloalkyl (e.g., 3 to 10 membered, 3 to 8 membered, 3 to 6 membered, 4 to 6 membered, 4 to 5 membered, or 5 to 6 membered). In embodiments, $R^6$ is substituted or unsubstituted 3 to 10 membered heterocycloalkyl. In embodiments, $R^6$ is substituted 3 to 10 membered heterocycloalkyl. In embodiments, $R^6$ is unsubstituted 3 to 10 membered heterocycloalkyl. In embodiments, $R^6$ is substituted or unsubstituted 3 to 8 membered heterocycloalkyl. In embodiments, $R^6$ is substituted 3 to 8 membered heterocycloalkyl. In embodiments, $R^6$ is unsubstituted 3 to 8 membered heterocycloalkyl. In embodiments, $R^6$ is substituted or unsubstituted 3 to 6 membered heterocycloalkyl. In embodiments, $R^6$ is substituted 3 to 6 membered heterocycloalkyl. In embodiments, $R^6$ is unsubstituted 3 to 6 membered heterocycloalkyl. In embodiments, $R^6$ is substituted or unsubstituted 4 to 6 membered heterocycloalkyl. In embodiments, $R^6$ is substituted 4 to 6 membered heterocycloalkyl. In embodiments, $R^6$ is unsubstituted 4 to 6 membered heterocycloalkyl. In embodiments, $R^6$ is substituted or unsubstituted 4 to 5 membered heterocycloalkyl. In embodiments, $R^6$ is substituted 4 to 5 membered heterocycloalkyl. In embodiments, $R^6$ is unsubstituted 4 to 5 membered heterocycloalkyl. In embodiments, $R^6$ is substituted or unsubstituted 5 to 6 membered heterocycloalkyl. In embodiments, $R^6$ is substituted 5 to 6 membered heterocycloalkyl. In embodiments, $R^6$ is unsubstituted 5 to 6 membered heterocycloalkyl. In embodiments, $R^6$ is substituted or unsubstituted morpholinyl. In embodiments, $R^6$ is substituted morpholinyl. In embodiments, $R^6$ is unsubstituted morpholinyl. In embodiments, $R^6$ is substituted or unsubstituted oxazolidinyl. In embodiments, $R^6$ is substituted oxazolidinyl. In embodiments, $R^6$ is unsubstituted oxazolidinyl. In embodiments, $R^6$ is substituted or unsubstituted piperazinyl. In embodiments, $R^6$ is substituted piperazinyl. In embodiments, $R^6$ is unsubstituted piperazinyl.

In embodiments, $R^6$ is substituted or unsubstituted piperidinyl. In embodiments, $R^6$ is substituted piperidinyl. In embodiments, $R^6$ is unsubstituted piperazinyl. In embodiments, $R^6$ is substituted or unsubstituted pyrrolidinyl. In embodiments, $R^6$ is substituted pyrrolidinyl. In embodiments, $R^6$ is unsubstituted pyrrolidinyl. In embodiments, $R^6$ is substituted or unsubstituted aryl (e.g., $C_6$-$C_{12}$, $C_6$-$C_{10}$, or phenyl). In embodiments, $R^6$ is substituted aryl (e.g., $C_6$-$C_{12}$, $C_6$-$C_{10}$, or phenyl). In embodiments, $R^6$ is unsubstituted aryl (e.g., $C_6$-$C_{12}$, $C_6$-$C_{10}$, or phenyl). In embodiments, $R^6$ is substituted or unsubstituted $C_6$-$C_{12}$ aryl. In embodiments, $R^6$ is substituted $C_6$-$C_{12}$ aryl. In embodiments, $R^6$ is unsubstituted $C_6$-$C_{12}$ aryl. In embodiments, $R^6$ is substituted or unsubstituted $C_6$-$C_{10}$ aryl. In embodiments, $R^6$ is substituted $C_6$-$C_{10}$ aryl. In embodiments, $R^6$ is unsubstituted $C_6$-$C_{10}$ aryl. In embodiments, $R^6$ is substituted or unsubstituted phenyl. In embodiments, $R^6$ is substituted phenyl. In embodiments, $R^6$ is unsubstituted phenyl. In embodiments, $R^6$ is substituted or unsubstituted naphthyl. In embodiments, $R^6$ is substituted naphthyl. In embodiments, $R^6$ is unsubstituted naphthyl.

In embodiments, $R^6$ is substituted or unsubstituted heteroaryl (e.g., 5 to 12 membered, 5 to 10 membered, 5 to 9 membered, or 5 to 6 membered). In embodiments, $R^6$ is substituted heteroaryl (e.g., 5 to 12 membered, 5 to 10 membered, 5 to 9 membered, or 5 to 6 membered). In embodiments, $R^6$ is unsubstituted heteroaryl (e.g., 5 to 12 membered, 5 to 10 membered, 5 to 9 membered, or 5 to 6 membered). In embodiments, R⁶ is substituted or unsubstituted 5 to 12 membered heteroaryl. In embodiments, R⁶ is substituted 5 to 12 membered heteroaryl. In embodiments, R⁶ is unsubstituted 5 to 12 membered heteroaryl. In embodiments, R⁶ is substituted or unsubstituted 5 to 10 membered heteroaryl. In embodiments, R⁶ is substituted 5 to 10 membered heteroaryl. In embodiments, R⁶ is unsubstituted 5 to 10 membered heteroaryl. In embodiments, R⁶ is substituted or unsubstituted 5 to 9 membered heteroaryl. In embodiments, R⁶ is substituted 5 to 9 membered heteroaryl. In embodiments, R⁶ is unsubstituted 5 to 9 membered heteroaryl. In embodiments, R⁶ is substituted or unsubstituted 5 to 6 membered heteroaryl. In embodiments, R⁶ is substituted 5 to 6 membered heteroaryl. In embodiments, R⁶ is unsubstituted 5 to 6 membered heteroaryl. In embodiments, R⁶ is substituted or unsubstituted 5 membered heteroaryl. In embodiments, R⁶ is substituted 5 membered heteroaryl. In embodiments, R⁶ is unsubstituted 5 membered heteroaryl. In embodiments, R⁶ is substituted or unsubstituted 6 membered heteroaryl. In embodiments, R⁶ is substituted 6 membered heteroaryl. In embodiments, R⁶ is unsubstituted 6 membered heteroaryl. In embodiments, R⁶ is substituted or unsubstituted pyrrolyl. In embodiments, R⁶ is substituted pyrrolyl. In embodiments, R⁶ is unsubstituted pyrrolyl. In embodiments, R⁶ is substituted or unsubstituted pyridazinyl. In embodiments, R⁶ is substituted pyridazinyl. In embodiments, R⁶ is unsubstituted pyridazinyl. In embodiments, R⁶ is substituted or unsubstituted triazinyl. In embodiments, R⁶ is substituted triazinyl. In embodiments, R⁶ is unsubstituted triazinyl. In embodiments, R⁶ is substituted or unsubstituted pyrimidinyl. In embodiments, R⁶ is substituted pyrimidinyl. In embodiments, R⁶ is unsubstituted pyrimidinyl. In embodiments, R⁶ is substituted or unsubstituted pyrazinyl. In embodiments, R⁶ is substituted pyrazinyl. In embodiments, R⁶ is unsubstituted pyrazinyl. In embodiments, R⁶ is substituted or unsubstituted imidazolyl. In embodiments, R⁶ is substituted imidazolyl. In embodiments, R⁶ is unsubstituted imidazolyl. In embodiments, R⁶ is substituted or unsubstituted purinyl. In embodiments, R⁶ is substituted purinyl. In embodiments, R⁶ is unsubstituted purinyl. In embodiments, R⁶ is substituted or unsubstituted thiazolyl. In embodiments, R⁶ is substituted thiazolyl. In embodiments, R⁶ is unsubstituted thiazolyl. In embodiments, R⁶ is substituted or unsubstituted furyl. In embodiments, R⁶ is substituted furyl. In embodiments, R⁶ is unsubstituted furyl. In embodiments, R⁶ is substituted or unsubstituted pyridyl. In embodiments, R⁶ is substituted pyridyl. In embodiments, R⁶ is unsubstituted pyridyl. In embodiments, R⁶ is substituted or unsubstituted pyrimidyl. In embodiments, R⁶ is substituted pyrimidyl. In embodiments, R⁶ is unsubstituted pyrimidyl.

In embodiments, R⁶ is

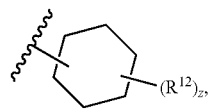

In embodiments, R⁶ is

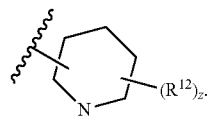

In embodiments, R⁶ is

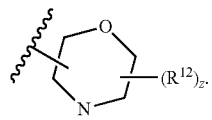

In embodiments, R⁶ is

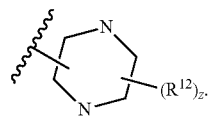

In embodiments, R⁶ is

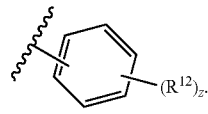

In embodiments, R⁶ is

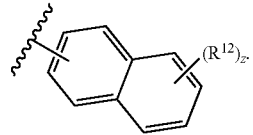

In embodiments, R⁶ is

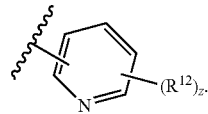

In embodiments, R⁶ is

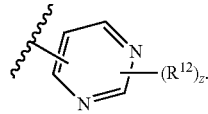

In embodiments, R⁶ is

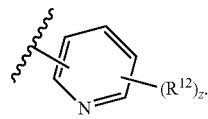

$R^{12}$ is independently halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n12 is independently an integer from 0 to 4. m12 and v12 are independently an integer from 1 to 2. $X^{12}$ is independently —F, —Cl, —Br or —I. z is an integer from 0 to 11. Two $R^{12}$s may be optionally be joined to form a substituted or unsubstituted cycloalkyl, substituted or unsubstituted heterocycloalkyl, substituted or unsubstituted aryl, or substituted or unsubstituted heteroaryl.

$R^{12A}$, $R^{12B}$, $R^{12C}$, and $R^{12D}$ are independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is independently —F, —Cl, —Br or —I.

In embodiments, z is an integer from 0 to 11. In embodiments, z is an integer from 0 to 10. In embodiments, z is an integer from 0 to 9. In embodiments, z is an integer from 0 to 8. In embodiments, z is an integer from 0 to 7. In embodiments, z is an integer from 0 to 6. In embodiments, z is an integer from 0 to 5. In embodiments, z is an integer from 0 to 4. In embodiments, z is an integer from 0 to 3. In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9. In embodiments, z is 10. In embodiments, z is 11.

In embodiments, the compound has a formula:

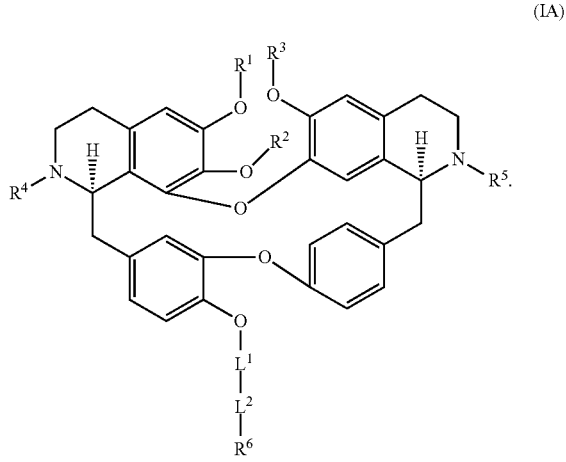

(IA)

In embodiments, the compound has a formula:

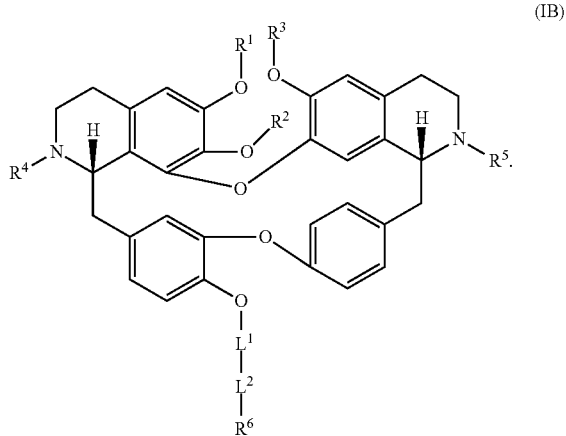

(IB)

In embodiments, $L^1$ is substituted or unsubstituted $C_1$-$C_{10}$ alkylene. In embodiments, $L^1$ is substituted $C_1$-$C_{10}$ alkylene. In embodiments, $L^1$ is unsubstituted $C_1$-$C_{10}$ alkylene. In embodiments, $L^1$ is substituted or unsubstituted $C_1$-$C_8$ alkylene. In embodiments, $L^1$ is substituted $C_1$-$C_8$ alkylene. In embodiments, $L^1$ is unsubstituted $C_1$-$C_8$ alkylene. In embodiments, $L^1$ is substituted or unsubstituted $C_1$-$C_6$ alkylene. In embodiments, $L^1$ is substituted $C_1$-$C_6$ alkylene. In embodiments, $L^1$ is unsubstituted $C_1$-$C_6$ alkylene. In embodiments, $L^1$ is substituted or unsubstituted $C_1$-$C_5$ alkylene. In embodiments, $L^1$ is substituted $C_1$-$C_5$ alkylene. In embodiments, $L^1$ is unsubstituted $C_1$-$C_5$ alkylene. In embodiments, $L^1$ is substituted or unsubstituted $C_1$-$C_4$ alkylene. In embodiments, $L^1$ is substituted $C_1$-$C_4$ alkylene. In embodiments, $L^1$ is unsubstituted $C_1$-$C_4$ alkylene. In embodiments, $L^1$ is substituted or unsubstituted $C_1$-$C_3$ alkylene. In embodiments, $L^1$ is substituted $C_1$-$C_3$ alkylene. In embodiments, $L^1$ is unsubstituted $C_1$-$C_3$ alkylene. In embodiments, $L^1$ is substituted or unsubstituted $C_1$-$C_2$ alkylene. In embodiments, $L^1$ is substituted $C_1$-$C_2$ alkylene. In embodiments, $L^1$ is unsubstituted $C_1$-$C_2$ alkylene. In embodiments, $L^1$ is substituted or unsubstituted ethylene. In embodiments, $L^1$ is substituted ethylene. In embodiments, $L^1$ is unsubstituted ethylene. In embodiments, $L^1$ is substituted or unsubstituted methylene. In embodiments, $L^1$ is substituted methylene. In embodiments, $L^1$ is unsubstituted methylene.

In embodiments, each $R^{2A}$ and $R^{2B}$ is independently hydrogen or substituted or unsubstituted $C_1$-$C_5$ alkyl. In embodiments, each $R^{2A}$ and $R^{2B}$ is independently hydrogen or unsubstituted $C_1$-$C_5$ alkyl. In embodiments, each $R^{2A}$ and $R^{2B}$ is independently hydrogen or substituted or unsubstituted $C_1$-$C_3$ alkyl. In embodiments, each $R^{2A}$ and $R^{2B}$ is independently hydrogen or unsubstituted $C_1$-$C_3$ alkyl. In embodiments, each $R^{2A}$ and $R^{2B}$ is independently hydrogen or substituted or unsubstituted $C_1$-$C_2$ alkyl. In embodiments, each $R^{2A}$ and $R^{2B}$ is independently hydrogen or unsubstituted $C_1$-$C_2$ alkyl.

In embodiments, $R^{2A}$ is hydrogen. In embodiments, $R^{2A}$ is substituted or unsubstituted $C_1$-$C_5$ alkyl. In embodiments, $R^{2A}$ is substituted $C_1$-$C_5$ alkyl. In embodiments, $R^{2A}$ is unsubstituted $C_1$-$C_5$ alkyl. In embodiments, $R^{2A}$ is substituted or unsubstituted $C_1$-$C_3$ alkyl. In embodiments, $R^{2A}$ is substituted $C_1$-$C_3$ alkyl. In embodiments, $R^{2A}$ is unsubstituted $C_1$-$C_3$ alkyl. In embodiments, $R^{2A}$ is substituted or unsubstituted $C_1$-$C_2$ alkyl. In embodiments, $R^{2A}$ is substituted $C_1$-$C_2$ alkyl. In embodiments, $R^{2A}$ is unsubstituted $C_1$-$C_2$ alkyl. In embodiments, $R^{2A}$ is substituted or unsubstituted ethyl. In embodiments, $R^{2A}$ is substituted ethyl. In embodiments, $R^{2A}$ is unsubstituted ethyl. In embodiments, $R^{2A}$ is substituted or unsubstituted methyl. In embodiments, $R^{2A}$ is substituted methyl. In embodiments, $R^{2A}$ is unsubstituted methyl.

In embodiments, $R^{2B}$ is hydrogen. In embodiments, $R^{2B}$ is substituted or unsubstituted $C_1$-$C_5$ alkyl. In embodiments, $R^{2B}$ is substituted $C_1$-$C_5$ alkyl. In embodiments, $R^{2B}$ is unsubstituted $C_1$-$C_5$ alkyl. In embodiments, $R^{2B}$ is substituted or unsubstituted $C_1$-$C_3$ alkyl. In embodiments, $R^{2B}$ is substituted $C_1$-$C_3$ alkyl. In embodiments, $R^{2B}$ is unsubstituted $C_1$-$C_3$ alkyl. In embodiments, $R^{2B}$ is substituted or unsubstituted $C_1$-$C_2$ alkyl. In embodiments, $R^{2B}$ is substituted $C_1$-$C_2$ alkyl. In embodiments, $R^{2B}$ is unsubstituted $C_1$-$C_2$ alkyl. In embodiments, $R^{2B}$ is substituted or unsubstituted ethyl. In embodiments, $R^{2B}$ is substituted ethyl. In embodiments, $R^{2B}$ is unsubstituted ethyl. In embodiments, $R^{2B}$ is substituted or unsubstituted methyl. In embodiments, $R^{2B}$ is substituted methyl. In embodiments, $R^{2B}$ is unsubstituted methyl. In embodiments, $R^{2A}$ and $R^{2B}$ are hydrogen. In embodiments, $R^{2A}$ and $R^{2B}$ are unsubstituted methyl.

In embodiments, $L^2$ is —NHS(O)$_2$— or —S(O)$_2$NH—. In embodiments, $L^2$ is —NHS(O)$_2$—. In embodiments, $L^2$ is —S(O)$_2$NH—. In embodiments, $L^2$ is —NCH$_3$S(O)$_2$— or —S(O)$_2$NCH$_3$—. In embodiments, $L^2$ is —NCH$_3$S(O)$_2$—. In embodiments, $L^2$ is —S(O)$_2$NCH$_3$—.

In embodiments, the compound has a formula:

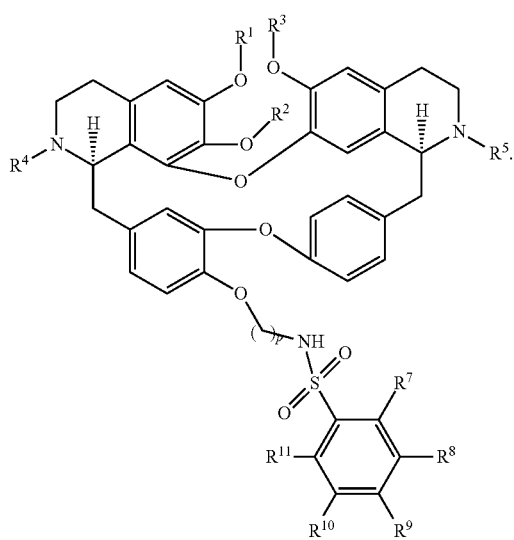

(II)

In embodiments, the compound has a formula:

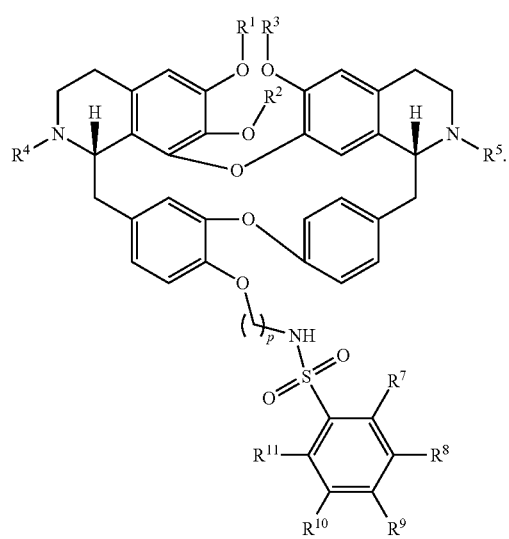

(II')

$R^7$ is hydrogen, halogen, —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O) R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O) R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O) R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O) NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)O R$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)O R$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ and $R^8$ together with atoms attached thereto may optionally be joined to form a substituted or unsubstituted cycloalkyl, substituted or unsubstituted heterocycloalkyl, substituted or unsubstituted aryl, or substituted or unsubstituted heteroaryl. In embodiments, $R^7$ and $R^8$ together with atoms attached thereto are optionally joined to form a substituted or unsubstituted cycloalkyl. In embodiments, $R^7$ and $R^8$ together with atoms attached thereto are joined to form a substituted cycloalkyl. In embodiments, $R^7$ and $R^8$ together with atoms attached thereto are joined to form an unsubstituted cycloalkyl. In embodiments, $R^7$ and $R^8$ together with atoms attached thereto are joined to form a substituted or unsubstituted heterocycloalkyl. In embodiments, $R^7$ and $R^8$ together with atoms attached thereto are joined to form a substituted heterocycloalkyl. In embodiments, $R^7$ and $R^8$ together with atoms attached thereto are joined to form an unsubstituted heterocycloalkyl. In embodiments, $R^7$ and $R^8$ together with atoms attached thereto are joined to form a substituted or unsubstituted aryl. In embodiments, $R^7$ and $R^8$ together with atoms attached thereto are joined to form a substituted aryl. In embodiments, $R^7$ and $R^8$ together with atoms attached thereto are joined to form an unsubstituted aryl. In embodiments, $R^7$ and $R^8$ together with atoms attached thereto are joined to form a substituted or unsubstituted heteroaryl. In embodiments, $R^7$ and $R^8$ together with atoms attached thereto are joined to form a substituted heteroaryl. In embodiments, $R^7$ and $R^8$ together with atoms attached thereto are joined to form an unsubstituted heteroaryl. In embodiments, $R^7$ and $R^8$ together with atoms attached thereto are joined to form a substituted or unsubstituted morpholinyl. In embodiments, $R^7$ and $R^8$ together with atoms attached thereto are joined to form a substituted morpholinyl. In embodiments, $R^7$ and $R^8$ together with atoms attached thereto are joined to form an unsubstituted morpholinyl. In embodiments, $R^7$ and $R^8$ together with atoms attached thereto are joined to form a substituted or unsubstituted piperazinyl. In embodiments, $R^7$ and $R^8$ together with atoms attached thereto are joined to form a substituted piperazinyl. In embodiments, $R^7$ and $R^8$ together with atoms attached thereto are joined to form an unsubstituted piperazinyl. In embodiments, $R^7$ and $R^8$ together with atoms attached thereto are joined to form a substituted or unsubstituted 1,4-dioxanyl. In embodiments, $R^7$ and $R^8$ together with atoms attached thereto are joined to form a substituted 1,4-dioxanyl. In embodiments, $R^7$ and $R^8$ together with atoms attached thereto are joined to form an unsubstituted 1,4-dioxanyl. In embodiments, $R^7$ and $R^8$ together with atoms attached thereto are joined to form a substituted or unsubstituted 1,3 dioxolanyl. In embodiments, $R^7$ and $R^8$ together with atoms attached thereto are joined to form a substituted 1,3 dioxolanyl. In embodiments, $R^7$ and $R^8$ together with atoms attached thereto are joined to form an unsubstituted 1,3 dioxolanyl.

$R^8$ and $R^9$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. In embodiments, $R^8$ and $R^9$ together with atoms attached thereto are joined to form a substituted or unsubstituted cycloalkyl. In embodiments, $R^8$ and $R^9$ together with atoms attached thereto are joined to form a substituted cycloalkyl. In embodiments, $R^8$ and $R^9$ together with atoms attached thereto are joined to form an unsubstituted cycloalkyl. In embodiments, $R^8$ and $R^9$ together with atoms attached thereto are joined to form a substituted or unsubstituted heterocycloalkyl. In embodiments, $R^8$ and $R^9$ together with atoms attached thereto are joined to form a substituted heterocycloalkyl. In embodiments, $R^8$ and $R^9$ together with atoms attached thereto are joined to form an unsubstituted heterocycloalkyl. In embodiments, $R^8$ and $R^9$ together with atoms attached thereto are joined to form a substituted or unsubstituted aryl. In embodiments, $R^8$ and $R^9$ together with atoms attached thereto are joined to form a substituted aryl. In embodiments, $R^8$ and $R^9$ together with atoms attached thereto are joined to form an unsubstituted aryl. In embodiments, $R^8$ and $R^9$ together with atoms attached thereto are joined to form a substituted or unsubstituted heteroaryl. In embodiments, $R^8$ and $R^9$ together with atoms attached thereto are joined to form a substituted heteroaryl. In embodiments, $R^8$ and $R^9$ together with atoms attached thereto are joined to form an unsubstituted heteroaryl. In embodiments, $R^8$ and $R^9$ together with atoms attached thereto are joined to form a substituted or unsubstituted morpholinyl. In embodiments, $R^8$ and $R^9$ together with atoms attached thereto are joined to form a substituted morpholinyl. In embodiments, $R^8$ and $R^9$ together with atoms attached thereto are joined to form an unsubstituted morpholinyl. In embodiments, $R^8$ and $R^9$ together with atoms attached thereto are joined to form a substituted or unsubstituted piperazinyl. In embodiments, $R^8$ and $R^9$ together with atoms attached thereto are joined to form a substituted piperazinyl. In embodiments, $R^8$ and $R^9$ together with atoms attached thereto are joined to form an unsubstituted piperazinyl. In embodiments, $R^8$ and $R^9$ together with atoms attached thereto are joined to form a substituted or unsubstituted 1,4-dioxanyl. In embodiments, $R^8$ and $R^9$ together with atoms attached thereto are joined to form a substituted 1,4-dioxanyl. In embodiments, $R^8$ and $R^9$ together with atoms attached thereto are joined to form an unsubstituted 1,4-dioxanyl. In embodiments, $R^8$ and $R^9$ together with atoms attached thereto are joined to form a substituted or unsubstituted 1,3 dioxolanyl. In embodiments, $R^8$ and $R^9$ together with atoms attached thereto are joined to form a substituted 1,3 dioxolanyl. In embodiments, $R^8$ and $R^9$ together with atoms attached thereto are joined to form an unsubstituted 1,3 dioxolanyl.

$R^9$ and $R^{10}$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. In embodiments, $R^9$ and $R^{10}$ together with atoms attached thereto are joined to form a substituted or unsubstituted cycloalkyl. In embodiments, $R^9$ and $R^{10}$ together with atoms attached thereto are joined to form a substituted cycloalkyl. In embodiments, $R^9$ and $R^{10}$ together with atoms attached thereto are joined to form an unsubstituted cycloalkyl. In embodiments, $R^9$ and $R^{10}$ together with atoms attached thereto are joined to form a substituted or unsubstituted heterocycloalkyl. In embodiments, $R^9$ and $R^{10}$ together with atoms attached thereto are joined to form a substituted heterocycloalkyl. In embodiments, $R^9$ and $R^{10}$ together with atoms attached thereto are joined to form an unsubstituted heterocycloalkyl. In embodiments, $R^9$ and $R^{10}$ together with atoms attached thereto are joined to form a substituted or unsubstituted aryl. In embodiments, $R^9$ and $R^{10}$ together with atoms attached thereto are joined to form a substituted aryl. In embodiments, $R^9$ and $R^{10}$ together with atoms attached thereto are joined to form an unsubstituted aryl. In embodiments, $R^9$ and $R^{10}$ together with atoms attached thereto are joined to form a substituted or unsubstituted heteroaryl. In embodiments, $R^9$ and $R^{10}$ together with atoms attached thereto are joined to form a substituted heteroaryl. In embodiments, $R^9$ and $R^{10}$ together with atoms attached thereto are joined to form an unsubstituted heteroaryl. In embodiments, $R^9$ and $R^{10}$ together with atoms attached thereto are joined to form a substituted or unsubstituted morpholinyl. In embodiments, $R^9$ and $R^{10}$ together with atoms attached thereto are joined to form a substituted morpholinyl. In embodiments, $R^9$ and $R^{10}$ together with atoms attached thereto are joined to form an unsubstituted morpholinyl. In embodiments, $R^9$ and $R^{10}$ together with atoms attached thereto are joined to form a substituted or unsubstituted piperazinyl. In embodiments, $R^9$ and $R^{10}$ together with atoms attached thereto are joined to form a substituted piperazinyl. In embodiments, $R^9$ and $R^{10}$ together with atoms attached thereto are joined to form an unsubstituted piperazinyl. In embodiments, $R^9$ and $R^{10}$ together with atoms attached thereto are joined to form a substituted or unsubstituted 1,4-dioxanyl. In embodiments, $R^9$ and $R^{10}$ together with atoms attached thereto are joined to form a substituted 1,4-dioxanyl. In embodiments, $R^9$ and $R^{10}$ together with atoms attached thereto are joined to form an unsubstituted 1,4-dioxanyl. In embodiments, $R^9$ and $R^{10}$ together with atoms attached thereto are joined to form a substituted or unsubstituted 1,3 dioxolanyl. In embodiments, $R^9$ and $R^{10}$ together with atoms attached thereto are joined to form a substituted 1,3 dioxolanyl. In embodiments, $R^9$ and $R^{10}$ together with atoms attached thereto are joined to form an unsubstituted 1,3 dioxolanyl.

$R^{10}$ and $R^{11}$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. In embodiments, $R^{10}$ and $R^{11}$ together with atoms attached thereto are joined to form a substituted or unsubstituted cycloalkyl. In embodiments, $R^{10}$ and $R^{11}$ together with atoms attached thereto are joined to form a substituted cycloalkyl. In embodiments, $R^{10}$ and $R^{11}$ together with atoms attached thereto are joined to form an unsubstituted cycloalkyl. In embodiments, $R^{10}$ and $R^{11}$ together with atoms attached thereto are joined to form a substituted or unsubstituted heterocycloalkyl. In embodiments, $R^{10}$ and $R^{11}$ together with atoms attached thereto are joined to form a substituted heterocycloalkyl. In embodiments, $R^{10}$ and $R^{11}$ together with atoms attached thereto are joined to form an unsubstituted heterocycloalkyl. In embodiments, $R^{10}$ and $R^{11}$ together with atoms attached thereto are joined to form a substituted or unsubstituted aryl. In embodiments, $R^{10}$ and $R^{11}$ together with atoms attached thereto are joined to form a substituted aryl. In embodiments, $R^{10}$ and $R^{11}$ together with atoms attached thereto are joined to form an unsubstituted aryl. In embodiments, $R^{10}$ and $R^{11}$ together with atoms attached thereto are joined to form a substituted or unsubstituted heteroaryl. In embodiments, $R^{10}$ and $R^{11}$ together with atoms attached thereto are joined to form a substituted heteroaryl. In embodiments, $R^{10}$ and $R^{11}$ together with atoms attached thereto are joined to form an unsubstituted heteroaryl. In embodiments, $R^{10}$ and $R^{11}$ together with atoms attached thereto are joined to form a substituted or unsubstituted morpholinyl. In embodiments, $R^{10}$ and $R^{11}$ together with atoms attached thereto are joined to form a substituted morpholinyl. In embodiments, $R^{10}$ and $R^{11}$ together with atoms attached thereto are joined to form an unsubstituted morpholinyl. In embodiments, $R^{10}$ and $R^{11}$ together with atoms attached thereto are joined to form a substituted or unsubstituted piperazinyl. In embodiments, $R^{10}$ and $R^{11}$ together with atoms attached thereto are joined to form a substituted piperazinyl. In embodiments, $R^{10}$ and $R^{11}$ together with atoms attached thereto are joined to form an unsubstituted piperazinyl. In embodiments, $R^{10}$ and $R^{11}$ together with atoms attached thereto are joined to form a substituted or unsubstituted 1,4-dioxanyl. In embodiments, $R^{10}$ and $R^{11}$ together with atoms attached thereto are joined to form a substituted 1,4-dioxanyl. In embodiments, $R^{10}$ and $R^{11}$ together with atoms attached thereto are joined to form an unsubstituted 1,4-dioxanyl. In embodiments, $R^{10}$ and $R^{11}$ together with atoms attached thereto are joined to form a substituted or unsubstituted 1,3 dioxolanyl. In embodiments, $R^{10}$ and $R^{11}$ together with atoms attached thereto are joined to form a substituted 1,3 dioxolanyl. In embodiments, $R^{10}$ and $R^{11}$ together with atoms attached thereto are joined to form an unsubstituted 1,3 dioxolanyl.

$R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, and $R^{11D}$ are independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

p is an integer from 1 to 10. n7, n8, n9, n10, and n11 are independently an integer from 0 to 4. m7, m8, m9, m10, m11, v7, v8, v9, v10, and v11 are independently an integer from 1 to 2. $X^7$, $X^8$, $X^9$, $X^{10}$, and $X^{11}$ are independently $-F$, $-Cl$, $-Br$ or $-I$.

In embodiments, $R^7$ is hydrogen, halogen, $-N_3$, $-CN$, $-NO_2$ or substituted or unsubstituted alkyl. In embodiments, $R^7$ is hydrogen. In embodiments, $R^7$ is $-F$, $-Cl$, $-Br$ or $-I$. In embodiments, $R^7$ is $-F$. In embodiments, $R^7$ is $-Cl$. In embodiments, $R^7$ is $-Br$. In embodiments, $R^7$ is $-I$. In embodiments, $R^7$ is $-N_3$. In embodiments, $R^7$ is $-CN$. In embodiments, $R^7$ is $-NO_2$.

In embodiments, $R^7$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^7$ is substituted or unsubstituted $C_1$-$C_{20}$ alkyl. In embodiments, $R^7$ is substituted $C_1$-$C_{20}$ alkyl. In embodiments, $R^7$ is unsubstituted $C_1$-$C_{20}$ alkyl. In embodiments, $R^7$ is substituted or unsubstituted $C_1$-$C_{12}$ alkyl. In embodiments, $R^7$ is substituted $C_1$-$C_{12}$ alkyl. In embodiments, $R^7$ is unsubstituted $C_1$-$C_{12}$ alkyl. In embodiments, $R^7$ is substituted or unsubstituted $C_1$-$C_8$ alkyl. In embodiments, $R^7$ is substituted $C_1$-$C_8$ alkyl. In embodiments, $R^7$ is unsubstituted $C_1$-$C_8$ alkyl. In embodiments, $R^7$ is substituted or unsubstituted $C_1$-$C_6$ alkyl. In embodiments, $R^7$ is substituted $C_1$-$C_6$ alkyl. In embodiments, $R^7$ is unsubstituted $C_1$-$C_6$ alkyl. In embodiments, $R^7$ is substituted or unsubstituted $C_1$-$C_4$ alkyl. In embodiments, $R^7$ is substituted $C_1$-$C_4$ alkyl. In embodiments, $R^7$ is unsubstituted $C_1$-$C_4$ alkyl. In embodiments, $R^7$ is substituted or unsubstituted $C_1$-$C_2$ alkyl. In embodiments, $R^7$ is substituted $C_1$-$C_2$ alkyl. In embodiments, $R^7$ is unsubstituted $C_1$-$C_2$ alkyl. In embodiments, $R^7$ is substituted or unsubstituted ethyl. In embodiments, $R^7$ is substituted ethyl. In embodiments, $R^7$ is unsubstituted ethyl. In embodiments, $R^7$ is substituted or unsubstituted methyl. In embodiments, $R^7$ is substituted methyl. In embodiments, $R^7$ is unsubstituted methyl.

In embodiments, $R^8$ is hydrogen, halogen, $-N_3$, $-CN$, $-NO_2$ or substituted or unsubstituted alkyl. In embodiments, $R^8$ is hydrogen. In embodiments, $R^8$ is $-F$, $-Cl$, $-Br$ or $-I$. In embodiments, $R^8$ is $-F$. In embodiments, $R^8$ is $-Cl$. In embodiments, $R^8$ is $-Br$. In embodiments, $R^8$ is $-I$. In embodiments, $R^8$ is $-N_3$. In embodiments, $R^8$ is $-CN$. In embodiments, $R^8$ is $-NO_2$.

In embodiments, $R^8$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^8$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^8$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^8$ is substituted or unsubstituted $C_1$-$C_{20}$ alkyl. In embodiments, $R^8$ is substituted $C_1$-$C_{20}$ alkyl. In embodiments, $R^8$ is unsubstituted $C_1$-$C_{20}$ alkyl. In embodiments, $R^8$ is substituted or unsubstituted $C_1$-$C_{12}$ alkyl. In embodiments, $R^8$ is substituted $C_1$-$C_{12}$ alkyl. In embodiments, $R^8$ is unsubstituted $C_1$-$C_{12}$ alkyl. In embodiments, $R^8$ is substituted or unsubstituted $C_1$-$C_8$ alkyl. In embodiments, $R^8$ is substituted $C_1$-$C_8$ alkyl. In embodiments, $R^8$ is unsubstituted $C_1$-$C_8$ alkyl. In embodiments, $R^8$ is substituted or unsubstituted $C_1$-$C_6$ alkyl. In embodiments, $R^8$ is substituted $C_1$-$C_6$ alkyl. In embodiments, $R^8$ is unsubstituted $C_1$-$C_6$ alkyl. In embodiments, $R^8$ is substituted or unsubstituted $C_1$-$C_4$ alkyl. In embodiments, $R^8$ is substituted $C_1$-$C_4$ alkyl. In embodiments, $R^8$ is unsubstituted $C_1$-$C_4$ alkyl. In embodiments, $R^8$ is substituted or unsubstituted $C_1$-$C_2$ alkyl. In embodiments, $R^8$ is substituted $C_1$-$C_2$ alkyl. In embodiments, $R^8$ is unsubstituted $C_1$-$C_2$ alkyl. In embodiments, $R^8$ is substituted or unsubstituted ethyl. In embodiments, $R^8$ is substituted ethyl. In embodiments, $R^8$ is unsubstituted ethyl. In embodiments, $R^8$ is substituted or unsubstituted methyl. In embodiments, $R^8$ is substituted methyl. In embodiments, $R^8$ is unsubstituted methyl.

In embodiments, $R^9$ is hydrogen, halogen, —$N_3$, —CN, —$NO_2$ or substituted or unsubstituted alkyl. In embodiments, $R^9$ is hydrogen. In embodiments, $R^9$ is —F, —Cl, —Br or —I. In embodiments, $R^9$ is —F. In embodiments, $R^9$ is —Cl. In embodiments, $R^9$ is —Br. In embodiments, $R^9$ is —I. In embodiments, $R^9$ is —$N_3$. In embodiments, $R^9$ is —CN. In embodiments, $R^9$ is —$NO_2$.

In embodiments, $R^9$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^9$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^9$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^9$ is substituted or unsubstituted $C_1$-$C_{20}$ alkyl. In embodiments, $R^9$ is substituted $C_1$-$C_{20}$ alkyl. In embodiments, $R^9$ is unsubstituted $C_1$-$C_{20}$ alkyl. In embodiments, $R^9$ is substituted or unsubstituted $C_1$-$C_{12}$ alkyl. In embodiments, $R^9$ is substituted $C_1$-$C_{12}$ alkyl. In embodiments, $R^9$ is unsubstituted $C_1$-$C_{12}$ alkyl. In embodiments, $R^9$ is substituted or unsubstituted $C_1$-$C_8$ alkyl. In embodiments, $R^9$ is substituted $C_1$-$C_8$ alkyl. In embodiments, $R^9$ is unsubstituted $C_1$-$C_8$ alkyl. In embodiments, $R^9$ is substituted or unsubstituted $C_1$-$C_6$ alkyl. In embodiments, $R^9$ is substituted $C_1$-$C_6$ alkyl. In embodiments, $R^9$ is unsubstituted $C_1$-$C_6$ alkyl. In embodiments, $R^9$ is substituted or unsubstituted $C_1$-$C_4$ alkyl. In embodiments, $R^9$ is substituted $C_1$-$C_4$ alkyl. In embodiments, $R^9$ is unsubstituted $C_1$-$C_4$ alkyl. In embodiments, $R^9$ is substituted or unsubstituted $C_1$-$C_2$ alkyl. In embodiments, $R^9$ is substituted $C_1$-$C_2$ alkyl. In embodiments, $R^9$ is unsubstituted $C_1$-$C_2$ alkyl. In embodiments, $R^9$ is substituted or unsubstituted ethyl. In embodiments, $R^9$ is substituted ethyl. In embodiments, $R^9$ is unsubstituted ethyl. In embodiments, $R^9$ is substituted or unsubstituted methyl. In embodiments, $R^9$ is substituted methyl. In embodiments, $R^9$ is unsubstituted methyl.

In embodiments, $R^{10}$ is hydrogen, halogen, —$N_3$, —CN, —$NO_2$ or substituted or unsubstituted alkyl. In embodiments, $R^{10}$ is hydrogen. In embodiments, $R^{10}$ is —F, —Cl, —Br or —I. In embodiments, $R^{10}$ is —F. In embodiments, $R^{10}$ is —Cl. In embodiments, $R^{10}$ is —Br. In embodiments, $R^{10}$ is —I. In embodiments, $R^{10}$ is —$N_3$. In embodiments, $R^{10}$ is —CN. In embodiments, $R^{10}$ is —$NO_2$.

In embodiments, $R^{10}$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{10}$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{10}$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{10}$ is substituted or unsubstituted $C_1$-$C_{20}$ alkyl. In embodiments, $R^{10}$ is substituted $C_1$-$C_{20}$ alkyl. In embodiments, $R^{10}$ is unsubstituted $C_1$-$C_{20}$ alkyl. In embodiments, $R^{10}$ is substituted or unsubstituted $C_1$-$C_{12}$ alkyl. In embodiments, $R^{10}$ is substituted $C_1$-$C_{12}$ alkyl. In embodiments, $R^{10}$ is unsubstituted $C_1$-$C_{12}$ alkyl. In embodiments, $R^{10}$ is substituted or unsubstituted $C_1$-$C_8$ alkyl. In embodiments, $R^{10}$ is substituted $C_1$-$C_8$ alkyl. In embodiments, $R^{10}$ is unsubstituted $C_1$-$C_8$ alkyl. In embodiments, $R^{10}$ is substituted or unsubstituted $C_1$-$C_6$ alkyl. In embodiments, $R^{10}$ is substituted $C_1$-$C_6$ alkyl. In embodiments, $R^{10}$ is unsubstituted $C_1$-$C_6$ alkyl. In embodiments, $R^{10}$ is substituted or unsubstituted $C_1$-$C_4$ alkyl. In embodiments, $R^{10}$ is substituted $C_1$-$C_4$ alkyl. In embodiments, $R^{10}$ is unsubstituted $C_1$-$C_4$ alkyl. In embodiments, $R^{10}$ is substituted or unsubstituted $C_1$-$C_2$ alkyl. In embodiments, $R^{10}$ is substituted $C_1$-$C_2$ alkyl. In embodiments, $R^{10}$ is unsubstituted $C_1$-$C_2$ alkyl. In embodiments, $R^{10}$ is substituted or unsubstituted ethyl. In embodiments, $R^{10}$ is substituted ethyl. In embodiments, $R^{10}$ is unsubstituted ethyl. In embodiments, $R^{10}$ is substituted or unsubstituted methyl. In embodiments, $R^{10}$ is substituted methyl. In embodiments, $R^{10}$ is unsubstituted methyl.

In embodiments, $R^{11}$ is hydrogen, halogen, —$N_3$, —CN, —$NO_2$ or substituted or unsubstituted alkyl. In embodiments, $R^{11}$ is hydrogen. In embodiments, $R^{11}$ is —F, —Cl, —Br or —I. In embodiments, $R^{11}$ is —F. In embodiments, $R^{11}$ is —Cl. In embodiments, $R^{11}$ is —Br. In embodiments, $R^{11}$ is —I. In embodiments, $R^{11}$ is —$N_3$. In embodiments, $R^{11}$ is —CN. In embodiments, $R^{11}$ is —$NO_2$.

In embodiments, $R^{11}$ is substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{11}$ is substituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{11}$ is unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$). In embodiments, $R^{11}$ is substituted or unsubstituted $C_1$-$C_{20}$ alkyl. In embodiments, $R^{11}$ is substituted $C_1$-$C_{20}$ alkyl. In embodiments, $R^{11}$ is unsubstituted $C_1$-$C_{20}$ alkyl. In embodiments, $R^{11}$ is substituted or unsubstituted $C_1$-$C_{12}$ alkyl. In embodiments, $R^{11}$ is substituted $C_1$-$C_{12}$ alkyl. In embodiments, $R^{11}$ is unsubstituted $C_1$-$C_{12}$ alkyl. In embodiments, $R^{11}$ is substituted or unsubstituted $C_1$-$C_8$ alkyl. In embodiments, $R^{11}$ is substituted $C_1$-$C_8$ alkyl. In embodiments, $R^{11}$ is unsubstituted $C_1$-$C_8$ alkyl. In embodiments, $R^{11}$ is substituted or unsubstituted $C_1$-$C_6$ alkyl. In embodiments, $R^{11}$ is substituted $C_1$-$C_6$ alkyl. In embodiments, $R^{11}$ is unsubstituted $C_1$-$C_6$ alkyl. In embodiments, $R^{11}$ is substituted or unsubstituted $C_1$-$C_4$ alkyl. In embodiments, $R^{11}$ is substituted $C_1$-$C_4$ alkyl. In embodiments, $R^{11}$ is unsubstituted $C_1$-$C_4$ alkyl. In embodiments, $R^{11}$ is substituted or unsubstituted $C_1$-$C_2$ alkyl. In embodiments, $R^{11}$ is substituted $C_1$-$C_2$ alkyl. In embodiments, $R^{11}$ is unsubstituted $C_1$-$C_2$ alkyl. In embodiments, $R^{11}$ is substituted or unsubstituted ethyl. In embodiments, $R^{11}$ is substituted ethyl. In embodiments, $R^{11}$ is unsubstituted ethyl. In embodiments, $R^{11}$ is substituted or unsubstituted methyl. In embodiments, $R^{11}$ is substituted methyl. In embodiments, $R^{11}$ is unsubstituted methyl.

In embodiments, the compound has a formula:

(III)

In embodiments, the compound has a formula:

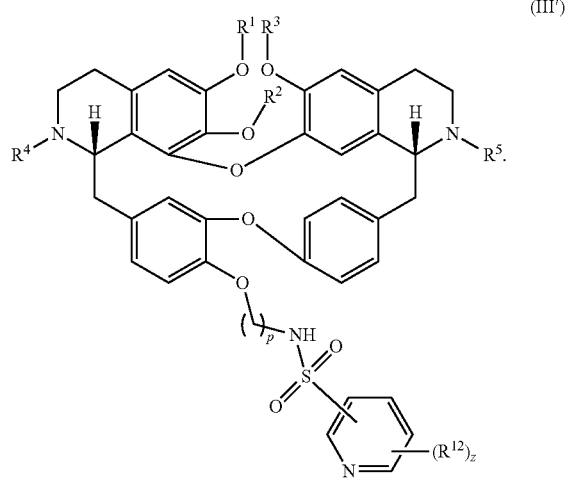

(III')

$R^1$, $R^2$, $R^3$, $R^4$, $R^5$, $R^{12}$, $R^{12A}$, $R^{12B}$, $R^{12C}$, $R^{12D}$, z and p are as described herein.

In embodiments, $R^{12}$ is independently halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)O R^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n12 is independently an integer from 0 to 4. m12 and v12 are independently an integer from 1 to 2. $X^{12}$ is independently $-F$, $-Cl$, $-Br$ or $-I$. $R^1$, $R^2$, $R^3$, $R^4$, $R^5$, $R^{12}$, $R^{12A}$, $R^{12B}$, $R^{12C}$, $R^{12D}$, z and p are as described herein. Two $R^{12}$s may be optionally be joined to form a substituted or unsubstituted cycloalkyl, substituted or unsubstituted heterocycloalkyl, substituted or unsubstituted aryl, or substituted or unsubstituted heteroaryl.

In embodiments, $R^{12A}$, $R^{12B}$, $R^{12C}$, and $R^{12D}$ are independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. X is independently $-F$, $-Cl$, $-Br$ or $-I$.

In embodiments, p is an integer from 1 to 10. In embodiments, p is 1. In embodiments, p is 2. In embodiments, p is 3. In embodiments, p is 4. In embodiments, p is 5. In embodiments, p is 6. In embodiments, p is 7. In embodiments, p is 8. In embodiments, p is 9. In embodiments, p is 10.

In embodiments, z is an integer from 0 to 4. In embodiments, z is 0. In embodiments, z is 1. In embodiments, z is 2. In embodiments, z is 3. In embodiments, z is 4.

In embodiments, $R^{12}$ is independently halogen (e.g., $-F$, $-Cl$, Fr or $-I$), $-NO_2$, $-N_3$, $-CN$, $-COOH$, $-COCH_3$, $-COH$, $-COOCH_3$, or substituted or unsubstituted alkyl. In embodiments, $R^{12}$ is independently $-F$ or $-Cl$. In embodiments, $R^{12}$ is independently $-NO_2$. In embodiments, $R^{12}$ is independently $-N_3$. In embodiments, $R^{12}$ is independently $-CN$. In embodiments, $R^{12}$ is independently $-COOH$, $-COCH_3$, $-COH$, or $-COOCH_3$. In embodiments, $R^{12}$ is independently substituted or unsubstituted alkyl. In embodiments, $R^{12}$ is independently substituted or unsubstituted $C_1$-$C_{20}$ alkyl. In embodiments, $R^{12}$ is independently substituted $C_1$-$C_{20}$ alkyl. In embodiments, $R^{12}$ is independently unsubstituted $C_1$-$C_{20}$ alkyl. In embodiments, $R^{12}$ is independently substituted or unsubstituted $C_1$-$C_{12}$ alkyl. In embodiments, $R^{12}$ is independently substituted $C_1$-$C_{12}$ alkyl. In embodiments, $R^{12}$ is independently unsubstituted $C_1$-$C_{12}$ alkyl. In embodiments, $R^{12}$ is independently substituted or unsubstituted $C_1$-$C_8$ alkyl. In embodiments, $R^{12}$ is independently substituted $C_1$-$C_8$ alkyl. In embodiments, $R^{12}$ is independently unsubstituted $C_1$-$C_8$ alkyl. In embodiments, $R^{12}$ is independently substituted or unsubstituted $C_1$-$C_6$ alkyl. In embodiments, $R^{12}$ is independently substituted $C_1$-$C_6$ alkyl. In embodiments, $R^{12}$ is independently unsubstituted $C_1$-$C_6$ alkyl. In embodiments, $R^{12}$ is independently substituted or unsubstituted $C_1$-$C_4$ alkyl. In embodiments, $R^{12}$ is independently substituted $C_1$-$C_4$ alkyl. In embodiments, $R^{12}$ is independently unsubstituted $C_1$-$C_4$ alkyl. In embodiments, $R^{12}$ is independently substituted or unsubstituted $C_1$-$C_2$ alkyl. In embodiments, $R^{12}$ is independently substituted $C_1$-$C_2$ alkyl. In embodiments, $R^{12}$ is independently unsubstituted $C_1$-$C_2$ alkyl. In embodiments, $R^{12}$ is independently substituted or unsubstituted ethyl. In embodiments, $R^{12}$ is independently substituted ethyl. In embodiments, $R^{12}$ is independently unsubstituted ethyl. In embodiments, $R^{12}$ is independently substituted or unsubstituted methyl. In embodiments, $R^{12}$ is independently substituted methyl. In embodiments, $R^{12}$ is independently unsubstituted methyl.

In embodiments, the compound has a formula:

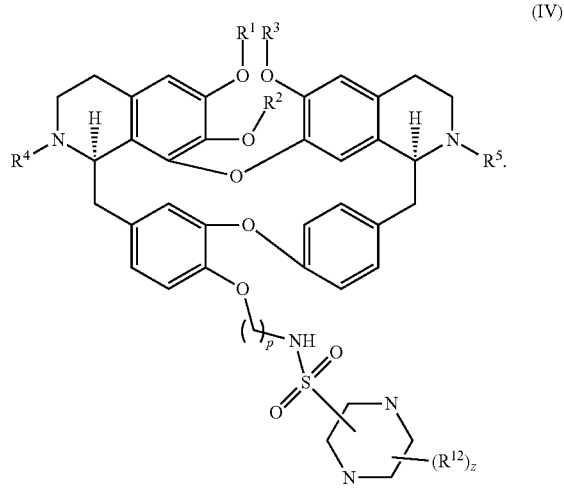

(IV)

In embodiments, the compound has a formula:

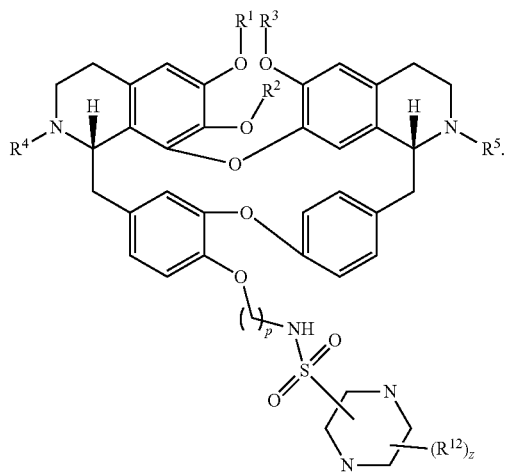

(IV')

$R^1$, $R^2$, $R^3$, $R^4$, $R^5$, $R^{12}$, and p are as described herein.

In embodiments, z is an integer from 0 to 9. In embodiments, z is 0. In embodiments, z is 1. In embodiments, z is 2. In embodiments, z is 3. In embodiments, z is 4. In embodiments, z is 5. In embodiments, z is 6. In embodiments, z is 7. In embodiments, z is 8. In embodiments, z is 9.

In embodiments, each $R^1$, $R^2$, $R^3$, $R^4$, and $R^5$ is independently unsubstituted $C_1$-$C_{10}$ alkyl. In embodiments, each $R^1$, $R^2$, $R^3$, $R^4$, and $R^5$ is independently unsubstituted $C_1$-$C_5$ alkyl. In embodiments, each $R^1$, $R^2$, $R^3$, $R^4$, and $R^5$ is independently unsubstituted methyl. In embodiments, $R^1$ and $R^2$ are unsubstituted methyl. In embodiments, $R^1$ and $R^3$ are unsubstituted methyl. In embodiments, $R^1$ and $R^4$ are unsubstituted methyl. In embodiments, $R^1$ and $R^5$ are unsubstituted methyl. In embodiments, $R^2$ and $R^3$ are unsubstituted methyl. In embodiments, $R^2$ and $R^4$ are unsubstituted methyl. In embodiments, $R^2$ and $R^5$ are unsubstituted methyl. In embodiments, $R^3$ and $R^4$ are unsubstituted methyl. In embodiments, $R^4$ and $R^5$ are unsubstituted methyl. In embodiments, $R^1$, $R^2$ and $R^3$ are unsubstituted methyl. In embodiments, $R^1$, $R^2$ and $R^4$ are unsubstituted methyl. In embodiments, $R^1$, $R^2$ and R5 are unsubstituted methyl. In embodiments, $R^1$, $R^3$ and $R^4$ are unsubstituted methyl. In embodiments, $R^1$, $R^3$ and $R^5$ are unsubstituted methyl. In embodiments, $R^1$, $R^4$ and $R^5$ are unsubstituted methyl. In embodiments, $R^2$, $R^3$ and $R^4$ are unsubstituted methyl. In embodiments, $R^2$, $R^3$ and $R^5$ are unsubstituted methyl. In embodiments, $R^2$, $R^4$ and $R^5$ are unsubstituted methyl. In embodiments, $R^3$, $R^4$ and $R^5$ are unsubstituted methyl. In embodiments, $R^1$, $R^2$, $R^3$, and $R^4$ is independently unsubstituted methyl. In embodiments, $R^1$, $R^2$, $R^3$, and $R^5$ is independently unsubstituted methyl. In embodiments, $R^1$, $R^2$, $R^4$, and $R^5$ is independently unsubstituted methyl. In embodiments, $R^1$, $R^3$, $R^4$, and $R^5$ is independently unsubstituted methyl. In embodiments, $R^2$, $R^3$, $R^4$, and $R^5$ is independently unsubstituted methyl. In embodiments, each $R^1$, $R^2$, $R^3$, $R^4$, and $R^5$ is independently hydrogen.

In embodiments, p is an integer from 2 to 4. In embodiments, p is 2 or 3. In embodiment, p is 2. In embodiment p is 3. In embodiments, p is 4.

In embodiments, each $R^7$, $R^8$, $R^9$, $R^{10}$, and $R^{11}$ is independently hydrogen, —F, —Cl, —NO$_2$ or unsubstituted methyl. In embodiments, $R^7$ is hydrogen, —F, —Cl, —NO$_2$ or unsubstituted methyl. In embodiments, $R^7$ is hydrogen. In embodiments, $R^7$ is —F. In embodiments, $R^7$ is —Cl. In embodiments, $R^7$ is —NO$_2$. In embodiments, $R^7$ is or unsubstituted methyl. In embodiments, $R^8$ is hydrogen, —F, —Cl, —NO$_2$ or unsubstituted methyl. In embodiments, $R^8$ is hydrogen. In embodiments, $R^8$ is —F. In embodiments, $R^8$ is —Cl. In embodiments, $R^8$ is —NO$_2$. In embodiments, $R^8$ is or unsubstituted methyl. In embodiments, $R^9$ is hydrogen, —F, —Cl, —NO$_2$ or unsubstituted methyl. In embodiments, $R^9$ is hydrogen. In embodiments, $R^9$ is —F. In embodiments, $R^9$ is —Cl. In embodiments, $R^9$ is —NO$_2$. In embodiments, $R^9$ is or unsubstituted methyl. In embodiments, $R^{10}$ is hydrogen, —F, —Cl, —NO$_2$ or unsubstituted methyl. In embodiments, $R^{10}$ is hydrogen. In embodiments, $R^{10}$ is —F. In embodiments, $R^{10}$ is —Cl. In embodiments, $R^{10}$ is —NO$_2$. In embodiments, $R^{10}$ is or unsubstituted methyl. In embodiments, $R^{11}$ is hydrogen, —F, —Cl, —NO$_2$ or unsubstituted methyl. In embodiments, $R^{11}$ is hydrogen. In embodiments, $R^{11}$ is —F. In embodiments, $R^{11}$ is —Cl. In embodiments, $R^{11}$ is —NO$_2$. In embodiments, $R^{11}$ is unsubstituted methyl.

In embodiments, the compound has a formula

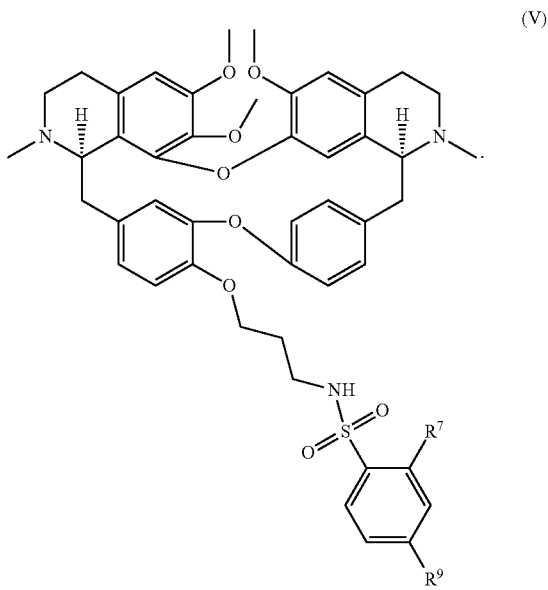

(V)

In embodiments, the compound has a formula

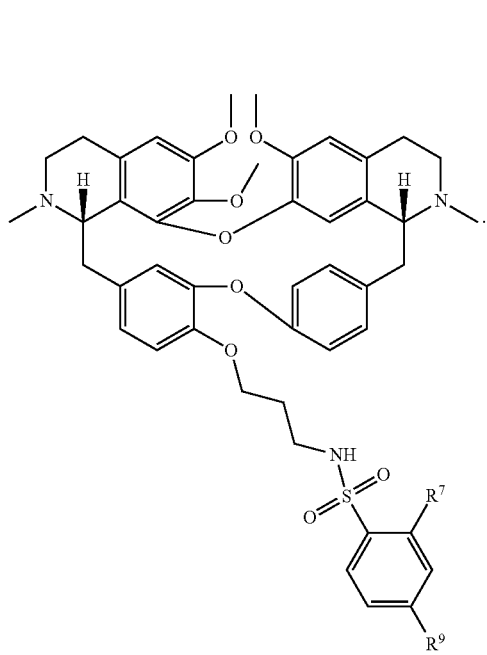

(V')

R⁷, and 9, and p are as described herein.

In embodiments, each R⁷ and R⁹ is independently hydrogen, —F or —NO₂. In embodiments, R⁷ is hydrogen. In embodiments, R⁷ is —F. In embodiments, R⁷ is —NO₂. In embodiments, R⁹ is hydrogen. In embodiments, R⁹ is —F. In embodiments, R⁹ is —NO₂. In embodiments, R⁷ is hydrogen and R⁹ is hydrogen. In embodiments, R⁷ is hydrogen and R⁹ is —F. In embodiments, R⁷ is hydrogen and R⁹ is —NO₂. In embodiments, R⁷ is —F and R⁹ is hydrogen. In embodiments, R⁷ is —F and R⁹ is —F. In embodiments, R⁷ is —F and R⁹ is —NO₂. In embodiments, R⁷ is —NO₂ and R⁹ is hydrogen. In embodiments, R⁷ is —NO₂ and R⁹ is —F. In embodiments, R⁷ is —NO₂ and R⁹ is —NO₂.

In embodiments, each R⁷ and R⁹ is independently hydrogen, —Cl or —NO₂. In embodiments, R⁷ is hydrogen. In embodiments, R⁷ is —Cl. In embodiments, R⁷ is —NO₂. In embodiments, R⁹ is hydrogen. In embodiments, R⁹ is —Cl. In embodiments, R⁹ is —NO₂. In embodiments, R⁷ is hydrogen and R⁹ is hydrogen. In embodiments, R⁷ is hydrogen and R⁹ is —Cl. In embodiments, R⁷ is hydrogen and R⁹ is —NO₂. In embodiments, R⁷ is —Cl and R⁹ is hydrogen. In embodiments, R⁷ is —Cl and R⁹ is —Cl. In embodiments, R⁷ is —Cl and R⁹ is —NO₂. In embodiments, R⁷ is —NO₂ and R⁹ is hydrogen. In embodiments, R⁷ is —NO₂ and R⁹ is —Cl. In embodiments, R⁷ is —NO₂ and R⁹ is —NO₂.

In embodiments, the compound has a formula

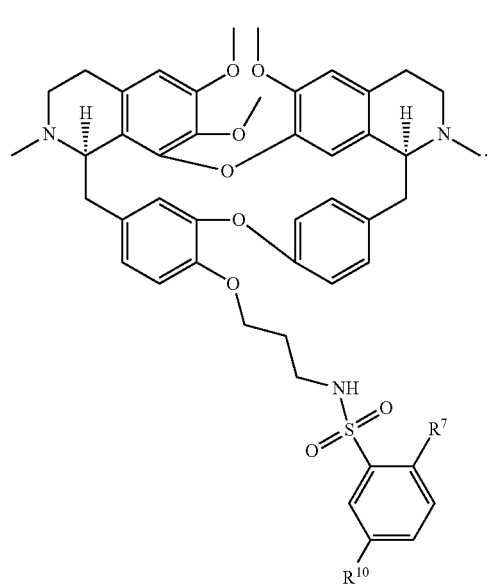

(VI)

R⁷ and R¹⁰ are as described herein. In embodiments, the compound has a formula

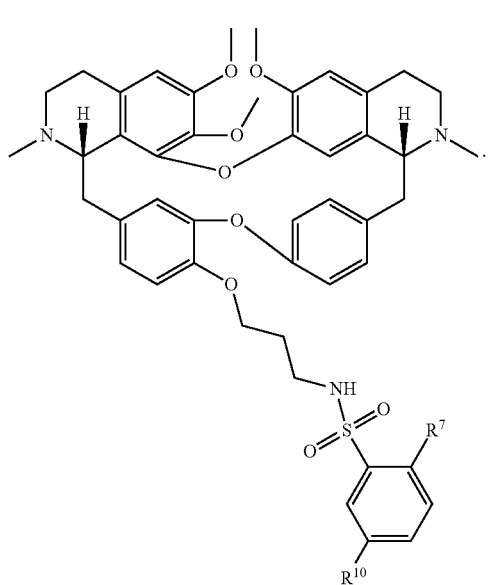

(VI')

R⁷ and R¹⁰ are as described herein.

In embodiments, each R⁷ and R¹⁰ is independently —Cl, —NO₂ or unsubstituted methyl. In embodiments, R⁷ is —Cl. In embodiments, R⁷ is —NO₂. In embodiments, R⁷ is unsubstituted methyl. In embodiments, R¹⁰ is —Cl. In embodiments, R¹⁰ is —NO₂. In embodiments, R¹⁰ is unsubstituted methyl. In embodiments, R⁷ is —Cl and R¹⁰ is —Cl. In embodiments, R⁷ is —Cl and R¹⁰ is —NO₂. In embodiments, R⁷ is —Cl and R¹⁰ is unsubstituted methyl. In embodiments, R⁷ is —NO₂ and R¹⁰ is —Cl. In embodiments, R⁷ is —NO₂ and R¹⁰ is —NO₂. In embodiments, R⁷ is —NO₂ and R¹⁰ is unsubstituted methyl. In embodiments, R⁷ is unsubstituted methyl and R¹⁰ is —Cl. In embodiments, $R^7$ is unsubstituted methyl and $R^{10}$ is —$NO_2$. In embodiments, $R^7$ is unsubstituted methyl and $R^{10}$ is unsubstituted methyl.

In embodiments, each $R^7$ and $R^{10}$ is independently —F, —$NO_2$ or unsubstituted methyl. In embodiments, $R^7$ is —F. In embodiments, $R^7$ is —$NO_2$. In embodiments, $R^7$ is unsubstituted methyl. In embodiments, $R^{10}$ is —F. In embodiments, $R^{10}$ is —$NO_2$. In embodiments, $R^{10}$ is unsubstituted methyl. In embodiments, $R^7$ is —F and $R^{10}$ is —F. In embodiments, $R^7$ is —F and $R^{10}$ is —$NO_2$. In embodiments, $R^7$ is —F and $R^{10}$ is unsubstituted methyl. In embodiments, $R^7$ is —$NO_2$ and $R^{10}$ is —F. In embodiments, $R^7$ is —$NO_2$ and $R^{10}$ is —$NO_2$. In embodiments, $R^7$ is —$NO_2$ and $R^{10}$ is unsubstituted methyl. In embodiments, $R^7$ is unsubstituted methyl and $R^{10}$ is —F. In embodiments, $R^7$ is unsubstituted methyl and $R^{10}$ is —$NO_2$. In embodiments, $R^7$ is unsubstituted methyl and $R^{10}$ is unsubstituted methyl.

In embodiments, the compound has a formula

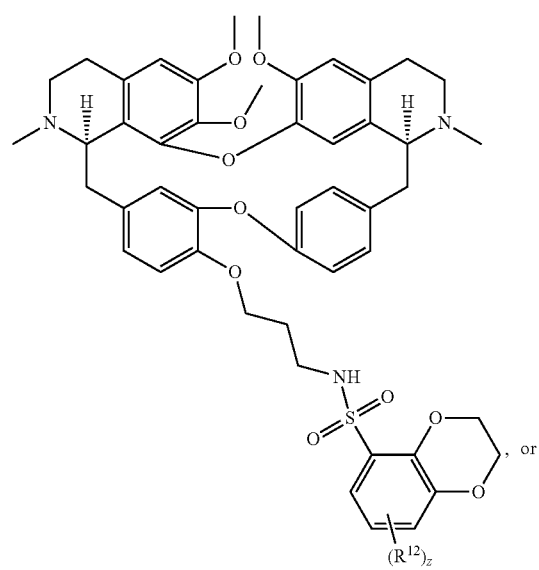

(VII-A)

, or

In embodiments, the compound has a formula

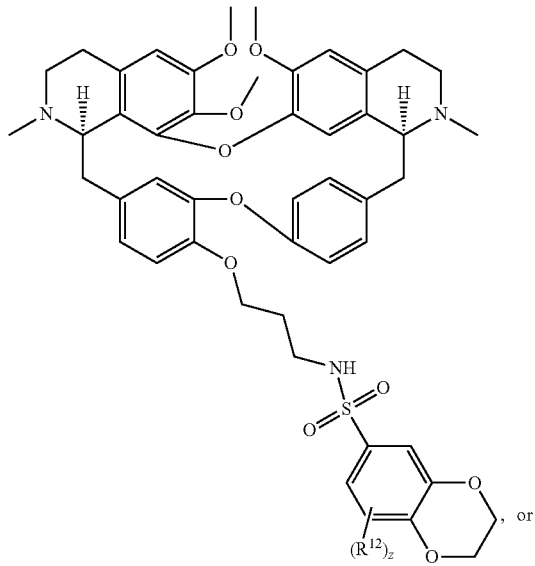

(VII-B)

, or

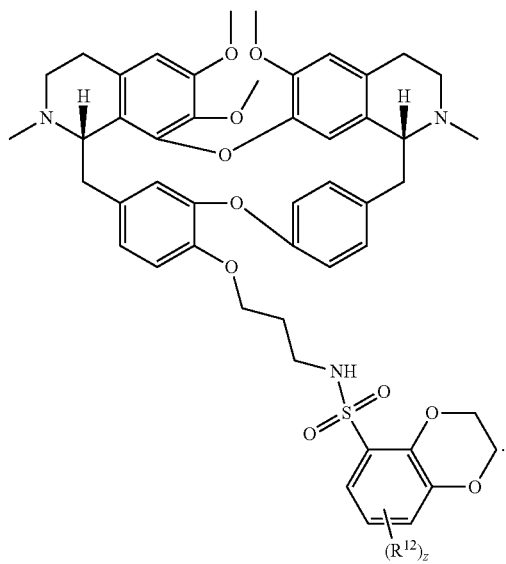

(VII-A′)

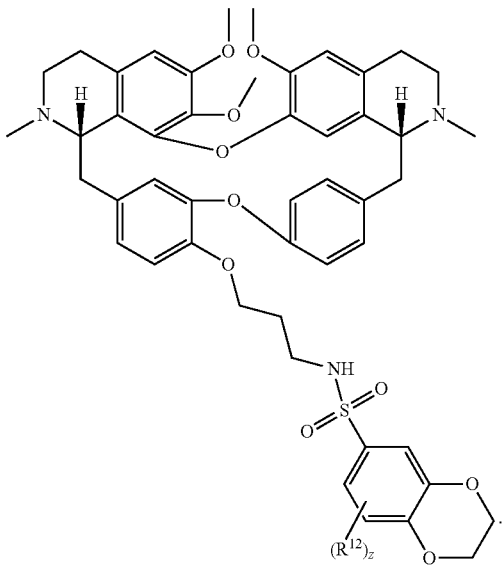

(VII-B′)

In embodiments, the compound has a formula

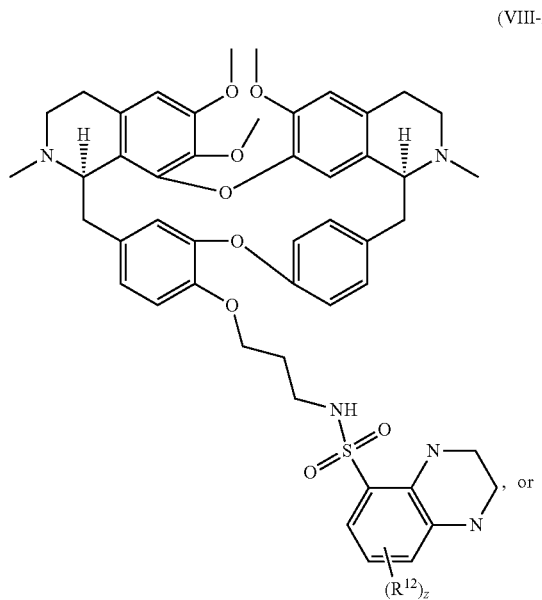

(VIII-A), or

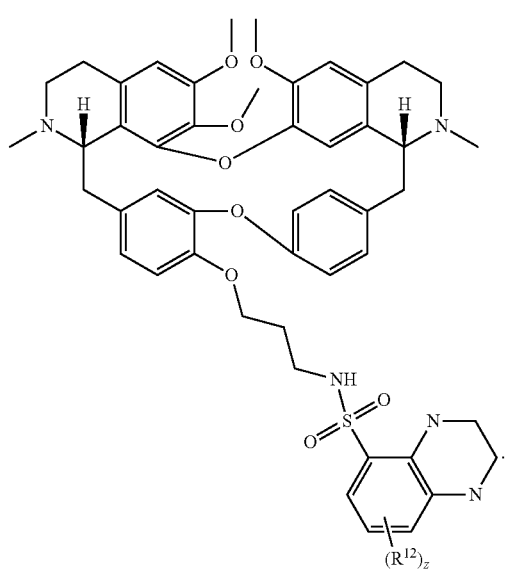

(VIII-A')

In embodiments, the compound has a formula

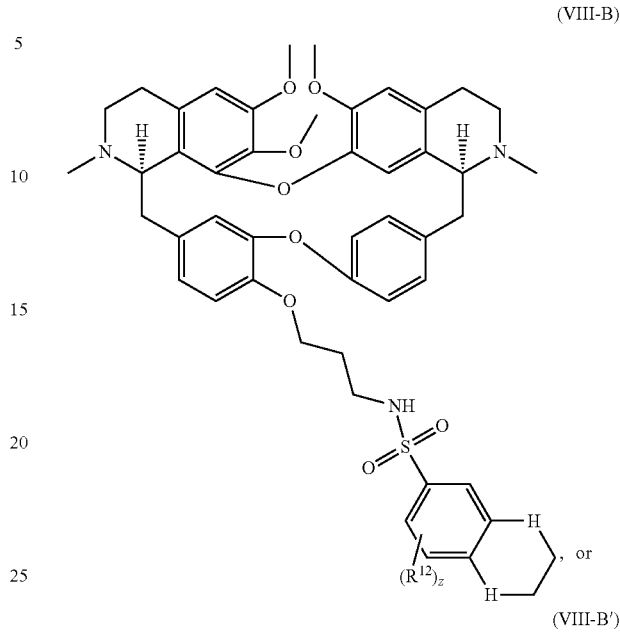

(VIII-B), or

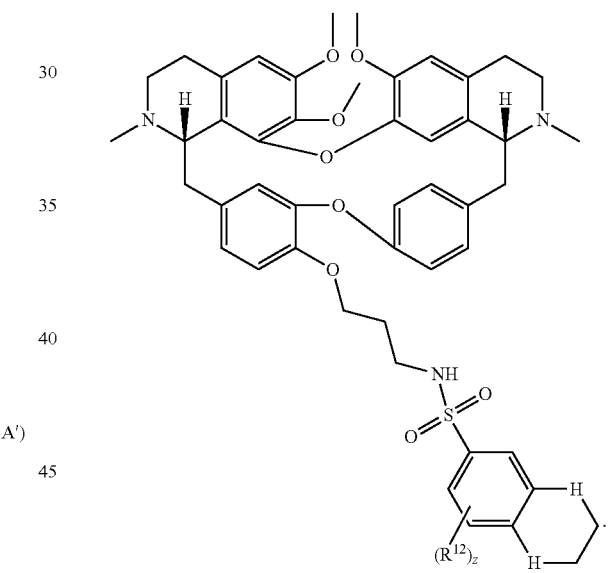

(VIII-B').

$R^{12}$ and z are as described herein.

In embodiments, z is 0. In embodiments, z is 1. In embodiments, z is 2. In embodiments, $R^{12}$ is independently —F, —Cl, —$NO_2$ or unsubstituted methyl.

In embodiments, $R^1$ is hydrogen, or substituted (e.g., substituted with a substituent group, a size-limited substituent group, or lower substituent group) or unsubstituted alkyl (e.g., $C_1$-$C_{10}$, $C_1$-$C_8$, $C_1$-$C_6$, $C_1$-$C_4$, or $C_1$-$C_2$). In embodiments, $R^1$ is hydrogen, or substituted (e.g., substituted with a substituent group, a size-limited substituent group, or lower substituent group) alkyl (e.g., $C_1$-$C_{10}$, $C_1$-$C_8$, $C_1$-$C_6$, $C_1$-$C_4$, or $C_1$-$C_2$). In embodiments, $R^1$ is hydrogen, or unsubstituted alkyl (e.g., $C_1$-$C_{10}$, $C_1$-$C_8$, $C_1$-$C_6$, $C_1$-$C_4$, or $C_1$-$C_2$). In embodiments, $R^1$ is hydrogen.

In embodiments, $R^1$ is $R^{1E}$-substituted or unsubstituted $C_1$-$C_{10}$ alkyl. In embodiments, $R^1$ is $R^{1E}$-substituted $C_1$-$C_{10}$ alkyl. In embodiments, $R^1$ is unsubstituted $C_1$-$C_{10}$ alkyl. In embodiments, $R^1$ is $R^{1E}$-substituted or unsubstituted $C_1$-$C_8$ alkyl. In embodiments, $R^1$ is $R^{1E}$-substituted $C_1$-$C_8$ alkyl. In embodiments, $R^1$ is unsubstituted $C_1$-$C_8$ alkyl. In embodiments, $R^1$ is $R^{1E}$-substituted or unsubstituted $C_1$-$C_6$ alkyl. In embodiments, $R^1$ is $R^{1E}$-substituted $C_1$-$C_6$ alkyl. In embodiments, $R^1$ is unsubstituted $C_1$-$C_6$ alkyl. In embodiments, $R^1$ is $R^{1E}$-substituted or unsubstituted $C_1$-$C_4$ alkyl. In embodiments, $R^1$ is $R^{1E}$-substituted $C_1$-$C_4$ alkyl. In embodiments, $R^1$ is unsubstituted $C_1$-$C_4$ alkyl. In embodiments, $R^1$ is $R^{1E}$-substituted or unsubstituted $C_1$-$C_2$ alkyl. In embodiments, $R^1$ is $R^{1E}$-substituted $C_1$-$C_2$ alkyl. In embodiments, $R^1$ is unsubstituted $C_1$-$C_2$ alkyl. In embodiments, $R^1$ is $R^{1E}$-substituted or unsubstituted ethyl. In embodiments, $R^1$ is $R^{1E}$-substituted ethyl. In embodiments, $R^1$ is unsubstituted ethyl. In embodiments, $R^1$ is $R^{1E}$-substituted or unsubstituted methyl. In embodiments, $R^1$ is $R^{1E}$-substituted methyl. In embodiments, $R^1$ is unsubstituted methyl.

$R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1E}$-substituted or unsubstituted alkyl (e.g., $C_1$-$C_8$, $C_1$-$C_6$, or $C_1$-$C_4$ alkyl), $R^{1E}$-substituted or unsubstituted heteroalkyl (e.g., 2 to 8 membered, 2 to 6 membered, or 2 to 4 membered heteroalkyl), $R^{1E}$-substituted or unsubstituted cycloalkyl (e.g., $C_3$-$C_5$, $C_3$-$C_6$, or $C_5$-$C_6$ cycloalkyl), $R^{1E}$-substituted or unsubstituted heterocycloalkyl (e.g., 3 to 8 membered, 3 to 6 membered, or 5 to 6 membered heterocycloalkyl), $R^{1E}$-substituted or unsubstituted aryl (e.g., $C_6$-$C_{10}$, $C_{10}$ aryl, or phenyl), or $R^{1E}$-substituted or unsubstituted heteroaryl (e.g., 5 to 10 membered, 5 to 9 membered, or 5 to 6 membered heteroaryl). In embodiments, $R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{1E}$-substituted alkyl (e.g., $C_1$-$C_8$, $C_1$-$C_6$, or $C_1$-$C_4$ alkyl), $R^{1E}$-substituted heteroalkyl (e.g., 2 to 8 membered, 2 to 6 membered, or 2 to 4 membered heteroalkyl), $R^{1F}$-substituted cycloalkyl (e.g., $C_3$-$C_5$, $C_3$-$C_6$, or $C_5$-$C_6$ cycloalkyl), $R^{1F}$-substituted heterocycloalkyl (e.g., 3 to 8 membered, 3 to 6 membered, or 5 to 6 membered heterocycloalkyl), $R^{1F}$-substituted aryl (e.g., $C_6$-$C_{10}$, $C_{10}$ aryl, or phenyl), or $R^{1F}$-substituted heteroaryl (e.g., 5 to 10 membered, 5 to 9 membered, or 5 to 6 membered heteroaryl). In embodiments, $R^{1E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^2$ is hydrogen, or substituted (e.g., substituted with a substituent group, a size-limited substituent group, or lower substituent group) or unsubstituted alkyl (e.g., $C_1$-$C_{10}$, $C_1$-$C_8$, $C_1$-$C_6$, $C_1$-$C_4$, or $C_1$-$C_2$). In embodiments, $R^2$ is hydrogen, or substituted (e.g., substituted with a substituent group, a size-limited substituent group, or lower substituent group) alkyl (e.g., $C_1$-$C_{10}$, $C_1$-$C_8$, $C_1$-$C_6$, $C_1$-$C_4$, or $C_1$-$C_2$). In embodiments, $R^2$ is hydrogen, or unsubstituted alkyl (e.g., $C_1$-$C_{10}$, $C_1$-$C_8$, $C_1$-$C_6$, $C_1$-$C_4$, or $C_1$-$C_2$). In embodiments, $R^2$ is hydrogen.

In embodiments, $R^2$ is $R^{2E}$-substituted or unsubstituted $C_1$-$C_{10}$ alkyl. In embodiments, $R^2$ is $R^{2E}$-substituted $C_1$-$C_{10}$ alkyl. In embodiments, $R^2$ is unsubstituted $C_1$-$C_{10}$ alkyl. In embodiments, $R^2$ is $R^{2E}$-substituted or unsubstituted $C_1$-$C_8$ alkyl. In embodiments, $R^2$ is $R^{2E}$-substituted $C_1$-$C_8$ alkyl. In embodiments, $R^2$ is unsubstituted $C_1$-$C_8$ alkyl. In embodiments, $R^2$ is $R^{2E}$-substituted or unsubstituted $C_1$-$C_6$ alkyl. In embodiments, $R^2$ is $R^{2E}$-substituted $C_1$-$C_6$ alkyl. In embodiments, $R^2$ is unsubstituted $C_1$-$C_6$ alkyl. In embodiments, $R^2$ is $R^{2E}$-substituted or unsubstituted $C_1$-$C_4$ alkyl. In embodiments, $R^2$ is $R^{2E}$-substituted $C_1$-$C_4$ alkyl. In embodiments, $R^2$ is unsubstituted $C_1$-$C_4$ alkyl. In embodiments, $R^2$ is $R^{2E}$-substituted or unsubstituted $C_1$-$C_2$ alkyl. In embodiments, $R^2$ is $R^{2E}$-substituted $C_1$-$C_2$ alkyl. In embodiments, $R^2$ is unsubstituted $C_1$-$C_2$ alkyl. In embodiments, $R^2$ is $R^{2E}$-substituted or unsubstituted ethyl. In embodiments, $R^2$ is $R^{2E}$-substituted ethyl. In embodiments, $R^2$ is unsubstituted ethyl. In embodiments, $R^2$ is $R^{2E}$-substituted or unsubstituted methyl. In embodiments, $R^2$ is $R^{2E}$-substituted methyl. In embodiments, $R^2$ is unsubstituted methyl.

$R^{2E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{2E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{2E}$-substituted or unsubstituted cycloalkyl (e.g., $C_3$-$C_8$, $C_3$-$C_6$, or $C_5$-$C_6$ cycloalkyl), $R^{2E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{2E}$-substituted or unsubstituted heteroaryl (e.g., 5 to 10 membered, 5 to 9 membered, or 5 to 6 membered heteroaryl). In embodiments, $R^{2E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{2E}$-substituted alkyl (e.g., $C_1$-$C_8$, $C_1$-$C_6$, or $C_1$-$C_4$ alkyl), $R^{2E}$-substituted heteroalkyl (e.g., 2 to 8 membered, 2 to 6 membered, or 2 to 4 membered heteroalkyl), $R^{2E}$-substituted cycloalkyl (e.g., $C_3$-$C_8$, $C_3$-$C_6$, or $C_5$-$C_6$ cycloalkyl), $R^{2E}$-substituted heterocycloalkyl (e.g., 3 to 8 membered, 3 to 6 membered, or 5 to 6 membered heterocycloalkyl), $R^{2E}$-substituted aryl (e.g., $C_6$-$C_{10}$, $C_{10}$ aryl, or phenyl), or $R^{2E}$-substituted heteroaryl (e.g., 5 to 10 membered, 5 to 9 membered, or 5 to 6 membered heteroaryl). In embodiments, $R^{2E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^3$ is hydrogen, or substituted (e.g., substituted with a substituent group, a size-limited substituent group, or lower substituent group) or unsubstituted alkyl (e.g., $C_1$-$C_{10}$, $C_1$-$C_8$, $C_1$-$C_6$, $C_1$-$C_4$, or $C_1$-$C_2$). In embodiments, $R^3$ is hydrogen, or substituted (e.g., substituted with a substituent group, a size-limited substituent group, or lower substituent group) alkyl (e.g., $C_1$-$C_{10}$, $C_1$-$C_8$, $C_1$-$C_6$, $C_1$-$C_4$, or $C_1$-$C_2$). In embodiments, $R^3$ is hydrogen, or unsubstituted alkyl (e.g., $C_1$-$C_{10}$, $C_1$-$C_8$, $C_1$-$C_6$, $C_1$-$C_4$, or $C_1$-$C_2$). In embodiments, $R^3$ is hydrogen.

In embodiments, $R^3$ is $R^{3E}$-substituted or unsubstituted $C_1$-$C_{10}$ alkyl. In embodiments, $R^3$ is $R^{3E}$-substituted $C_1$-$C_{10}$ alkyl. In embodiments, $R^3$ is unsubstituted $C_1$-$C_{10}$ alkyl. In embodiments, $R^3$ is $R^{3E}$-substituted or unsubstituted $C_1$-$C_8$ alkyl. In embodiments, $R^3$ is $R^{3E}$-substituted $C_1$-$C_8$ alkyl. In embodiments, $R^3$ is unsubstituted $C_1$-$C_8$ alkyl. In embodiments, $R^3$ is $R^{3E}$-substituted or unsubstituted $C_1$-$C_6$ alkyl. In embodiments, $R^3$ is $R^{3E}$-substituted $C_1$-$C_6$ alkyl. In embodiments, $R^3$ is unsubstituted $C_1$-$C_6$ alkyl. In embodiments, $R^3$ is $R^{3E}$-substituted or unsubstituted $C_1$-$C_4$ alkyl. In embodiments, $R^3$ is $R^{3E}$-substituted $C_1$-$C_4$ alkyl. In embodiments, $R^3$ is unsubstituted $C_1$-$C_4$ alkyl. In embodiments, $R^3$ is $R^{3E}$-substituted or unsubstituted $C_1$-$C_2$ alkyl. In embodiments, $R^3$ is $R^{3E}$-substituted $C_1$-$C_2$ alkyl. In embodiments, $R^3$ is unsubstituted $C_1$-$C_2$ alkyl. In embodiments, $R^3$ is $R^{3E}$-substituted or unsubstituted ethyl. In embodiments, $R^3$ is $R^{3E}$-substituted ethyl. In embodiments, $R^3$ is unsubstituted ethyl. In embodiments, $R^3$ is $R^{3E}$-substituted or unsubstituted methyl. In embodiments, $R^3$ is $R^{3E}$-substituted methyl. In embodiments, $R^3$ is unsubstituted methyl.

$R^{3E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{3E}$-substituted or unsubstituted alkyl (e.g., $C_1$-$C_8$, $C_1$-$C_6$, or $C_1$-$C_4$ alkyl), $R^{3E}$-substituted or unsubstituted heteroalkyl (e.g., 2 to 8 membered, 2 to 6 membered, or 2 to 4 membered heteroalkyl), $R^{3E}$-substituted or unsubstituted cycloalkyl (e.g., $C_3$-$C_8$, $C_3$-$C_6$, or $C_5$-$C_6$ cycloalkyl), $R^{3E}$-substituted or unsubstituted heterocycloalkyl (e.g., 3 to 8 membered, 3 to 6 membered, or 5 to 6 membered heterocycloalkyl), $R^{3E}$-substituted or unsubstituted aryl (e.g., $C_6$-$C_{10}$, $C_{10}$ aryl, or phenyl), or $R^{3E}$-substituted or unsubstituted heteroaryl (e.g., 5 to 10 membered, 5 to 9 membered, or 5 to 6 membered heteroaryl). In embodiments, $R^{3E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{3F}$-substituted alkyl (e.g., $C_1$-$C_8$, $C_1$-$C_6$, or $C_1$-$C_4$ alkyl), $R^{3F}$-substituted heteroalkyl (e.g., 2 to 8 membered, 2 to 6 membered, or 2 to 4 membered heteroalkyl), $R^{3F}$-substituted cycloalkyl (e.g., $C_3$-$C_8$, $C_3$-$C_6$, or $C_5$-$C_6$ cycloalkyl), $R^{3F}$-substituted heterocycloalkyl (e.g., 3 to 8 membered, 3 to 6 membered, or 5 to 6 membered heterocycloalkyl), $R^{3F}$-substituted aryl (e.g., $C_6$-$C_{10}$, $C_{10}$ aryl, or phenyl), or $R^{3F}$-substituted heteroaryl (e.g., 5 to 10 membered, 5 to 9 membered, or 5 to 6 membered heteroaryl). In embodiments, $R^{3F}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_3$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^4$ is hydrogen, or substituted (e.g., substituted with a substituent group, a size-limited substituent group, or lower substituent group) or unsubstituted alkyl (e.g., $C_1$-$C_{10}$, $C_1$-$C_8$, $C_1$-$C_6$, $C_1$-$C_4$, or $C_1$-$C_2$). In embodiments, $R^4$ is hydrogen, or substituted (e.g., substituted with a substituent group, a size-limited substituent group, or lower substituent group) alkyl (e.g., $C_1$-$C_{10}$, $C_1$-$C_8$, $C_1$-$C_6$, $C_1$-$C_4$, or $C_1$-$C_2$). In embodiments, $R^4$ is hydrogen, or unsubstituted alkyl (e.g., $C_1$-$C_{10}$, $C_1$-$C_8$, $C_1$-$C_6$, $C_1$-$C_4$, or $C_1$-$C_2$). In embodiments, $R^4$ is hydrogen.

In embodiments, $R^4$ is $R^{4F}$-substituted or unsubstituted $C_1$-$C_{10}$ alkyl. In embodiments, $R^4$ is $R^{4F}$-substituted $C_1$-$C_{10}$ alkyl. In embodiments, $R^4$ is unsubstituted $C_1$-$C_{10}$ alkyl. In embodiments, $R^4$ is $R^{4F}$-substituted or unsubstituted $C_1$-$C_8$ alkyl. In embodiments, $R^4$ is $R^{4F}$-substituted $C_1$-$C_8$ alkyl. In embodiments, $R^4$ is unsubstituted $C_1$-$C_8$ alkyl. In embodiments, $R^4$ is $R^{4E}$-substituted or unsubstituted $C_1$-$C_6$ alkyl. In embodiments, $R^4$ is $R^{4E}$-substituted $C_1$-$C_6$ alkyl. In embodiments, $R^4$ is unsubstituted $C_1$-$C_6$ alkyl. In embodiments, $R^4$ is $R^{4E}$-substituted or unsubstituted $C_1$-$C_4$ alkyl. In embodiments, $R^4$ is $R^{4E}$-substituted $C_1$-$C_4$ alkyl. In embodiments, $R^4$ is unsubstituted $C_1$-$C_4$ alkyl. In embodiments, $R^4$ is $R^{4E}$-substituted or unsubstituted $C_1$-$C_2$ alkyl. In embodiments, $R^4$ is $R^{4E}$-substituted $C_1$-$C_2$ alkyl. In embodiments, $R^4$ is unsubstituted $C_1$-$C_2$ alkyl. In embodiments, $R^4$ is $R^{4E}$-substituted or unsubstituted ethyl. In embodiments, $R^4$ is $R^{4E}$-substituted ethyl. In embodiments, $R^4$ is unsubstituted ethyl. In embodiments, $R^4$ is $R^{4E}$-substituted or unsubstituted methyl. In embodiments, $R^4$ is $R^{4E}$-substituted methyl. In embodiments, $R^4$ is unsubstituted methyl.

$R^{4E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{4E}$-substituted or unsubstituted alkyl (e.g., $C_1$-$C_8$, $C_1$-$C_6$, or $C_1$-$C_4$ alkyl), $R^{4E}$-substituted or unsubstituted heteroalkyl (e.g., 2 to 8 membered, 2 to 6 membered, or 2 to 4 membered heteroalkyl), $R^{4E}$-substituted or unsubstituted cycloalkyl (e.g., $C_3$-$C_8$, $C_3$-$C_6$, or $C_5$-$C_6$ cycloalkyl), $R^{4E}$-substituted or unsubstituted heterocycloalkyl (e.g., 3 to 8 membered, 3 to 6 membered, or 5 to 6 membered heterocycloalkyl), $R^{4E}$-substituted or unsubstituted aryl (e.g., $C_6$-$C_{10}$, $C_{10}$ aryl, or phenyl), or $R^{4E}$-substituted or unsubstituted heteroaryl (e.g., 5 to 10 membered, 5 to 9 membered, or 5 to 6 membered heteroaryl). In embodiments, $R^{4E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{4E}$-substituted alkyl (e.g., $C_1$-$C_8$, $C_1$-$C_6$, or $C_1$-$C_4$ alkyl), $R^{4E}$-substituted heteroalkyl (e.g., 2 to 8 membered, 2 to 6 membered, or 2 to 4 membered heteroalkyl), $R^{4E}$-substituted cycloalkyl (e.g., $C_3$-$C_8$, $C_3$-$C_6$, or $C_5$-$C_6$ cycloalkyl), $R^{4E}$-substituted heterocycloalkyl (e.g., 3 to 8 membered, 3 to 6 membered, or 5 to 6 membered heterocycloalkyl), $R^{4E}$-substituted aryl (e.g., $C_6$-$C_{10}$, $C_{10}$ aryl, or phenyl), or $R^{4E}$-substituted heteroaryl (e.g., 5 to 10 membered, 5 to 9 membered, or 5 to 6 membered heteroaryl). In embodiments, $R^{4E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^5$ is hydrogen, or substituted (e.g., substituted with a substituent group, a size-limited substituent group, or lower substituent group) or unsubstituted alkyl (e.g., $C_1$-$C_{10}$, $C_1$-$C_8$, $C_1$-$C_6$, $C_1$-$C_4$, or $C_1$-$C_2$). In embodiments, $R^5$ is hydrogen, or substituted (e.g., substituted with a substituent group, a size-limited substituent group, or lower substituent group) alkyl (e.g., $C_1$-$C_{10}$, $C_1$-$C_8$, $C_1$-$C_6$, $C_1$-$C_4$, or $C_1$-$C_2$). In embodiments, $R^5$ is hydrogen, or unsubstituted alkyl (e.g., $C_1$-$C_{10}$, $C_1$-$C_8$, $C_1$-$C_6$, $C_1$-$C_4$, or $C_1$-$C_2$). In embodiments, $R^5$ is hydrogen.

In embodiments, $R^5$ is $R^{5E}$-substituted or unsubstituted $C_1$-$C_{10}$ alkyl. In embodiments, $R^5$ is $R^{5E}$-substituted $C_1$-$C_{10}$ alkyl. In embodiments, $R^5$ is unsubstituted $C_1$-$C_{10}$ alkyl. In embodiments, $R^5$ is $R^{5E}$-substituted or unsubstituted $C_1$-$C_8$ alkyl. In embodiments, $R^5$ is $R^{5E}$-substituted $C_1$-$C_8$ alkyl. In embodiments, $R^5$ is unsubstituted $C_1$-$C_8$ alkyl. In embodiments, $R^5$ is $R^{5E}$-substituted or unsubstituted $C_1$-$C_6$ alkyl. In embodiments, $R^5$ is $R^{5E}$-substituted $C_1$-$C_6$ alkyl. In embodiments, $R^5$ is unsubstituted $C_1$-$C_6$ alkyl. In embodiments, $R^5$ is $R^{5E}$-substituted or unsubstituted $C_1$-$C_4$ alkyl. In embodiments, $R^5$ is $R^{5E}$-substituted $C_1$-$C_4$ alkyl. In embodiments, $R^5$ is unsubstituted $C_1$-$C_4$ alkyl. In embodiments, $R^5$ is $R^{5E}$-substituted or unsubstituted $C_1$-$C_2$ alkyl. In embodiments, $R^5$ is $R^{5E}$-substituted $C_1$-$C_2$ alkyl. In embodiments, $R^5$ is unsubstituted $C_1$-$C_2$ alkyl. In embodiments, $R^5$ is $R^{5E}$-substituted or unsubstituted ethyl. In embodiments, $R^5$ is $R^{5E}$-substituted ethyl. In embodiments, $R^5$ is unsubstituted ethyl. In embodiments, $R^5$ is $R^{5E}$-substituted or unsubstituted methyl. In embodiments, $R^5$ is $R^{5E}$-substituted methyl. In embodiments, $R^5$ is unsubstituted methyl.

$R^{5E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{5F}$-substituted or unsubstituted alkyl (e.g., $C_1$-$C_8$, $C_1$-$C_6$, or $C_1$-$C_4$ alkyl), $R^{5F}$-substituted or unsubstituted heteroalkyl (e.g., 2 to 8 membered, 2 to 6 membered, or 2 to 4 membered heteroalkyl), $R^{5F}$-substituted or unsubstituted cycloalkyl (e.g., $C_3$-$C_5$, $C_3$-$C_6$, or $C_5$-$C_6$ cycloalkyl), $R^{5F}$-substituted or unsubstituted heterocycloalkyl (e.g., 3 to 8 membered, 3 to 6 membered, or 5 to 6 membered heterocycloalkyl), $R^{5F}$-substituted or unsubstituted aryl (e.g., $C_6$-$C_{10}$, $C_{10}$ aryl, or phenyl), or $R^{5F}$-substituted or unsubstituted heteroaryl (e.g., 5 to 10 membered, 5 to 9 membered, or 5 to 6 membered heteroaryl). In embodiments, $R^{5E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{5F}$-substituted alkyl (e.g., $C_1$-$C_8$, $C_1$-$C_6$, or $C_1$-$C_4$ alkyl), $R^{5F}$-substituted heteroalkyl (e.g., 2 to 8 membered, 2 to 6 membered, or 2 to 4 membered heteroalkyl), $R^{5F}$-substituted cycloalkyl (e.g., $C_3$-$C_8$, $C_3$-$C_6$, or $C_5$-$C_6$ cycloalkyl), $R^{5F}$-substituted heterocycloalkyl (e.g., 3 to 8 membered, 3 to 6 membered, or 5 to 6 membered heterocycloalkyl), $R^{5F}$-substituted aryl (e.g., $C_6$-$C_{10}$, $C_{10}$ aryl, or phenyl), or $R^{5F}$-substituted heteroaryl (e.g., 5 to 10 membered, 5 to 9 membered, or 5 to 6 membered heteroaryl). In embodiments, $R^{5E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —OH, —$NH_2$, —COOH, —$CONH_2$, —$NO_2$, —$N_3$, —SH, —$SCH_3$, —$SO_3H$, —$SO_4H$, —$SO_2NH_2$, —$NHNH_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_5$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, R$^6$ is a substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered).

In embodiments, R$^6$ is R$^{6E}$-substituted or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{6E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), R$^{6E}$-substituted or unsubstituted cycloalkyl (e.g., C$_3$-C$_{10}$, C$_3$-C$_8$, C$_3$-C$_6$, C$_4$-C$_6$, or C$_5$-C$_6$), R$^{6E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{6E}$-substituted or unsubstituted aryl (e.g., C$_6$-C$_{12}$, C$_6$-C$_{10}$, or phenyl), or R$^{6E}$-substituted or unsubstituted heteroaryl (e.g., 5 to 12 membered, 5 to 10 membered, 5 to 9 membered, or 5 to 6 membered). In embodiments, R$^6$ is R$^{6E}$-substituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{6E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), R$^{6E}$-substituted cycloalkyl (e.g., C$_3$-C$_{10}$, C$_3$-C$_8$, C$_3$-C$_6$, C$_4$-C$_6$, or C$_5$-C$_6$), R$^{6E}$-substituted heterocycloalkyl (e.g., 3 to 10 membered, 3 to 8 membered, 3 to 6 membered, 4 to 6 membered, 4 to 5 membered, or 5 to 6 membered), R$^{6E}$-substituted aryl (e.g., C$_6$-C$_{12}$, C$_6$-C$_{10}$, or phenyl), or R$^{6E}$-substituted heteroaryl (e.g., 5 to 12 membered, 5 to 10 membered, 5 to 9 membered, or 5 to 6 membered). In embodiments, R$^6$ is unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{6E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —N$_3$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{6F}$-substituted or unsubstituted alkyl (e.g., C$_1$-C$_8$, C$_1$-C$_6$, or C$_1$-C$_4$ alkyl), R$^{6F}$-substituted or unsubstituted heteroalkyl (e.g., 2 to 8 membered, 2 to 6 membered, or 2 to 4 membered heteroalkyl), R$^{6F}$-substituted or unsubstituted cycloalkyl (e.g., C$_3$-C$_8$, C$_3$-C$_6$, or C$_5$-C$_6$ cycloalkyl), R$^{6F}$-substituted or unsubstituted heterocycloalkyl (e.g., 3 to 8 membered, 3 to 6 membered, or 5 to 6 membered heterocycloalkyl), R$^{6F}$-substituted or unsubstituted aryl (e.g., C$_6$-C$_{10}$, C$_{10}$ aryl, or phenyl), or R$^{6F}$-substituted or unsubstituted heteroaryl (e.g., 5 to 10 membered, 5 to 9 membered, or 5 to 6 membered heteroaryl). In embodiments, R$^{6F}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —N$_3$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{6F}$-substituted alkyl (e.g., C$_1$-C$_8$, C$_1$-C$_6$, or C$_1$-C$_4$ alkyl), R$^{6F}$-substituted heteroalkyl (e.g., 2 to 8 membered, 2 to 6 membered, or 2 to 4 membered heteroalkyl), R$^{6F}$-substituted cycloalkyl (e.g., C$_3$-C$_8$, C$_3$-C$_6$, or C$_5$-C$_6$ cycloalkyl), R$^{6F}$-substituted heterocycloalkyl (e.g., 3 to 8 membered, 3 to 6 membered, or 5 to 6 membered heterocycloalkyl), R$^{6F}$-substituted aryl (e.g., C$_6$-C$_{10}$, C$_{10}$ aryl, or phenyl), or R$^{6F}$-substituted heteroaryl (e.g., 5 to 10 membered, 5 to 9 membered, or 5 to 6 membered heteroaryl). In embodiments, R$^{6F}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —OH, —NH$_2$, —COOH, —CONH$_2$, —NO$_2$, —N$_3$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, L$^1$ is a substituted (e.g., substituted with a substituent group, a size-limited substituent group, or lower substituent group) or unsubstituted alkylene (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkylene (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkylene (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted arylene (e.g., $C_6$-$C_{12}$, $C_6$-$C_{10}$, or phenyl), or substituted (e.g., substituted with a substituent group, a size-limited substituent group, or lower substituent group) or unsubstituted heteroarylene (e.g., 5 to 12 membered, 5 to 10 membered, 5 to 9 membered, or 5 to 6 membered).

In embodiments, $L^1$ is a $R^{18}$-substituted or unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), $R^{18}$-substituted or unsubstituted heteroalkylene (e.g., 2 to 20 membered, 2 to 12 membered, 2 to 8 membered, 2 to 6 membered, 4 to 6 membered, 2 to 3 membered, or 4 to 5 membered), $R^{18}$-substituted or unsubstituted cycloalkylene (e.g., $C_3$-$C_{10}$, $C_3$-$C_8$, $C_3$-$C_6$, $C_4$-$C_6$, or $C_5$-$C_6$), $R^{18}$-substituted or unsubstituted heterocycloalkylene (e.g., 3 to 10 membered, 3 to 8 membered, 3 to 6 membered, 4 to 6 membered, 4 to 5 membered, or 5 to 6 membered), $R^{18}$-substituted or unsubstituted arylene (e.g., $C_6$-$C_{12}$, $C_6$-$C_{10}$, or phenyl), or $R^{18}$-substituted or unsubstituted heteroarylene (e.g., 5 to 12 membered, 5 to 10 membered, 5 to 9 membered, or 5 to 6 membered). In embodiments, $L^1$ is a $R^{18}$-substituted alkylene (e.g., $C_1$-$C_{20}$, $C_1$-$C_{12}$, $C_1$-$C_8$, $C_1$-$C_6$, $C_1$-$C_4$, or $C_1$-$C_2$), $R^{18}$-substituted heteroalkylene (e.g., 2 to 20 membered, 2 to 12 membered, 2 to 8 membered, 2 to 6 membered, 4 to 6 membered, 2 to 3 membered, or 4 to 5 membered), $R^{18}$-substituted cycloalkylene (e.g., $C_3$-$C_{10}$, $C_3$-$C_8$, $C_3$-$C_6$, $C_4$-$C_6$, or $C_5$-$C_6$), $R^{18}$-substituted heterocycloalkylene (e.g., 3 to 10 membered, 3 to 8 membered, 3 to 6 membered, 4 to 6 membered, 4 to 5 membered, or 5 to 6 membered), $R^{18}$-substituted arylene (e.g., $C_6$-$C_{12}$, $C_6$-$C_{10}$, or phenyl), or $R^{18}$-substituted heteroarylene (e.g., 5 to 12 membered, 5 to 10 membered, 5 to 9 membered, or 5 to 6 membered). In embodiments, $L^1$ is unsubstituted alkylene (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkylene (e.g., 2 to 20 membered, 2 to 12 membered, 2 to 8 membered, 2 to 6 membered, 4 to 6 membered, 2 to 3 membered, or 4 to 5 membered), unsubstituted cycloalkylene (e.g., $C_3$-$C_{10}$, $C_3$-$C_8$, $C_3$-$C_6$, $C_4$-$C_6$, or $C_5$-$C_6$), unsubstituted heterocycloalkylene (e.g., 3 to 10 membered, 3 to 8 membered, 3 to 6 membered, 4 to 6 membered, 4 to 5 membered, or 5 to 6 membered), unsubstituted arylene (e.g., $C_6$-$C_{12}$, $C_6$-$C_{10}$, or phenyl), or unsubstituted heteroarylene (e.g., 5 to 12 membered, 5 to 10 membered, 5 to 9 membered, or 5 to 6 membered).

$R^{18}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{19}$— substituted or unsubstituted alkyl (e.g., $C_1$-$C_8$, $C_1$-$C_6$, or $C_1$-$C_4$ alkyl), $R^{19}$-substituted or unsubstituted heteroalkyl (e.g., 2 to 8 membered, 2 to 6 membered, or 2 to 4 membered heteroalkyl), $R^{19}$-substituted or unsubstituted cycloalkyl (e.g., $C_3$-$C_8$, $C_3$-$C_6$, or $C_5$-$C_6$ cycloalkyl), $R^{19}$-substituted or unsubstituted heterocycloalkyl (e.g., 3 to 8 membered, 3 to 6 membered, or 5 to 6 membered heterocycloalkyl), $R^{19}$-substituted or unsubstituted aryl (e.g., $C_6$-$C_{10}$, $C_{10}$ aryl, or phenyl), or $R^{19}$-substituted or unsubstituted heteroaryl (e.g., 5 to 10 membered, 5 to 9 membered, or 5 to 6 membered heteroaryl). In embodiments, $R^{18}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{19}$-substituted alkyl (e.g., $C_1$-$C_8$, $C_1$-$C_6$, or $C_1$-$C_4$ alkyl), $R^{19}$-substituted heteroalkyl (e.g., 2 to 8 membered, 2 to 6 membered, or 2 to 4 membered heteroalkyl), $R^{19}$-substituted cycloalkyl (e.g., $C_3$-$C_8$, $C_3$-$C_6$, or $C_5$-$C_6$ cycloalkyl), $R^{19}$-substituted heterocycloalkyl (e.g., 3 to 8 membered, 3 to 6 membered, or 5 to 6 membered heterocycloalkyl), $R^{19}$-substituted aryl (e.g., $C_6$-$C_{10}$, $C_{10}$ aryl, or phenyl), or $R^{19}$-substituted heteroaryl (e.g., 5 to 10 membered, 5 to 9 membered, or 5 to 6 membered heteroaryl). In embodiments, $R^{18}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{24}$ is hydrogen, —$CX_3$ (e.g., —$CF_3$, —$CCl_3$, —$CBr_3$, or —$CI_3$), —$CHX_2$ (—$CHF_2$, —$CHCl_2$, —$CHBr_2$, or —$CHI_2$), —$CH_2X$ (e.g., —$CH_2F$, —$CH_2Cl$, —$CH_2Br$, or —$CH_2I$), —COOH, —$CONH_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). X is —F, —Cl, —Br, or —I.

In embodiments, $R^{2A}$ is hydrogen, —$CF_3$, —$CCl_3$, —$CBr_3$, —$CI_3$, —$CHF_2$, —$CHCl_2$, —$CHBr_2$, —$CHI_2$, —$CH_{2F}$, —$CH_2Cl$, —$CH_2Br$, —$CH_2I$, —COOH, —$CONH_2$, $R^{2E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{2E}$-substituted or unsubstituted cycloalkyl (e.g., $C_3$-$C_8$, $C_3$-$C_6$, or $C_5$-$C_6$ cycloalkyl), $R^{2E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{2E}$-substituted or unsubstituted heteroaryl (e.g., 5 to 10 membered, 5 to 9 membered, or 5 to 6 membered heteroaryl). In embodiments, $R^{2A}$ is hydrogen, —$CF_3$, —$CCl_3$, —$CBr_3$, —$CI_3$, —$CHF_2$, —$CHCl_2$, —$CHBr_2$, —$CHI_2$, —$CH_{2F}$, —$CH_2Cl$, —$CH_2Br$, —$CH_2I$, —COOH, —$CONH_2$, $R^{2E}$-substituted alkyl (e.g., $C_1$-$C_8$, $C_1$-$C_6$, or $C_1$-$C_4$ alkyl), $R^{2E}$-substituted heteroalkyl (e.g., 2 to 8 membered, 2 to 6 membered, or 2 to 4 membered heteroalkyl), $R^{2E}$-substituted cycloalkyl (e.g., $C_3$-$C_8$, $C_3$-$C_6$, or $C_5$-$C_6$ cycloalkyl), $R^{2E}$-substituted heterocycloalkyl (e.g., 3 to 8 membered, 3 to 6 membered, or 5 to 6 membered heterocycloalkyl), $R^{2E}$-substituted aryl (e.g., $C_6$-$C_{10}$, $C_{10}$ aryl, or phenyl), or $R^{2E}$-substituted heteroaryl (e.g., 5 to 10 membered, 5 to 9 membered, or 5 to 6 membered heteroaryl). In embodiments, $R^{2A}$ is hydrogen, —$CF_3$, —$CCl_3$, —$CBr_3$, —$CI_3$, —$CHF_2$, —$CHCl_2$, —$CHBr_2$, —$CHI_2$, —$CH_{2F}$, —$CH_2Cl$, —$CH_2Br$, —$CH_2I$, —COOH, —$CONH_2$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_3$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{2B}$ is hydrogen, —$CX_3$ (e.g., —$CF_3$, —$CCl_3$, —$CBr_3$, or —$CI_3$), —$CHX_2$ (—$CHF_2$, —$CHCl_2$, —$CHBr_2$, or —$CHI_2$), —$CH_2X$ (e.g., —$CH_2F$, —$CH_2Cl$, —$CH_2Br$, or —$CH_2I$), —COOH, —$CONH_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_3$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). X is —F, —Cl, —Br, or —I.

In embodiments, $R^{2B}$ is hydrogen, —$CF_3$, —$CCl_3$, —$CBr_3$, —$CI_3$, —$CHF_2$, —$CHCl_2$, —$CHBr_2$, —$CHI_2$, —$CH_{2E}$, —$CH_2Cl$, —$CH_2Br$, —$CH_2I$, —COOH, —$CONH_2$, $R^{2E}$-substituted or unsubstituted alkyl (e.g., $C_1$-$C_8$, $C_1$-$C_6$, or $C_1$-$C_4$ alkyl), $R^{2E}$-substituted or unsubstituted heteroalkyl (e.g., 2 to 8 membered, 2 to 6 membered, or 2 to 4 membered heteroalkyl), $R^{2E}$-substituted or unsubstituted cycloalkyl (e.g., $C_3$-$C_8$, $C_3$-$C_6$, or $C_5$-$C_6$ cycloalkyl), $R^{2E}$-substituted or unsubstituted heterocycloalkyl (e.g., 3 to 8 membered, 3 to 6 membered, or 5 to 6 membered heterocycloalkyl), $R^{2E}$-substituted or unsubstituted aryl (e.g., $C_6$-$C_{10}$, $C_{10}$ aryl, or phenyl), or $R^{2E}$-substituted or unsubstituted heteroaryl (e.g., 5 to 10 membered, 5 to 9 membered, or 5 to 6 membered heteroaryl). In embodiments, $R^{2B}$ is hydrogen, —$CF_3$, —$CCl_3$, —$CBr_3$, —$CI_3$, —$CHF_2$, —$CHCl_2$, —$CHBr_2$, —$CHI_2$, —$CH_{2E}$, —$CH_2Cl$, —$CH_2Br$, —$CH_2I$, —COOH, —$CONH_2$, $R^{2E}$-substituted alkyl (e.g., $C_1$-$C_8$, $C_1$-$C_6$, or $C_1$-$C_4$ alkyl), $R^{2E}$-substituted heteroalkyl (e.g., 2 to 8 membered, 2 to 6 membered, or 2 to 4 membered heteroalkyl), $R^{2E}$-substituted cycloalkyl (e.g., $C_3$-$C_8$, $C_3$-$C_6$, or $C_5$-$C_6$ cycloalkyl), $R^{2E}$-substituted heterocycloalkyl (e.g., 3 to 8 membered, 3 to 6 membered, or 5 to 6 membered heterocycloalkyl), $R^{2E}$-substituted aryl (e.g., $C_6$-$C_{10}$, $C_{10}$ aryl, or phenyl), or $R^{2E}$-substituted heteroaryl (e.g., 5 to 10 membered, 5 to 9 membered, or 5 to 6 membered heteroaryl). In embodiments, $R^{2B}$ is hydrogen, —$CF_3$, —$CCl_3$, —$CBr_3$, —$CI_3$, —$CHF_2$, —$CHCl_2$, —$CHBr_2$, —$CHI_2$, —$CH_{2E}$, —$CH_2Cl$, —$CH_2Br$, —$CH_2I$, —COOH, —$CONH_2$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^7$ is hydrogen, halogen (e.g., —F, —Cl, —Br, —I), —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —NHC(O)$NR^{7A}R^{7B}$, —N(O)$_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n7 is an integer from 0 to 4 (e.g. 0). m7 and v7 are independently an integer from 1 to 2. $X^7$ is independently —F, —Cl, —Br, or —I.

In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{7E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{7E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{7E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{7E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{7E}$-substituted or unsubstituted aryl (e.g., $C_6$-$C_{12}$, $C_6$-$C_{10}$, or phenyl), or $R^{7E}$-substituted or unsubstituted heteroaryl (e.g., 5 to 12 membered, 5 to 10 membered, 5 to 9 membered, or 5 to 6 membered). In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{7E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{7E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{7E}$-substituted cycloalkyl (e.g., $C_3$-$C_{10}$, $C_3$-$C_3$, $C_3$-$C_6$, $C_4$-$C_6$, or $C_5$-$C_6$), $R^{7E}$-substituted heterocycloalkyl (e.g., 3 to 10 membered, 3 to 8 membered, 3 to 6 membered, 4 to 6 membered, 4 to 5 membered, or 5 to 6 membered), $R^{7E}$-substituted aryl (e.g., $C_6$-$C_{12}$, $C_6$-$C_{10}$, or phenyl), or $R^{7E}$-substituted heteroaryl (e.g., 5 to 12 membered, 5 to 10 membered, 5 to 9 membered, or 5 to 6 membered). In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{7F}$-substituted or unsubstituted alkyl (e.g., $C_1$-$C_8$, $C_1$-$C_6$, or $C_1$-$C_4$ alkyl), $R^{7F}$-substituted or unsubstituted heteroalkyl (e.g., 2 to 8 membered, 2 to 6 membered, or 2 to 4 membered heteroalkyl), $R^{7F}$-substituted or unsubstituted cycloalkyl (e.g., $C_3$-$C_8$, $C_3$-$C_6$, or $C_5$-$C_6$ cycloalkyl), $R^{7F}$-substituted or unsubstituted heterocycloalkyl (e.g., 3 to 8 membered, 3 to 6 membered, or 5 to 6 membered heterocycloalkyl), $R^{7F}$-substituted or unsubstituted aryl (e.g., $C_6$-$C_{10}$, $C_{10}$ aryl, or phenyl), or $R^{7F}$-substituted or unsubstituted heteroaryl (e.g., 5 to 10 membered, 5 to 9 membered, or 5 to 6 membered heteroaryl). In embodiments, $R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{7F}$-substituted alkyl (e.g., $C_1$-$C_8$, $C_1$-$C_6$, or $C_1$-$C_4$ alkyl), $R^{7F}$-substituted heteroalkyl (e.g., 2 to 8 membered, 2 to 6 membered, or 2 to 4 membered heteroalkyl), $R^{7F}$-substituted cycloalkyl (e.g., $C_3$-$C_8$, $C_3$-$C_6$, or $C_5$-$C_6$ cycloalkyl), $R^{7F}$-substituted heterocycloalkyl (e.g., 3 to 8 membered, 3 to 6 membered, or 5 to 6 membered heterocycloalkyl), $R^{7F}$-substituted aryl (e.g., $C_6$-$C_{10}$, $C_{10}$ aryl, or phenyl), or $R^{7F}$-substituted heteroaryl (e.g., 5 to 10 membered, 5 to 9 membered, or 5 to 6 membered heteroaryl). In embodiments, $R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —OCHCl₂, —OCHBr₂, —OCHI₂, —OCH₂F, —OCH₂Cl, —OCH₂Br, —OCH₂I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^8$ is hydrogen, halogen (e.g., —F, —Cl, —Br, —I), —CX$^8$₃, —CHX$^8$₂, —CH₂X$^8$, —OCX$^8$₃, —OCH₂X$^8$, —OCHX$^8$₂, —N₃, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO₂R$^{8D}$, —NR$^{8A}$C(O)R$^{8C}$, —NR$^{8A}$C(O)OR$^{8C}$, —NR$^{8A}$OR$^{8C}$ (e.g., —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, or —NCH₃OCH₃), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n8 is an integer from 0 to 4 (e.g. 0). m8 and v8 are independently an integer from 1 to 2. X$^8$ is independently —F, —Cl, —Br, or —I.

In embodiments, $R^8$ is hydrogen, —F, —Cl, —Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, R$^{8E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), R$^{8E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), R$^{8E}$-substituted or unsubstituted cycloalkyl (e.g., $C_3$-$C_{10}$, $C_3$-$C_8$, $C_3$-$C_6$, $C_4$-$C_6$, or $C_5$-$C_6$), R$^{8E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{8E}$-substituted or unsubstituted aryl (e.g., $C_6$-$C_{12}$, $C_6$-$C_{10}$, or phenyl), or R$^{8E}$-substituted or unsubstituted heteroaryl (e.g., 5 to 12 membered, 5 to 10 membered, 5 to 9 membered, or 5 to 6 membered). In embodiments, $R^8$ is hydrogen, —F, —Cl, —Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, R$^{8E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), R$^{8E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), R$^{8E}$-substituted cycloalkyl (e.g., $C_3$-$C_{10}$, $C_3$-$C_3$, $C_3$-$C_6$, $C_4$-$C_6$, or $C_5$-$C_6$), R$^{8E}$-substituted heterocycloalkyl (e.g., 3 to 10 membered, 3 to 8 membered, 3 to 6 membered, 4 to 6 membered, 4 to 5 membered, or 5 to 6 membered), R$^{8E}$-substituted aryl (e.g., $C_6$-$C_{12}$, $C_6$-$C_{10}$, or phenyl), or R$^{8E}$-substituted heteroaryl (e.g., 5 to 12 membered, 5 to 10 membered, 5 to 9 membered, or 5 to 6 membered). In embodiments, $R^8$ is hydrogen, —F, —Cl, —Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

R$^{8E}$ is independently oxo, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —OH, —NH₂, —COOH, —CONH₂, —NO₂, —SH, —SCH₃, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, $R^{8F}$-substituted or unsubstituted alkyl (e.g., $C_1$-$C_8$, $C_1$-$C_6$, or $C_1$-$C_4$ alkyl), $R^{8F}$-substituted or unsubstituted heteroalkyl (e.g., 2 to 8 membered, 2 to 6 membered, or 2 to 4 membered heteroalkyl), $R^{8F}$-substituted or unsubstituted cycloalkyl (e.g., $C_3$-$C_8$, $C_3$-$C_6$, or $C_5$-$C_6$ cycloalkyl), $R^{8F}$-substituted or unsubstituted heterocycloalkyl (e.g., 3 to 8 membered, 3 to 6 membered, or 5 to 6 membered heterocycloalkyl), $R^{8F}$-substituted or unsubstituted aryl (e.g., $C_6$-$C_{10}$, $C_{10}$ aryl, or phenyl), or $R^{8F}$-substituted or unsubstituted heteroaryl (e.g., 5 to 10 membered, 5 to 9 membered, or 5 to 6 membered heteroaryl). In embodiments, $R^{8F}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{8F}$-substituted alkyl (e.g., $C_1$-$C_8$, $C_1$-$C_6$, or $C_1$-$C_4$ alkyl), $R^{8F}$-substituted heteroalkyl (e.g., 2 to 8 membered, 2 to 6 membered, or 2 to 4 membered heteroalkyl), $R^{8F}$-substituted cycloalkyl (e.g., $C_3$-$C_8$, $C_3$-$C_6$, or $C_5$-$C_6$ cycloalkyl), $R^{8F}$-substituted heterocycloalkyl (e.g., 3 to 8 membered, 3 to 6 membered, or 5 to 6 membered heterocycloalkyl), $R^{8F}$-substituted aryl (e.g., $C_6$-$C_{10}$, $C_{10}$ aryl, or phenyl), or $R^{8F}$-substituted heteroaryl (e.g., 5 to 10 membered, 5 to 9 membered, or 5 to 6 membered heteroaryl). In embodiments, $R^{8F}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^7$ and $R^8$ together with atoms attached thereto are joined to form $R^{7E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{7E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{7E}$-substituted or unsubstituted aryl (e.g., $C_6$-$C_{12}$, $C_6$-$C_{10}$, or phenyl), or $R^{7E}$-substituted or unsubstituted heteroaryl (e.g., 5 to 12 membered, 5 to 10 membered, 5 to 9 membered, or 5 to 6 membered). In embodiments, $R^7$ and $R^8$ together with atoms attached thereto are joined to form $R^{7E}$-substituted cycloalkyl (e.g., $C_3$-$C_{10}$, $C_3$-$C_3$, $C_3$-$C_6$, $C_4$-$C_6$, or $C_5$-$C_6$), $R^{7E}$-substituted heterocycloalkyl (e.g., 3 to 10 membered, 3 to 8 membered, 3 to 6 membered, 4 to 6 membered, 4 to 5 membered, or 5 to 6 membered), $R^{7E}$-substituted aryl (e.g., $C_6$-$C_{12}$, $C_6$-$C_{10}$, or phenyl), or $R^{7E}$-substituted heteroaryl (e.g., 5 to 12 membered, 5 to 10 membered, 5 to 9 membered, or 5 to 6 membered). In embodiments, $R^7$ and $R^8$ together with atoms attached thereto are joined to form unsubstituted cycloalkyl (e.g., $C_3$-$C_{10}$, $C_3$-$C_3$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^9$ is hydrogen, halogen (e.g., —F, —Cl, —Br, —I), —$CX^9_3$, —$CHX^9_2$, —$CH_2X^9$, —$OCX^9_3$, —$OCH_2X^9$, —$OCHX^9_2$, —$N_3$, —CN, —$SO_{n9}R^{9D}$, —$SO_{v9}NR^{9A}R^{9B}$, —$NHC(O)NR^{9A}R^{9B}$, —$N(O)_{m9}$, —$NR^{9A}$, $R^{9B}$, —$C(O)R^{9C}$, —$C(O)$—$OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n9 is an integer from 0 to 4 (e.g. 0). m9 and v9 are independently an integer from 1 to 2. $X^9$ is independently —F, —Cl, —Br, or —I.

In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, $R^{9E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{9E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{9E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{9E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{9E}$-substituted or unsubstituted aryl (e.g., $C_6$-$C_{12}$, $C_6$-$C_{10}$, or phenyl), or $R^{9E}$-substituted or unsubstituted heteroaryl (e.g., 5 to 12 membered, 5 to 10 membered, 5 to 9 membered, or 5 to 6 membered). In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{9E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{9E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{9E}$-substituted cycloalkyl (e.g., $C_3$-$C_{10}$, $C_3$-$C_5$, $C_3$-$C_6$, $C_4$-$C_6$, or $C_5$-$C_6$), $R^{9E}$-substituted heterocycloalkyl (e.g., 3 to 10 membered, 3 to 8 membered, 3 to 6 membered, 4 to 6 membered, 4 to 5 membered, or 5 to 6 membered), $R^{9E}$-substituted aryl (e.g., $C_6$-$C_{12}$, $C_6$-$C_{10}$, or phenyl), or $R^{9E}$-substituted heteroaryl (e.g., 5 to 12 membered, 5 to 10 membered, 5 to 9 membered, or 5 to 6 membered). In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{9E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{9E}$-substituted or unsubstituted alkyl (e.g., $C_1$-$C_8$, $C_1$-$C_6$, or $C_1$-$C_4$ alkyl), $R^{9E}$-substituted or unsubstituted heteroalkyl (e.g., 2 to 8 membered, 2 to 6 membered, or 2 to 4 membered heteroalkyl), $R^{9E}$-substituted or unsubstituted cycloalkyl (e.g., $C_3$-$C_8$, $C_3$-$C_6$, or $C_5$-$C_6$ cycloalkyl), $R^{9E}$-substituted or unsubstituted heterocycloalkyl (e.g., 3 to 8 membered, 3 to 6 membered, or 5 to 6 membered heterocycloalkyl), $R^{9E}$-substituted or unsubstituted aryl (e.g., $C_6$-$C_{10}$, $C_{10}$ aryl, or phenyl), or $R^{9E}$-substituted or unsubstituted heteroaryl (e.g., 5 to 10 membered, 5 to 9 membered, or 5 to 6 membered heteroaryl). In embodiments, $R^{9F}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{9F}$-substituted alkyl (e.g., $C_1$-$C_8$, $C_1$-$C_6$, or $C_1$-$C_4$ alkyl), $R^{9F}$-substituted heteroalkyl (e.g., 2 to 8 membered, 2 to 6 membered, or 2 to 4 membered heteroalkyl), $R^{9F}$-substituted cycloalkyl (e.g., $C_3$-$C_8$, $C_3$-$C_6$, or $C_5$-$C_6$ cycloalkyl), $R^{9F}$-substituted heterocycloalkyl (e.g., 3 to 8 membered, 3 to 6 membered, or 5 to 6 membered heterocycloalkyl), $R^{9F}$-substituted aryl (e.g., $C_6$-$C_{10}$, $C_{10}$ aryl, or phenyl), or $R^{9F}$-substituted heteroaryl (e.g., 5 to 10 membered, 5 to 9 membered, or 5 to 6 membered heteroaryl). In embodiments, $R^{9F}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^8$ and $R^9$ together with atoms attached thereto are joined to form $R^{8F}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{8F}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{8F}$-substituted or unsubstituted aryl (e.g., $C_6$-$C_{12}$, $C_6$-$C_{10}$, or phenyl), or $R^{8F}$-substituted or unsubstituted heteroaryl (e.g., 5 to 12 membered, 5 to 10 membered, 5 to 9 membered, or 5 to 6 membered). In embodiments, $R^8$ and $R^9$ together with atoms attached thereto are joined to form $R^{8F}$-substituted cycloalkyl (e.g., $C_3$-$C_{10}$, $C_3$-$C_8$, $C_3$-$C_6$, $C_4$-$C_6$, or $C_5$-$C_6$), $R^{8F}$-substituted heterocycloalkyl (e.g., 3 to 10 membered, 3 to 8 membered, 3 to 6 membered, 4 to 6 membered, 4 to 5 membered, or 5 to 6 membered), $R^{8F}$-substituted aryl (e.g., $C_6$-$C_{12}$, $C_6$-$C_{10}$, or phenyl), or $R^{8F}$-substituted heteroaryl (e.g., 5 to 12 membered, 5 to 10 membered, 5 to 9 membered, or 5 to 6 membered). In embodiments, $R^8$ and $R^9$ together with atoms attached thereto are joined to form unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

In embodiments, $R^{10}$ is hydrogen, halogen (e.g., —F, —Cl, —Br, —I), —$CX^{10}_3$, —$CHX^{10}_2$, —$CH_2X^{10}$, —$OCX^{10}_3$, —$OCH_2X^{10}$, —$OCHX^{10}_2$, —$N_3$, —CN, —$SO_{n10}R^{100}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_3$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n10 is an integer from 0 to 4 (e.g. 0). m10 and v10 are independently an integer from 1 to 2. $X^{10}$ is independently —F, —Cl, —Br, or —I.

In embodiments, $R^{10}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, $R^{10E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{10E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{10E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{10E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{10E}$-substituted or unsubstituted aryl (e.g., $C_6$-$C_{12}$, $C_6$-$C_{10}$, or phenyl), or $R^{10E}$-substituted or unsubstituted heteroaryl (e.g., 5 to 12 membered, 5 to 10 membered, 5 to 9 membered, or 5 to 6 membered). In embodiments, $R^{10}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, $R^{10E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{10E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{10E}$-substituted cycloalkyl (e.g., $C_3$-$C_{10}$, $C_3$-$C_8$, $C_3$-$C_6$, $C_4$-$C_6$, or $C_5$-$C_6$), $R^{10E}$-substituted heterocycloalkyl (e.g., 3 to 10 membered, 3 to 8 membered, 3 to 6 membered, 4 to 6 membered, 4 to 5 membered, or 5 to 6 membered), $R^{10E}$-substituted aryl (e.g., $C_6$-$C_{12}$, $C_6$-$C_{10}$, or phenyl), or $R^{10E}$-substituted heteroaryl (e.g., 5 to 12 membered, 5 to 10 membered, 5 to 9 membered, or 5 to 6 membered). In embodiments, $R^{10}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —$C(O)H$, —$C(O)CH_3$, —$C(O)OH$, —$C(O)OCH_3$, —$C(O)NH_2$, —$C(O)NHCH_3$, —OH, —$OCH_3$, —$NHSO_2H$, —$NHSO_2CH_3$, —$NHC(O)H$, —$NCH_3C(O)H$, —$NHC(O)OH$, —$NCH_3C(O)OH$, —NHOH, —$NCH_3OH$, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{10E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{10F}$-substituted or unsubstituted alkyl (e.g., $C_1$-$C_8$, $C_1$-$C_6$, or $C_1$-$C_4$ alkyl), $R^{10F}$-substituted or unsubstituted heteroalkyl (e.g., 2 to 8 membered, 2 to 6 membered, or 2 to 4 membered heteroalkyl), $R^{10F}$-substituted or unsubstituted cycloalkyl (e.g., $C_3$-$C_8$, $C_3$-$C_6$, or $C_5$-$C_6$ cycloalkyl), $R^{10F}$-substituted or unsubstituted heterocycloalkyl (e.g., 3 to 8 membered, 3 to 6 membered, or 5 to 6 membered heterocycloalkyl), $R^{10F}$-substituted or unsubstituted aryl (e.g., $C_6$-$C_{10}$, $C_{10}$ aryl, or phenyl), or $R^{10F}$-substituted or unsubstituted heteroaryl (e.g., 5 to 10 membered, 5 to 9 membered, or 5 to 6 membered heteroaryl). In embodiments, $R^{10F}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{10F}$-substituted alkyl (e.g., C$_1$-C$_8$, C$_1$-C$_6$, or C$_1$-C$_4$ alkyl), $R^{10F}$-substituted heteroalkyl (e.g., 2 to 8 membered, 2 to 6 membered, or 2 to 4 membered heteroalkyl), $R^{10F}$-substituted cycloalkyl (e.g., C$_3$-C$_8$, C$_3$-C$_6$, or C$_5$-C$_6$ cycloalkyl), $R^{10F}$-substituted heterocycloalkyl (e.g., 3 to 8 membered, 3 to 6 membered, or 5 to 6 membered heterocycloalkyl), $R^{10F}$-substituted aryl (e.g., C$_6$-C$_{10}$, C$_{10}$ aryl, or phenyl), or $R^{10F}$-substituted heteroaryl (e.g., 5 to 10 membered, 5 to 9 membered, or 5 to 6 membered heteroaryl). In embodiments, $R^{10E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, $R^9$ and $R^{10}$ together with atoms attached thereto are joined to form $R^{9E}$-substituted or unsubstituted cycloalkyl (e.g., C$_3$-C$_{10}$, C$_3$-C$_8$, C$_3$-C$_6$, C$_4$-C$_6$, or C$_5$-C$_6$), $R^{9E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{9E}$-substituted or unsubstituted aryl (e.g., C$_6$-C$_{12}$, C$_6$-C$_{10}$, or phenyl), or $R^{9E}$-substituted or unsubstituted heteroaryl (e.g., 5 to 12 membered, 5 to 10 membered, 5 to 9 membered, or 5 to 6 membered). In embodiments, $R^9$ and $R^{10}$ together with atoms attached thereto are joined to form $R^{9E}$-substituted cycloalkyl (e.g., C$_3$-C$_{10}$, C$_3$-C$_8$, C$_3$-C$_6$, C$_4$-C$_6$, or C$_5$-C$_6$), $R^{9E}$-substituted heterocycloalkyl (e.g., 3 to 10 membered, 3 to 8 membered, 3 to 6 membered, 4 to 6 membered, 4 to 5 membered, or 5 to 6 membered), $R^{9E}$-substituted aryl (e.g., C$_6$-C$_{12}$, C$_6$-C$_{10}$, or phenyl), or $R^{9E}$-substituted heteroaryl (e.g., 5 to 12 membered, 5 to 10 membered, 5 to 9 membered, or 5 to 6 membered). In embodiments, $R^9$ and $R^{10}$ together with atoms attached thereto are joined to form unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered heteroaryl).

In embodiments, $R^{11}$ is hydrogen, halogen (e.g., —F, —Cl, —Br, —I), —CX"$_3$, —CHX"$_2$, —CH$_2$X", —OCX"$_3$, —OCH$_2$X", —OCHX"$_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11c}$ (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n11 is an integer from 0 to 4 (e.g. 0). m11 and v11 are independently an integer from 1 to 2. X$^{11}$ is independently —F, —Cl, —Br, or —I.

In embodiments, $R^{11}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{11E}$-substituted or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), $R^{11E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{11E}$-substituted or unsubstituted cycloalkyl (e.g., C$_3$-C$_{10}$, C$_3$-C$_8$, C$_3$-C$_6$, C$_4$-C$_6$, or C$_5$-C$_6$), $R^{11E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{11E}$-substituted or unsubstituted aryl (e.g., C$_6$-C$_{12}$, C$_6$-C$_{10}$, or phenyl), or $R^{11E}$-substituted or unsubstituted heteroaryl (e.g., 5 to 12 membered, 5 to 10 membered, 5 to 9 membered, or 5 to 6 membered). In embodiments, $R^{11}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, R$^{11E}$-substituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{11E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), R$^{11E}$-substituted cycloalkyl (e.g., C$_3$-C$_{10}$, C$_3$-C$_5$, C$_3$-C$_6$, C$_4$-C$_6$, or C$_5$-C$_6$), R$^{11E}$-substituted heterocycloalkyl (e.g., 3 to 10 membered, 3 to 8 membered, 3 to 6 membered, 4 to 6 membered, 4 to 5 membered, or 5 to 6 membered), R$^{11E}$-substituted aryl (e.g., C$_6$-C$_{12}$, C$_6$-C$_{10}$, or phenyl), or R$^{11E}$-substituted heteroaryl (e.g., 5 to 12 membered, 5 to 10 membered, 5 to 9 membered, or 5 to 6 membered). In embodiments, R$^{11}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_3$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{11E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{11F}$-substituted or unsubstituted alkyl (e.g., C$_1$-C$_8$, C$_1$-C$_6$, or C$_1$-C$_4$ alkyl), R$^{11F}$-substituted or unsubstituted heteroalkyl (e.g., 2 to 8 membered, 2 to 6 membered, or 2 to 4 membered heteroalkyl), R$^{11F}$-substituted or unsubstituted cycloalkyl (e.g., C$_3$-C$_8$, C$_3$-C$_6$, or C$_5$-C$_6$ cycloalkyl), R$^{11F}$-substituted or unsubstituted heterocycloalkyl (e.g., 3 to 8 membered, 3 to 6 membered, or 5 to 6 membered heterocycloalkyl), R$^{11F}$-substituted or unsubstituted aryl (e.g., C$_6$-C$_{10}$, C$_{10}$ aryl, or phenyl), or R$^{11F}$-substituted or unsubstituted heteroaryl (e.g., 5 to 10 membered, 5 to 9 membered, or 5 to 6 membered heteroaryl). In embodiments, R$^{11F}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{11F}$-substituted alkyl (e.g., C$_1$-C$_8$, C$_1$-C$_6$, or C$_1$-C$_4$ alkyl), R$^{11F}$-substituted heteroalkyl (e.g., 2 to 8 membered, 2 to 6 membered, or 2 to 4 membered heteroalkyl), R$^{11F}$-substituted cycloalkyl (e.g., C$_3$-C$_8$, C$_3$-C$_6$, or C$_5$-C$_6$ cycloalkyl), R$^{11F}$-substituted heterocycloalkyl (e.g., 3 to 8 membered, 3 to 6 membered, or 5 to 6 membered heterocycloalkyl), R$^{11F}$-substituted aryl (e.g., C$_6$-C$_{10}$, C$_{10}$ aryl, or phenyl), or R$^{11F}$-substituted heteroaryl (e.g., 5 to 10 membered, 5 to 9 membered, or 5 to 6 membered heteroaryl). In embodiments, R$^{11F}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_3$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, R$^{10}$ and R$^{11}$ together with atoms attached thereto are joined to form R$^{10E}$-substituted or unsubstituted cycloalkyl (e.g., C$_3$-C$_{10}$, C$_3$-C$_8$, C$_3$-C$_6$, C$_4$-C$_6$, or C$_5$-C$_6$), R$^{10E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{10E}$-substituted or unsubstituted aryl (e.g., C$_6$-C$_{12}$, C$_6$-C$_{10}$, or phenyl), or R$^{10E}$-substituted or unsubstituted heteroaryl (e.g., 5 to 12 membered, 5 to 10 membered, 5 to 9 membered, or 5 to 6 membered). In embodiments, R$^{10}$ and R$^{11}$ together with atoms attached thereto are joined to form R$^{10E}$-substituted cycloalkyl (e.g., C$_3$-C$_{10}$, C$_3$-C$_5$, C$_3$-C$_6$, C$_4$-C$_6$, or C$_5$-C$_6$), R$^{10E}$-substituted heterocycloalkyl (e.g., 3 to 10 membered, 3 to 8 membered, 3 to 6 membered, 4 to 6 membered, 4 to 5 membered, or 5 to 6 membered), R$^{10E}$-substituted aryl (e.g., C$_6$-C$_{12}$, C$_6$-C$_{10}$, or phenyl), or R$^{10E}$-substituted heteroaryl (e.g., 5 to 12 membered, 5 to 10 membered, 5 to 9 membered, or 5 to 6 membered). In embodiments, R$^{10}$ and R$^{11}$ together with atoms attached thereto are joined to form unsubstituted cycloalkyl (e.g., C$_3$-C$_{10}$, C$_3$-C$_3$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

In embodiments, R$^{12}$ is independently halogen (e.g., —F, —Cl, —Br, —I), —CX$^{12}{}_3$, —CHX$^{12}{}_2$, —CH$_2$X$^{12}$, —OCX$^{12}{}_3$, —OCH$_2$X$^{12}$, —OCHX$^{12}{}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)OR$^{12C}$, —NR$^{12A}$OR$^{12C}$ (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n12 is an integer from 0 to 4 (e.g. 0). m12 and v12 are independently an integer from 1 to 2. X$^{12}$ is independently —F, —Cl, —Br, or —I.

In embodiments, R$^{12}$ is independently —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, R$^{12E}$-substituted or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{12E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), R$^{12E}$-substituted or unsubstituted cycloalkyl (e.g., C$_3$-C$_{10}$, C$_3$-C$_5$, C$_3$-C$_6$, C$_4$-C$_6$, or C$_5$-C$_6$), R$^{12E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{12E}$-substituted or unsubstituted aryl (e.g., C$_6$-C$_{12}$, C$_6$-C$_{10}$, or phenyl), or R$^{12E}$-substituted or unsubstituted heteroaryl (e.g., 5 to 12 membered, 5 to 10 membered, 5 to 9 membered, or 5 to 6 membered). In embodiments, R$^{12}$ is independently —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, R$^{12E}$-substituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{12E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), R$^{12E}$-substituted cycloalkyl (e.g., C$_3$-C$_{10}$, C$_3$-C$_8$, C$_3$-C$_6$, C$_4$-C$_6$, or C$_5$-C$_6$), R$^{12E}$-substituted heterocycloalkyl (e.g., 3 to 10 membered, 3 to 8 membered, 3 to 6 membered, 4 to 6 membered, 4 to 5 membered, or 5 to 6 membered), R$^{12E}$-substituted aryl (e.g., C$_6$-C$_{12}$, C$_6$-C$_{10}$, or phenyl), or R$^{12E}$-substituted heteroaryl (e.g., 5 to 12 membered, 5 to 10 membered, 5 to 9 membered, or 5 to 6 membered). In embodiments, R$^{12}$ is independently —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{12E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{12E}$-substituted or unsubstituted alkyl (e.g., C$_1$-C$_8$, C$_1$-C$_6$, or C$_1$-C$_4$ alkyl), R$^{12E}$-substituted or unsubstituted heteroalkyl (e.g., 2 to 8 membered, 2 to 6 membered, or 2 to 4 membered heteroalkyl), R$^{12E}$-substituted or unsubstituted cycloalkyl (e.g., C$_3$-C$_8$, C$_3$-C$_6$, or C$_5$-C$_6$ cycloalkyl), R$^{12E}$-substituted or unsubstituted heterocycloalkyl (e.g., 3 to 8 membered, 3 to 6 membered, or 5 to 6 membered heterocycloalkyl), R$^{12E}$-substituted or unsubstituted aryl (e.g., C$_6$-C$_{10}$, C$_{10}$ aryl, or phenyl), or R$^{12F}$-substituted or unsubstituted heteroaryl (e.g., 5 to 10 membered, 5 to 9 membered, or 5 to 6 membered heteroaryl). In embodiments, R$^{12E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{12F}$-substituted alkyl (e.g., C$_1$-C$_8$, C$_1$-C$_6$, or C$_1$-C$_4$ alkyl), $R^{12F}$-substituted heteroalkyl (e.g., 2 to 8 membered, 2 to 6 membered, or 2 to 4 membered heteroalkyl), $R^{12F}$-substituted cycloalkyl (e.g., C$_3$-C$_3$, C$_3$-C$_6$, or C$_5$-C$_6$ cycloalkyl), $R^{12F}$-substituted heterocycloalkyl (e.g., 3 to 8 membered, 3 to 6 membered, or 5 to 6 membered heterocycloalkyl), $R^{12F}$-substituted aryl (e.g., C$_6$-C$_{10}$, C$_{10}$ aryl, or phenyl), or $R^{12F}$-substituted heteroaryl (e.g., 5 to 10 membered, 5 to 9 membered, or 5 to 6 membered heteroaryl). In embodiments, $R^{12E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

Each $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen, —CX$_3$, —CHX$_2$, —CH$_2$X (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I), —COOH, —CONH$_2$, substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). X is independently —F, —Cl, —Br, or —I. In embodiments, each $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —COOH, —CONH$_2$, $R^{20}$-substituted or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), $R^{20}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{20}$-substituted or unsubstituted cycloalkyl (e.g., C$_3$-C$_{10}$, C$_3$-C$_8$, C$_3$-C$_6$, C$_4$-C$_6$, or C$_5$-C$_6$), $R^{20}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{20}$-substituted or unsubstituted aryl (e.g., C$_6$-C$_{12}$, C$_6$-C$_{10}$, or phenyl), or $R^{20}$-substituted or unsubstituted heteroaryl (e.g., 5 to 12 membered, 5 to 10 membered, 5 to 9 membered, or 5 to 6 membered). In embodiments, each $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —COOH, —CONH$_2$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered). In embodiments, each $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, and $R^{12D}$ are independently hydrogen.

Each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted or unsubstituted heterocycloalkyl (e.g., 3 to 10 membered, 3 to 8 membered, 3 to 6 membered, 4 to 6 membered, 4 to 5 membered, or 5 to 6 membered), or $R^{20}$-substituted or unsubstituted heteroaryl (e.g., 5 to 12 membered, 5 to 10 membered, 5 to 9 membered, or 5 to 6 membered). Each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted heterocycloalkyl (e.g., 3 to 10 membered, 3 to 8 membered, 3 to 6 membered, 4 to 6 membered, 4 to 5 membered, or 5 to 6 membered), or $R^{20}$-substituted heteroaryl (e.g., 5 to 12 membered, 5 to 10 membered, 5 to 9 membered, or 5 to 6 membered). Each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form unsubstituted heterocycloalkyl (e.g., 3 to 10 membered, 3 to 8 membered, 3 to 6 membered, 4 to 6 membered, 4 to 5 membered, or 5 to 6 membered), or unsubstituted heteroaryl (e.g., 5 to 12 membered, 5 to 10 membered, 5 to 9 membered, or 5 to 6 membered). In embodiments, each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted or unsubstituted pyridyl. In embodiments, each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted or unsubstituted piperidinyl. In embodiments, each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted or unsubstituted morpholinyl. In embodiments, each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ joined to form $R^{20}$-substituted or unsubstituted pyrrolyl. In embodiments, each $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, and $R^{12A}$ and $R^{12B}$ together with nitrogen attached thereto may independently be joined to form $R^{20}$-substituted or unsubstituted pyrimidinyl.

$R^{1F}$, $R^{2F}$, $R^{3F}$, $R^{4F}$, $R^{5F}$, $R^{6F}$, $R^{7F}$, $R^{8F}$, $R^{9F}$, $R^{10F}$, $R^{11F}$, $R^{12F}$, $R^{19}$ and $R^{20}$ are independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$ aryl, C$_{10}$ aryl or phenyl), or unsubstituted heteroaryl (e.g., 5 to 10 membered, 5 to 9 membered, or 5 to 6 membered heteroaryl).

X, $X^7$, $X^8$, $X^9$, $X^{10}$, $X^{11}$, $X^{12}$ are independently —F, —Cl, —Br, or —I. In embodiments, X is —F. In embodiments, X is —Cl. In embodiments, X is —Br. In embodiments, X is —I. In embodiments, $X^7$ is —F. In embodiments, $X^7$ is —Cl. In embodiments, $X^7$ is —Br. In embodiments, $X^7$ is —I. In embodiments, $X^8$ is —F. In embodiments, $X^8$ is —Cl. In embodiments, $X^8$ is —Br. In embodiments, $X^8$ is —I. In embodiments, $X^9$ is —F. In embodiments, $X^9$ is —Cl. In embodiments, $X^9$ is —Br. In embodiments, $X^9$ is —I. In embodiments, $X^{10}$ is —F. In embodiments, $X^{10}$ is —Cl. In embodiments, $X^{10}$ is —Br. In embodiments, $X^{10}$ is —I. In embodiments, $X^{11}$ is —F. In embodiments, $X^{11}$ is —Cl. In embodiments, $X^{11}$ is —Br. In embodiments, $X^{11}$ is —I. In embodiments, $X^{12}$ is —F. In embodiments, $X^{12}$ is —Cl. In embodiments, $X^{12}$ is —Br. In embodiments, $X^{12}$ is —I.

n7, n8, n9, n10, n11 and n12 are independently an integer from 0 to 4 (e.g. 0). In embodiments, n7 is 0. In embodiments, n7 is 1. In embodiment, n7 is 2. In embodiments, n7 is 3. In embodiment, n7 is 4. In embodiments, n8 is 0. In embodiments, n8 is 1. In embodiment, n8 is 2. In embodiments, n8 is 3. In embodiment, n8 is 4. In embodiments, n9 is 0. In embodiments, n9 is 1. In embodiment, n9 is 2. In embodiments, n9 is 3. In embodiment, n9 is 4. In embodiments, n10 is 0. In embodiments, n10 is 1. In embodiment, n10 is 2. In embodiments, n10 is 3. In embodiment, n10 is 4. In embodiments, n11 is 0. In embodiments, n11 is 1. In embodiment, n11 is 2. In embodiments, n11 is 3. In embodiment, n11 is 4. In embodiments, n12 is 0. In embodiments, n12 is 1. In embodiment, n12 is 2. In embodiments, n12 is 3. In embodiment, n12 is 4.

m7, m8, m9, m10, m11, and m12 are independently an integer from 1 to 2. In embodiment, m6 is 2. In embodiments, m7 is 1. In embodiment, m7 is 2. In embodiments, m8 is 1. In embodiment, m8 is 2. In embodiments, m9 is 1. In embodiment, m9 is 2. In embodiments, m10 is 1. In embodiment, m10 is 2. In embodiments, m11 is 1. In embodiment, m11 is 2. In embodiments, m12 is 1. In embodiment, m12 is 2.

v7, v8, v9, v10, v11, and v12 are independently an integer from 1 to 2. In embodiments, v7 is 1. In embodiment, v7 is 2. In embodiments, v8 is 1. In embodiment, v8 is 2. In embodiments, v9 is 1. In embodiment, v9 is 2. In embodiments, v10 is 1. In embodiment, v10 is 2. In embodiments, v11 is 1. In embodiment, v11 is 2. In embodiments, v12 is 1. In embodiment, v12 is 2.

In embodiments, p is 1. In embodiments, p is 2. In embodiments, p is 3. In embodiments, p is 4. In embodiments, p is 5. In embodiments, p is 6. In embodiments, p is 7. In embodiments, p is 8. In embodiments, p is 9. In embodiments, p is 10.

In embodiment, z is 0. In embodiments, z is 1. In embodiment, z is 2. In embodiments, z is 3. In embodiment, z is 4. In embodiments, z is 5. In embodiment, z is 6. In embodiment, z is 7. In embodiments, z is 8. In embodiment, z is 9. In embodiment, z is 10. In embodiment, z is 11.

In embodiments, the compound is

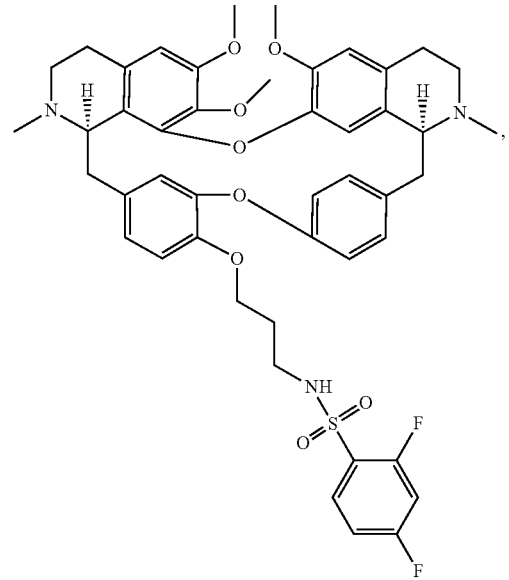

BBM-PA-3

BBM-PA-4

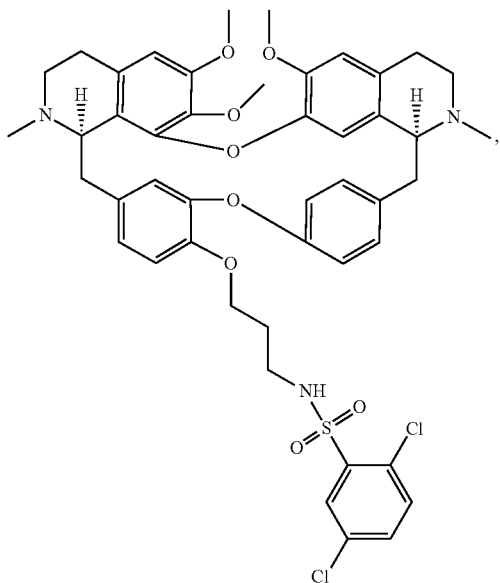

BBM-PA-1

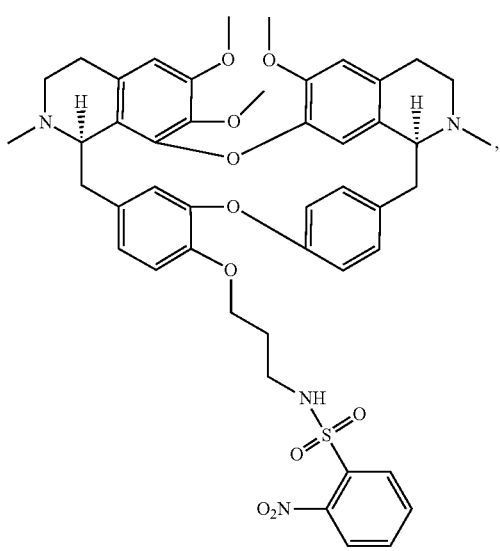

BBM-PA-5

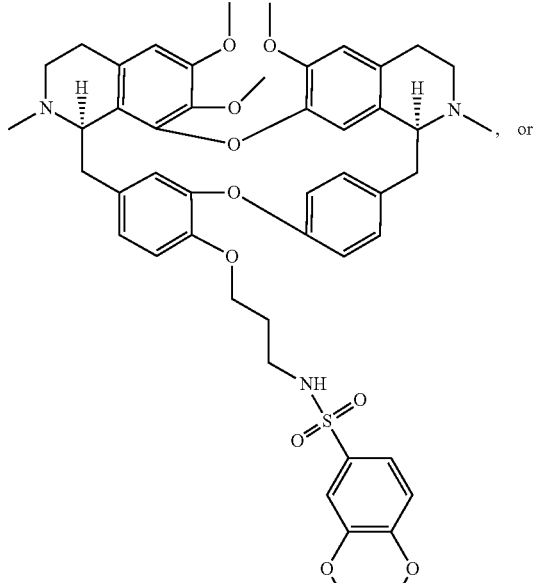, or

BBM-PA-7

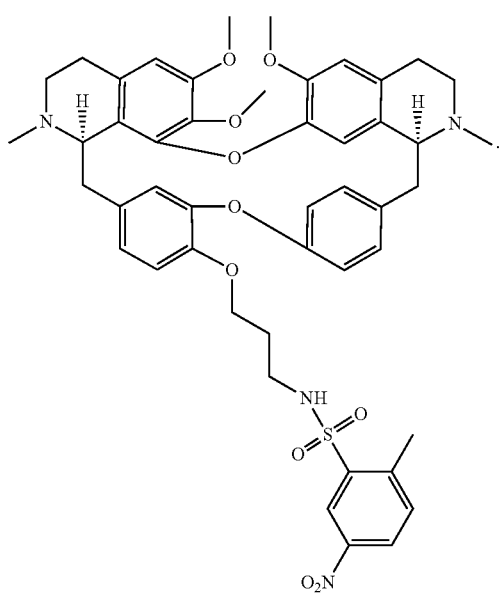.

In embodiments, the compound is a compound described herein (e.g., in an aspect, embodiment, example, table, figure, scheme, appendix, claim or combination thereof).

III. Pharmaceutical Compositions

Also provided herein are pharmaceutical formulations. In embodiments, the pharmaceutical formulation includes a compound (e.g. formula (I), (IA), (II), (IF), (III), (III'), (IV), (IV'), (V), (V'), (VI), (VP), (VII-A), (VII-A'), (VII-B), (VII-B'), (VIII-A), (VIII-A'), (VIII-B), or (VIII-B')) described above (including all embodiments thereof) and a pharmaceutically acceptable excipient.

In embodiments, the pharmaceutical composition includes a compound (e.g. formula (I), (IA), (II), (IP), (III), (IIP), (IV), (IV'), (V), (V'), (VI), (VI'), (VII-A), (VII-A'), (VII-B), (VII-B'), (VIII-A), (VIII-A'X (VIII-B), or (VIII-B')) described above that inhibits growth of cancer cells. In embodiments, the pharmaceutical composition includes a compound (e.g. formula (I), (IA), (II), (IP), (III), (IIP), (IV), (IV'), (V), (V'), (VI), (VI'), (VII-A), (VII-A'), (VII-B), (VII-B'), (VIII-A), (VIII-A'X (VIII-B), or (VIII-B')) described above that inhibits $Ca^{2+}$/calmodulin-dependent protein kinases (e.g., CAMK, CAMKII (e.g., CAMKIIα, CAMKIIβ, CAMKIIδ, or CAMKIIγ), or CAMKIIγ) in a cancer cell. In embodiments, the compound has a half maximal inhibitory concentration ($IC_{50}$) against cancer cell growth less than about 100 μM. In embodiments, the compound has $IC_{50}$ against cancer cell growth less than about 90 μM. In embodiments, the compound has $IC_{50}$ against cancer cell growth less than about 80 μM. In embodiments, the compound has $IC_{50}$ against cancer cell growth less than about 70 μM. In embodiments, the compound has $IC_{50}$ against cancer cell growth less than about 60 μM. In embodiments, the compound has $IC_{50}$ against cancer cell growth less than about 50 μM. In embodiments, the compound has $IC_{50}$ against cancer cell growth less than about 40 μM. In embodiments, the compound has $IC_{50}$ against cancer cell growth less than about 30 μM. In embodiments, the compound has $IC_{50}$ against cancer cell growth less than about 20 μM. In embodiments, the compound has $IC_{50}$ against cancer cell growth less than about 10 μM. In embodiments, the compound has $IC_{50}$ against cancer cell growth less than about 9 μM. In embodiments, the compound has $IC_{50}$ against cancer cell growth less than about 8 μM. In embodiments, the compound has $IC_{50}$ against cancer cell growth less than about 7 μM. In embodiments, the compound has $IC_{50}$ against cancer cell growth less than about 6 μM. In embodiments, the compound has $IC_{50}$ against cancer cell growth less than about 5 μM. In embodiments, the compound has $IC_{50}$ against cancer cell growth less than about 4 μM. In embodiments, the compound has $IC_{50}$ against cancer cell growth less than about 3 μM. In embodiments, the compound has $IC_{50}$ against cancer cell growth less than about 2 μM. In embodiments, the compound has $IC_{50}$ against cancer cell growth less than about 1 μM.

In embodiments, the pharmaceutical composition includes a compound of:

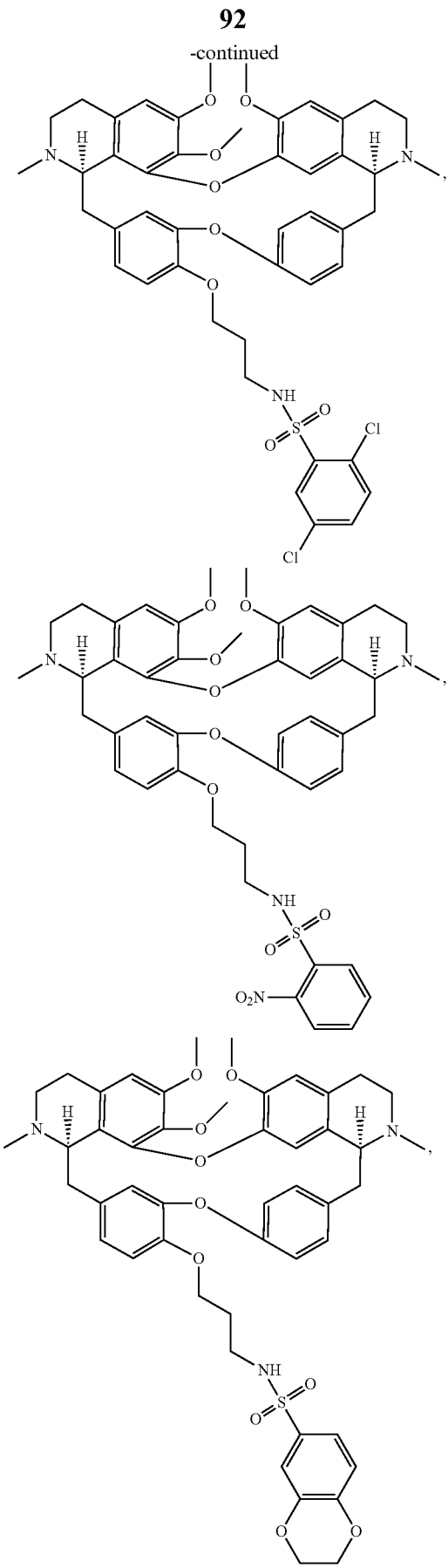

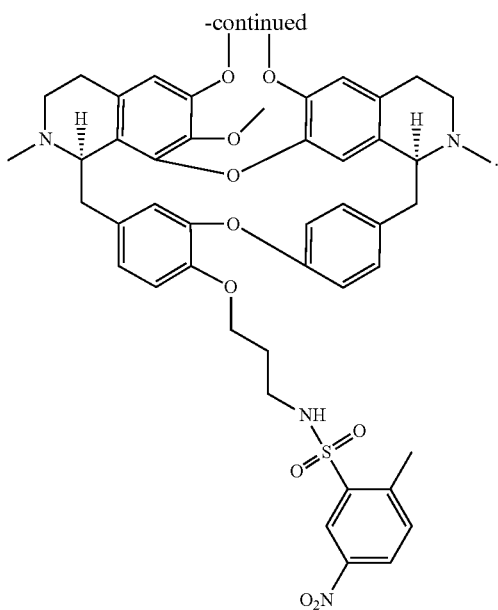

The pharmaceutical compositions described herein, including embodiments thereof may be used in the treatment of cancers. In embodiments, the pharmaceutical compositions described herein, including embodiments thereof may be used in the treatment of the cancer associated with $Ca^{2+}$/calmodulin-dependent protein kinase (CAMK). In embodiments, the pharmaceutical compositions described herein, including embodiments thereof may be used in the treatment of the cancer associated with $Ca^{2+}$/calmodulin-dependent protein kinase II (CAMKII) including isoforms thereof (e.g., CAMKIIα, CAMKIIβ, CAMKIIδ, or CAMKIIγ).

In embodiments, the pharmaceutical compositions described herein, including embodiments thereof may be used in the treatment of benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia (e.g. AML or CML), acute lymphoblastic leukemia, acute lymphocytic leukemia, erythroleukemia, multiple myeloma, blood cancer, and lymphatic tissues cancer. In embodiments, the cancer is a benign tumor. In embodiments, the cancer is a solid tumor. In embodiments, the cancer is a breast cancer. In embodiments, the cancer is a colon-rectal cancer. In embodiments, the cancer is an oral cancer. In embodiments, the cancer is a lung cancer. In embodiments, the cancer is a respiratory system cancers. In embodiments, the cancer is a melanoma. In embodiments, the cancer is a skin cancer. In embodiments, the cancer is a uterine cancer. In embodiments, the cancer is a pancreatic cancer. In embodiments, the cancer is a liver cancer. In embodiments, the cancer is a prostate cancer. In embodiments, the cancer is a cervical cancer. In embodiments, the cancer is a testicular cancer. In embodiments, the cancer is a genital cancer. In embodiments, the cancer is a bladder cancer. In embodiments, the cancer is a kidney cancer. In embodiments, the cancer is a urinary organs cancer. In embodiments, the cancer is an ovarian cancer. In embodiments, the cancer is a leukemia. In embodiments, the cancer is an acute lymphoblastic leukemia or acute lymphocytic leukemia. In embodiments, the cancer is an erythroleukemia. In embodiments, the cancer is a multiple myeloma. In embodiments, the cancer is a blood cancer. In embodiments, the cancer is a lymphatic tissues cancer. In embodiments, the cancer is T-cell lymphoma.

In embodiments, the pharmaceutical composition includes a compound described herein (e.g., in an aspect, embodiment, example, table, figure, scheme, appendix, or claim) and a pharmaceutically acceptable excipient.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al, In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages.

Pharmaceutical admixtures suitable for use in the pharmaceutical compositions presented herein may include those described, for example, in Pharmaceutical Sciences (17th Ed., Mack Pub. Co., Easton, PA) and WO 96/05309, the teachings of both of which are hereby incorporated by reference.

IV. Methods of Treatments

Provided herein are methods of treating a cancer in a subject in need thereof, the method including administering an effective amount a compound (e.g. formula (I), (IA), (II), (IF), (III), (IIP), (IV), (IV'), (V), (V'), (VI), (VI'), (VII-A), (VII-A'), (VII-B), (VII-B'), (VIII-A), (VIII-A'), (VIII-B), or (VIII-B')) described herein. In embodiments, the cancer can be benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia (e.g. AML or CML), acute lymphoblastic leukemia, acute lymphocytic leukemia, erythroleukemia, multiple myeloma, blood cancer, and lymphatic tissues cancer. In embodiments, the cancer is a benign tumor. In embodiments, the cancer is a solid tumor. In embodiments, the cancer is a breast cancer. In embodiments, the cancer is a colon-rectal cancer. In embodiments, the cancer is an oral cancer. In embodiments, the cancer is a lung cancer. In embodiments, the cancer is a respiratory system cancers. In embodiments, the cancer is a melanoma. In embodiments, the cancer is a skin cancer. In embodiments, the cancer is a uterine cancer. In embodiments, the cancer is a pancreatic cancer. In embodiments, the cancer is a liver cancer. In embodiments, the cancer is a prostate cancer. In embodiments, the cancer is a cervical cancer. In embodiments, the cancer is a testicular cancer. In embodiments, the cancer is a genital cancer. In embodiments, the cancer is a bladder cancer. In embodiments, the cancer is a kidney cancer. In embodiments, the cancer is a urinary organs cancer. In embodiments, the cancer is an ovarian cancer. In embodiments, the cancer is a leukemia. In embodiments, the cancer is an acute lymphoblastic leukemia or acute lymphocytic leukemia. In embodiments, the cancer is an erythroleukemia. In embodiments, the cancer is a multiple myeloma. In embodiments, the cancer is a blood cancer. In embodiments, the cancer is a lymphatic tissues cancer. In embodiments, the cancer is T-cell lymphoma.

In embodiments, the method of treating cancer includes suppression or inhibition of $Ca^{2+}$/calmodulin-dependent protein kinases (e.g., CAMK, CAMKII (e.g., CAMKIIα, CAMKIIβ, CAMKIIδ, or CAMKIIγ), or CAMKIIγ) in the tumor cells. In embodiments, the method of treating cancer includes suppression, reduction, or regulating expression of responding genes in the tumor cells by inhibiting $Ca^{2+}$/calmodulin-dependent protein kinases (e.g., CAMK, CAMKII (e.g., CAMKIIα, CAMKIIβ, CAMKIIδ, or CAMKIIγ), or CAMKIIγ). In embodiments, the method of treating cancer includes inhibiting $Ca^{2+}$/calmodulin-dependent protein kinases (e.g., CAMK, CAMKII (e.g., CAMKIIα, CAMKIIβ, CAMKIIδ, or CAMKIIγ), or CAMKIIγ) by using an effective amount of the inhibitor thereof. In embodiments, the method of treating cancer includes suppression, reduction, or regulating expression of responding genes (e.g., regulating phosphorylating transcription factors) in the tumor cells by contacting the cancer or tumor cell with an effective amount of the $Ca^{2+}$/calmodulin-dependent protein kinase (e.g., CAMK, CAMKII (e.g., CAMKIIα, CAMKIIβ, CAMKIIδ, or CAMKIIγ), or CAMKIIγ) inhibitor. In embodiments, the method of treating cancer includes inhibiting $Ca^{2+}$/calmodulin-dependent protein kinase (e.g., CAMK, CAMKII (e.g., CAMKIIα, CAMKIIβ, CAMKIIδ, or CAMKIIγ), or CAMKIIγ) by using effective amount of a compound (e.g. formula (I), (IA), (II), (IF), (III), (IIP), (IV), (IV'), (V), (V'), (VI), (VI'), (VII-A), (VII-A'), (VII-B'), (VIII-A), (VIII-A'X (VIII-B), or (VIII-B')) described above (including all embodiments thereof). In embodiments, the method of treating cancer includes inhibiting CAMK, CAMKII (e.g., CAMKIIα, CAMKIIβ, CAMKIIδ, or CAMKIIγ), or CAMKIIγ in a cancer or tumor cell by contacting the cancer or tumor cell with the effective amount of a compound (e.g. formula (I), (IA), (II), (IF), (III), (III'), (IV), (IV'), (V), (V'), (VI), (VI'), (VII-A), (VII-A'), (VII-B), (VII-B'), (VIII-A), (VIII-A'), (VIII-B), or (VIII-B')) described above (including all embodiments thereof).

In embodiments, the methods of treating cancer described herein yield a suppression of tumor growth. The suppressed tumor growth may indicate the absence of toxicity symptoms (e.g. body weight loss). Those skilled in the art understand that body weight loss observed during cancer treatments is a result of toxicity associated with the treatment (e.g. killing of healthy tissue). Accordingly, the compounds described herein may provide effective therapeutic value without toxicity issues normally associated with cancer treatments.

V. Embodiments

Embodiment 1. A compound having a formula:

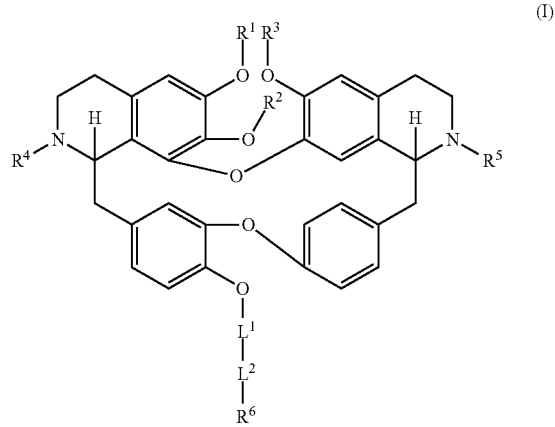

(I)

wherein:
Each $R^1$, $R^2$, $R^3$, $R^4$, and $R^5$ is independently hydrogen, or substituted or unsubstituted $C_1$-$C_{10}$ alkyl;
$L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$L^2$ is —$NR^{2A}S(O)_2$— or —$S(O)_2NR^{2B}$—;
$R^6$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^{2A}$ and $R^{2B}$ are independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
X is independently —F, —Cl, —Br or —I,
or a salt thereof.

Embodiment 2. The compound of Embodiment 1 having a formula:

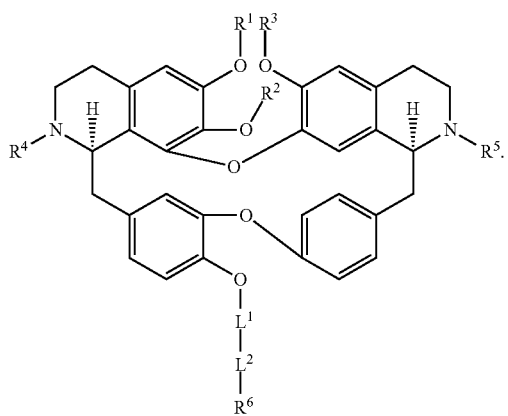

(IA)

Embodiment 3. The compound of any one of Embodiments 1-2, wherein $L^1$ is substituted or unsubstituted $C_1$-$C_{10}$ alkylene.

Embodiment 4. The compound of any one of Embodiments 1-2, wherein $L^1$ is unsubstituted $C_1$-$C_{10}$ alkylene.

Embodiment 5. The compound of any one of Embodiments 1-2, wherein $L^1$ is substituted or unsubstituted $C_1$-$C_5$ alkylene.

Embodiment 6. The compound of any one of Embodiments 1-2, wherein $L^1$ is unsubstituted $C_1$-$C_5$ alkylene.

Embodiment 7. The compound of any one of Embodiments 1-6, wherein each $R^{2A}$ and $R^{2B}$ is independently hydrogen or substituted or unsubstituted $C_1$-$C_5$ alkyl.

Embodiment 8. The compound of any one of Embodiments 1-6, wherein each $R^{2A}$ and $R^{2B}$ is independently hydrogen or unsubstituted $C_1$-$C_5$ alkyl.

Embodiment 9. The compound of any one of Embodiments 1-6, wherein $R^{2A}$ and $R^{2B}$ are hydrogen.

Embodiment 10. The compound of any one of Embodiments 1-6, wherein $L^2$ is —NHS(O)$_2$—.

Embodiment 11. The compound of Embodiment 1, wherein the compound has a formula:

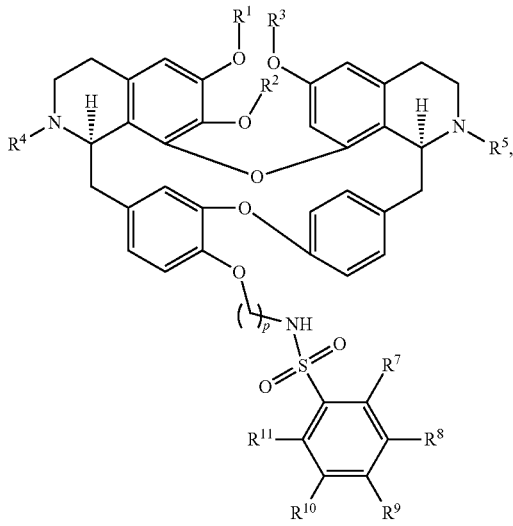

(II)

wherein:

$R^7$ is hydrogen, halogen, —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)O R$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ and $R^8$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^8$ and $R^9$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R⁹ and R¹⁰ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R¹⁰ and R¹¹ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, and $R^{11D}$ are independently hydrogen, —CX₃, —CHX₂, —CH₂X, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

n7, n8, n9, n10, and n11 are independently an integer from 0 to 4;

m7, m8, m9, m10, m11, v7, v8, v9, v10, and v11 are independently an integer from 1 to 2; and $X^7$, $X^8$, $X^9$, $X^{10}$, and $X^{11}$ are independently —F, —Cl, —Br or —I.

Embodiment 12. The compound of Embodiment 1, wherein the compound has a formula:

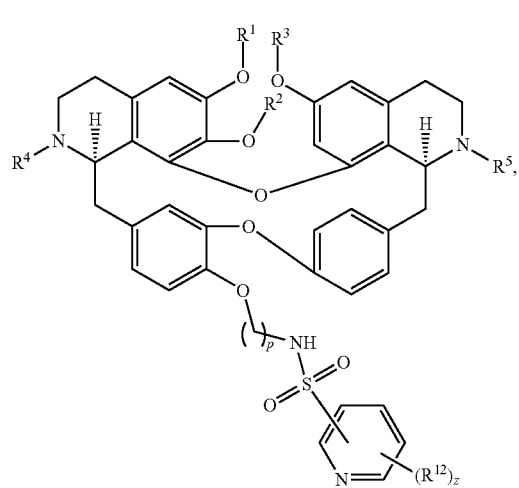

(III)

wherein:

$R^{12}$ is independently halogen, —CX¹²₃, —CHX¹²₂, —CH₂X¹², —OCX¹²₃, —OCH₂X¹², —OCHX¹²₂, —N₃, —CN, —SO$_{n12}$R¹²ᴰ, —SO$_{v12}$NR¹²ᴬR¹²ᴮ, —NHC(O)NR¹²ᴬR¹²ᴮ, —N(O)$_{m12}$, —NR¹²ᴬR¹²ᴮ, —C(O)R¹²ᶜ, —C(O)—OR¹²ᶜ, —C(O)NR¹²ᴬR¹²ᴮ, —OR¹²ᴰ, —NR¹²ᴬSO₂R¹²ᴰ, —NR¹²ᴬC(O)R¹²ᶜ, —NR¹²ᴬC(O)O R¹²ᶜ, —NR¹²ᴬOR¹²ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12A}$, $R^{12B}$, $R^{12C}$, and $R^{12D}$ are independently hydrogen, —CX₃, —CHX₂, —CH₂X, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

z is an integer from 0 to 4;

n12 is independently an integer from 0 to 4;

m12 and v12 are independently an integer from 1 to 2; and $X^{12}$ is independently —F, —Cl, —Br or —I.

Embodiment 13. The compound of Embodiment 1, wherein the compound has a formula:

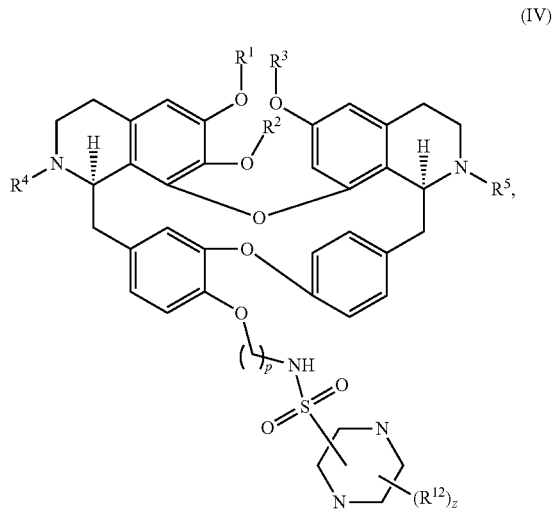

(IV)

wherein:

$R^{12}$ is independently halogen, —CX¹²₃, —CHX¹²₂, —CH₂X¹², —OCX¹²₃, —OCH₂X¹², —OCHX¹²₂, —N₃, —CN, —SO$_{n12}$R¹²ᴰ, —SO$_{v12}$NR¹²ᴬR¹²ᴮ, —NHC(O)NR¹²ᴬR¹²ᴮ, —N(O)$_{m12}$, —NR¹²ᴬR¹²ᴮ, —C(O)R¹²ᶜ, —C(O)—OR¹²ᶜ, —C(O)NR¹²ᴬR¹²ᴮ, —OR¹²ᴰ, —NR¹²ᴬSO₂R¹²ᴰ, —NR¹²ᴬC(O)R¹²ᶜ, —NR¹²ᴬC(O)O R¹²ᶜ, —NR¹²ᴬOR¹²ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12A}$, $R^{12B}$, $R^{12C}$, and $R^{12D}$ are independently hydrogen, —CX₃, —CHX₂, —CH₂X, —COOH, —CONH₂, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

z is an integer from 0 to 9;

n12 is independently an integer from 0 to 4;

m12 and v12 are independently an integer from 1 to 2; and $X^{12}$ is independently —F, —Cl, —Br or —I.

Embodiment 14. The compound of any one of Embodiments 11-13, wherein each $R^1$, $R^2$, $R^3$, $R^4$, and $R^5$ is independently unsubstituted $C_1$-$C_{10}$ alkyl.

Embodiment 15. The compound of any one of Embodiments 11-13, wherein each $R^1$, $R^2$, $R^3$, $R^4$, and $R^5$ is independently unsubstituted $C_1$-$C_5$ alkyl.

Embodiment 16. The compound of any one of Embodiments 11-13, wherein each $R^1$, $R^2$, $R^3$, $R^4$, and $R^5$ are independently unsubstituted methyl.

Embodiment 17. The compound of any one of Embodiments 11-13, wherein p is an integer from 2 to 4.

Embodiment 18. The compound of any one of Embodiments 11-13, wherein p is 2 or 3.

Embodiment 19. The compound of any one of Embodiments 11 and 14-18, wherein each $R^7$, $R^8$, $R^9$, $R^{10}$, and $R^{11}$ is independently hydrogen, —F, —Cl, —NO$_2$ or unsubstituted methyl.

Embodiment 20. The compound of any one of Embodiments 11 and 14-19, wherein the compound has a formula (V)

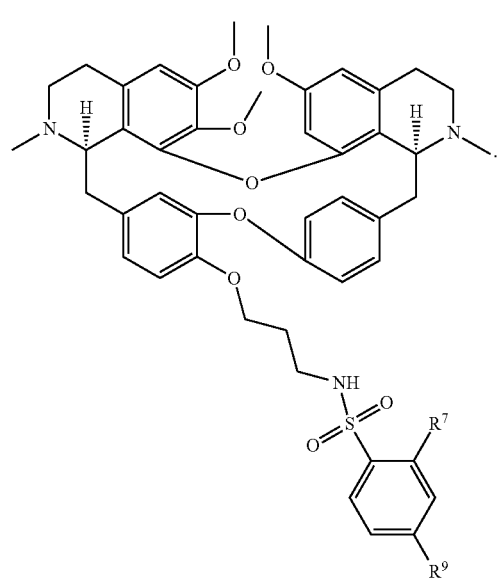

Embodiment 21. The compound of Embodiment 20, wherein each $R^7$ and $R^9$ is independently hydrogen, —F or —NO$_2$.

Embodiment 22. The compound of any one of Embodiments 11 and 14-19, wherein the compound has a formula (VI)

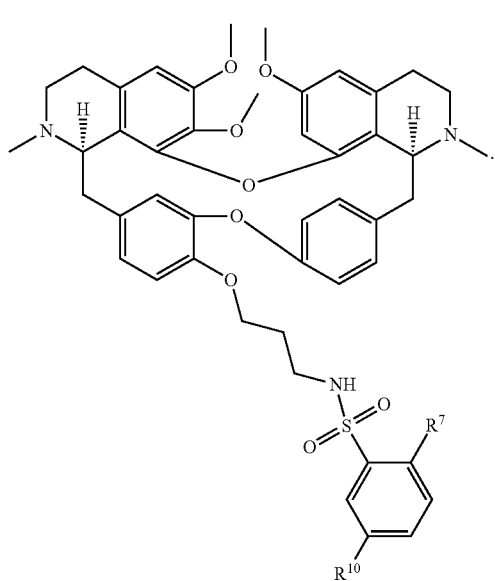

Embodiment 23. The compound of Embodiment 22, wherein each $R^7$ and $R^{10}$ is independently —Cl, —NO$_2$ or unsubstituted methyl.

Embodiment 24. The compound of Embodiment 1, wherein the compound is

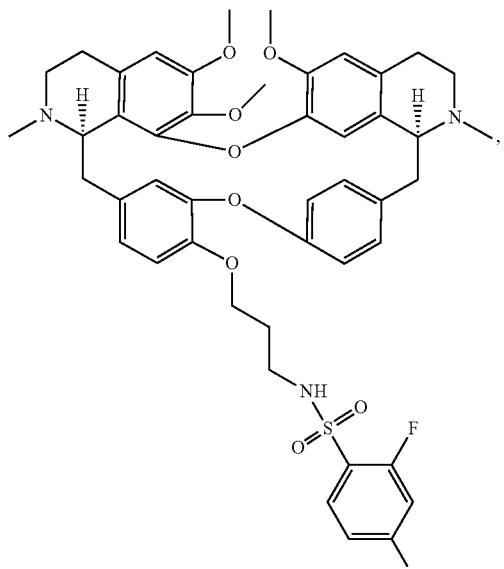

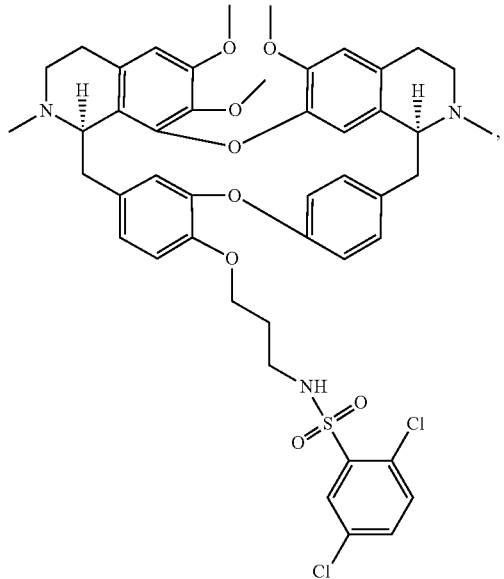

105
-continued

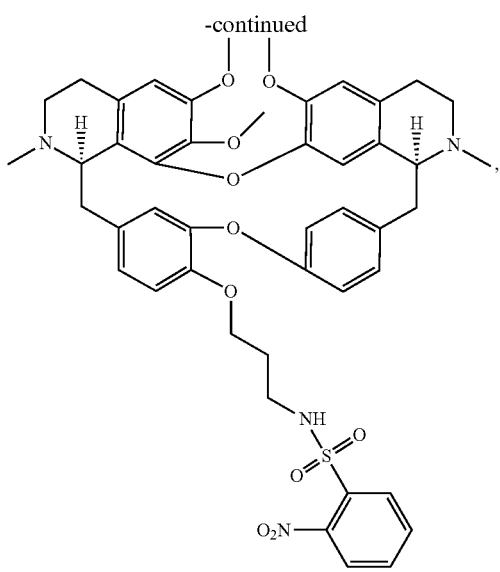

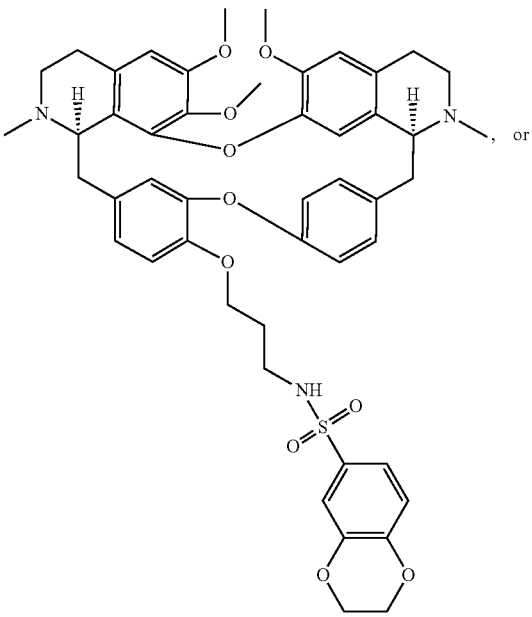, or

106
-continued

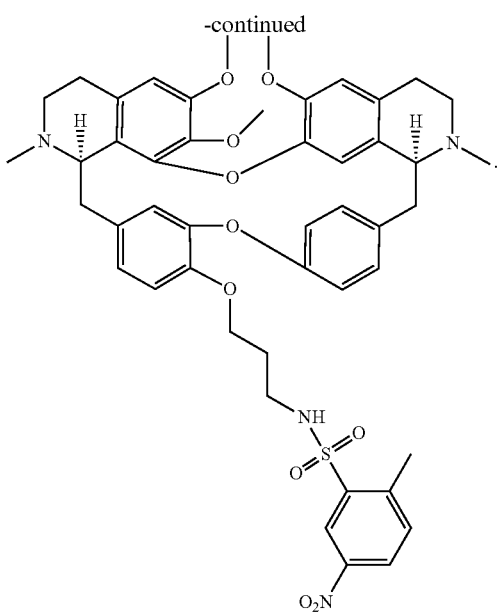

Embodiment 25. A pharmaceutical composition comprising a compound of any one of Embodiments 1-24, or a salt thereof, and a pharmaceutically acceptable carrier.

Embodiment 26. A method of treating a cancer comprising administering a therapeutically effective amount of a pharmaceutical composition of Embodiment 25 to a subject in need thereof.

Embodiment 27. The method of Embodiment 26, wherein the cancer is a $Ca^{2+}$/calmodulin-dependent protein kinase (CAMK) associated cancer.

Embodiment 28. The method of Embodiment 26, wherein the cancer is a $Ca^{2+}$/calmodulin-dependent protein kinase II γ (CAMKIIγ) associated cancer.

Embodiment 29. The method of Embodiment 26, wherein the cancer is benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia, acute lymphoblastic leukemia, acute lymphocytic leukemia, erythroleukemia, multiple myeloma, blood cancer, and lymphatic tissues cancer.

Embodiment 30. The method of Embodiment 26, wherein the cancer is T-cell lymphoma.

Embodiment 31. A method of inhibiting a $Ca^{2+}$/calmodulin-dependent protein kinase (CAMK) in a cancer cell comprising contacting the cell with a compound of any one of Embodiments 1-24, or a salt thereof.

Embodiment 32. The method of Embodiment 31, wherein the CAMK comprises $Ca^{2+}$/calmodulin-dependent protein kinase II γ (CAMKIIγ).

Embodiment 33. The method of Embodiment 31, wherein the cancer cell is a benign tumor cell, solid tumor cell, breast cancer cell, colon-rectal cancer cell, oral cancer cell, lung cancer cell, respiratory system cancers cell, melanoma cell, skin cancers cell, uterine cancer cell, pancreatic cancer cell, liver cancer cell, prostate cancer cell, cervical cancer cell, testicular cancer cell, genital cancer cell, bladder cancer cell, kidney cancer cell, urinary organs cancers cell, ovarian cancer cell, leukemia cancer cell, acute lymphoblastic leukemia cancer cell, acute lymphocytic leukemia cancer cell, erythroleukemia cancer cell, multiple myeloma cancer cell, blood cancer cell, or lymphatic tissues cancer cell.

Embodiment 34. The method of Embodiment 31, wherein the cancer cell is T-cell lymphoma cancer cell.

Embodiment 35. A method of treating a cancer comprising administering a therapeutically effective amount of a compound of any one of Embodiments 1-24, or a salt thereof, to a subject in need thereof.

Embodiment 36. The method of Embodiment 35, wherein the cancer is a $Ca^{2+}$/calmodulin-dependent protein kinase (CAMK) associated cancer.

Embodiment 37. The method of Embodiment 35, wherein the cancer is a $Ca^{2+}$/calmodulin-dependent protein kinase II γ (CAMKIIγ) associated cancer.

Embodiment 38. The method of Embodiment 35, wherein the cancer is benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia, acute lymphoblastic leukemia, acute lymphocytic leukemia, erythroleukemia, multiple myeloma, blood cancer, and lymphatic tissues cancer.

Embodiment 39. The method of Embodiment 35, wherein the cancer is T-cell lymphoma.

VI. Examples

Although the foregoing section has been described in some detail by way of illustration and example for purposes of clarity of understanding, it is apparent to those skilled in the art that certain minor changes and modifications will be practiced in light of the above teaching. Therefore, the description and examples should not be construed as limiting the scope of any invention described herein.

All references cited herein, including patent applications and publications, are hereby incorporated by reference in their entirety.

Example 1: Synthesis

Scheme 1

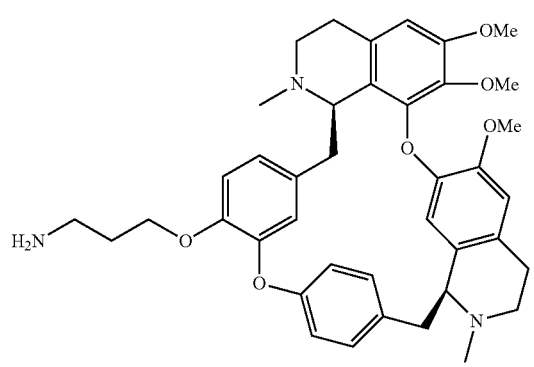

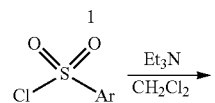

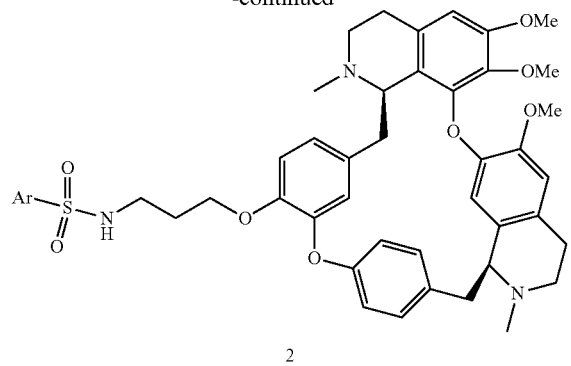

To a stirred solution of amine 1 (0.7 mmol) in 7 mL $CH_2Cl_2$ were added $Et_3N$ (1.05 mmol, 1.5 equiv) and Aromatic sulfonyl chloride (0.84 mmol, 1.2 equiv) at 0° C. The reaction was stirred at rt for 1 h and quenched with sat. $NaHCO_3$. The mixture was diluted with $CH_2Cl_2$ and washed with $H_2O$. The organic layer was dried and evaporated. The residue was purified with chromatograph to provide the product 2.

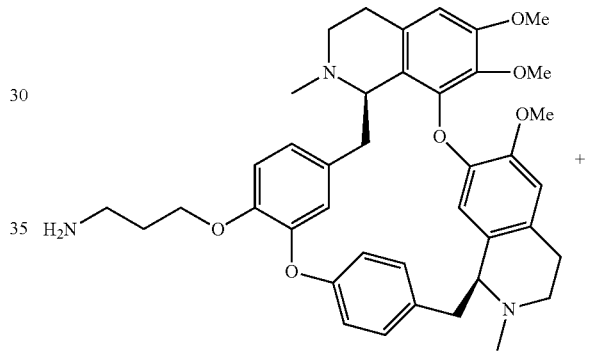

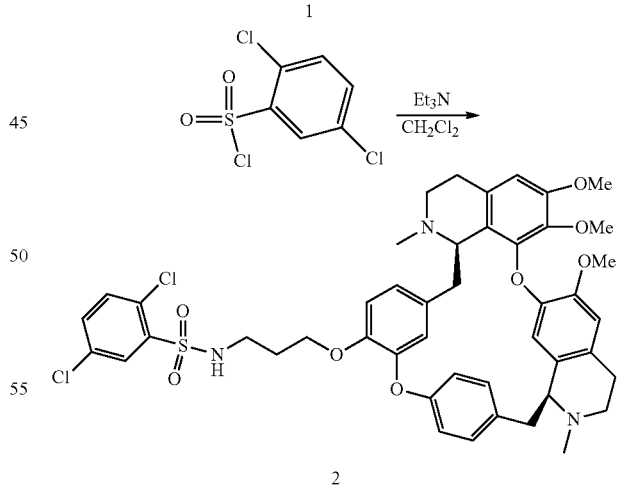

To a stirred solution of amine 1 (466 mg, 0.7 mmol) in 7 mL $CH_2Cl_2$ were added $Et_3N$ (106 mg, 1.05 mmol, 1.5 equiv) and 2,5-dichlorobenzenesulfonyl chloride (206 mg, 0.84 mmol, 1.2 equiv) at 0° C. The reaction was stirred at rt for 1 h and quenched with sat. $NaHCO_3$. The mixture was diluted with $CH_2Cl_2$ and washed with $H_2O$. The organic layer was dried and evaporated. The residue was purified with chromatograph to provide the product 2 (BBM-PA-5; 550 mg, 0.63 mmol, 90% yield). $^1$H NMR (400 MHz, CDCl$_3$) δ (ppm): 8.02 (d, 1H, J=2.8 Hz), 7.37 (dd, 1H, J=2.8 Hz, 8.8 Hz), 7.33 (d, 1H, J=8.8 Hz), 7.28 (dd, 1H, J=2.0 Hz, 8.0 Hz), 7.10 (dd, 1H, J=2.4 Hz, 8.0 Hz), 6.72-6.78 (m, 2H), 6.61 (dd, 1H, J=2.4 Hz, 8.0 Hz), 6.52 (s, 1H), 6.36-6.44 (b, 1H), 6.27 (s, 1H), 6.14-6.20 (m, 1H), 5.94-6.00 (b, 1H), 4.06-4.18 (m, 2H), 3.76-3.88 (m, 2H), 3.74 (s, 3H), 3.60 (s, 3H), 3.18-3.44 (m, 5H), 3.11 (s, 3H), 3.01 (d, 1H, J=14.0 Hz), 2.74-2.94 (m, 6H), 2.50-2.60 (m, 1H), 2.56 (s, 3H), 2.30-2.40 (m, 1H), 2.24 (s, 3H), 1.96-2.04 (m, 2H); MS C$_{46}$H$_{49}$Cl$_2$N$_3$O$_8$S [M+H]$^+$ calc'd: 874.27, found: 874.36

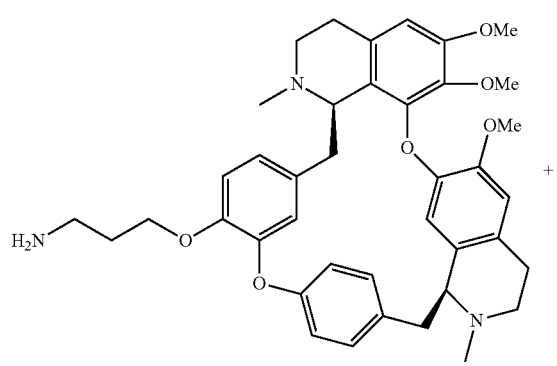

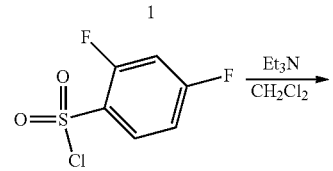

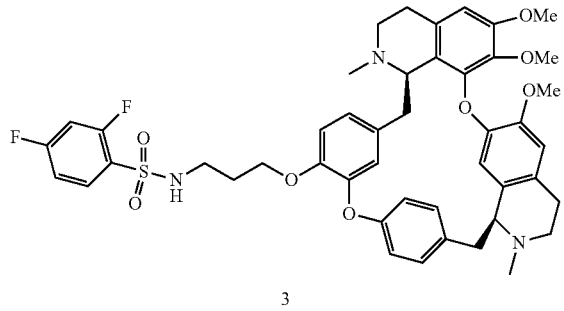

To a stirred solution of amine 1 (500 mg, 0.75 mmol) in 7 mL CH$_2$Cl$_2$ were added Et$_3$N (112 mg, 1.12 mmol, 1.5 equiv) and 2,4-difluorobenzenesulfonyl chloride (191 mg, 0.9 mmol, 1.2 equiv) at 0° C. The reaction was stirred at rt for 1 h and quenched with sat. NaHCO$_3$. The mixture was diluted with CH$_2$Cl$_2$ and washed with H$_2$O. The organic layer was dried and evaporated. The residue was purified with chromatograph to provide the product 3 (BBM-PA-3; 574 mg, 0.68 mmol, 91% yield). $^1$H NMR (400 MHz, CDCl$_3$) δ (ppm): 7.72-7.80 (m, 1H), 7.26 (dd, 1H, J=2.0 Hz, 8.0 Hz), 7.07 (dd, 1H, J=2.0 Hz, 8.0 Hz), 6.78-6.88 (m, 2H), 6.72-6.78 (m, 2H), 6.60 (dd, 1H, J=2.4 Hz, 8.0 Hz), 6.52 (s, 1H), 6.36-6.44 (b, 1H), 6.27 (s, 1H), 6.14-6.20 (m, 1H), 5.94-6.00 (b, 1H), 4.06-4.18 (m, 2H), 3.76-3.88 (m, 2H), 3.74 (s, 3H), 3.60 (s, 3H), 3.18-3.44 (m, 5H), 3.11 (s, 3H), 3.01 (d, 1H, J=14.0 Hz), 2.74-2.94 (m, 6H), 2.50-2.60 (m, 1H), 2.56 (s, 3H), 2.30-2.40 (m, 1H), 2.24 (s, 3H), 1.96-2.04 (m, 2H); MS C$_{46}$H$_{49}$F$_2$N$_3$O$_8$S [M+H]$^+$ calc'd: 842.33, found: 842.56

Example 2

The cell viability was measured by MTS assay. MTS reagent was bought from Abcam (ab 197010) and followed the protocol. A series of concentrations of Berbamine derivatives were plated into 96-well plate by series dilution. Each concentration has four replicates. Then H9 cells were plated into 96-well plate with a density of 5000/well. Cells were incubated with drugs for 24 hours in standard culture conditions. Then 20 µl/well MTS reagent was added into each well. After MTS adding, shake the plate briefly and incubate for 3 hours in standard culture conditions. The absorbance at OD=490 nm was measured by TECAN infinite M200 Pro plate reader at City of Hope. The dose-response data are analyzed by GraphPad Prism software packages. The IC50 was defined as the drug concentration that induced a 50% viability decrease.

TABLE 1

Figure 1B:
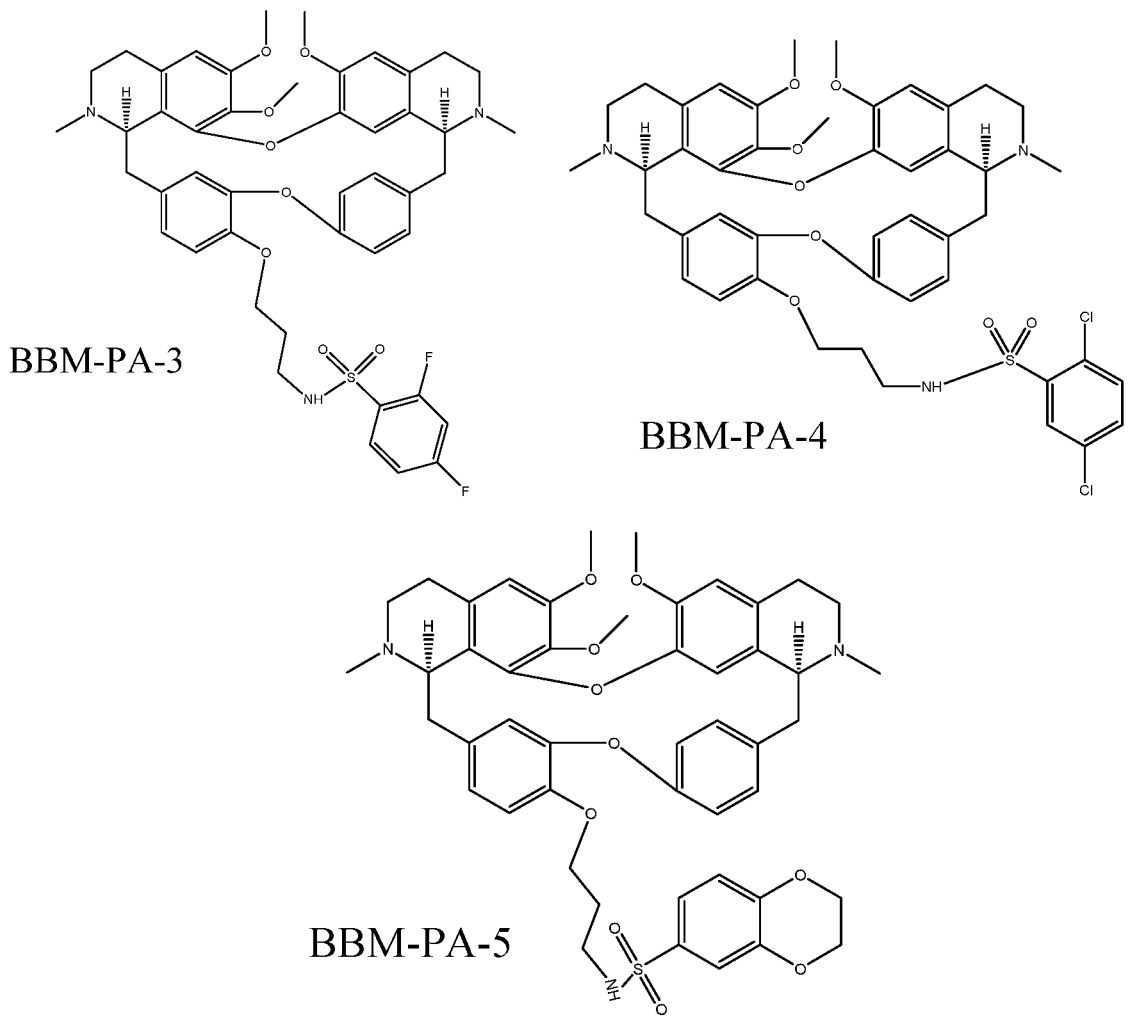
Figure 1C:
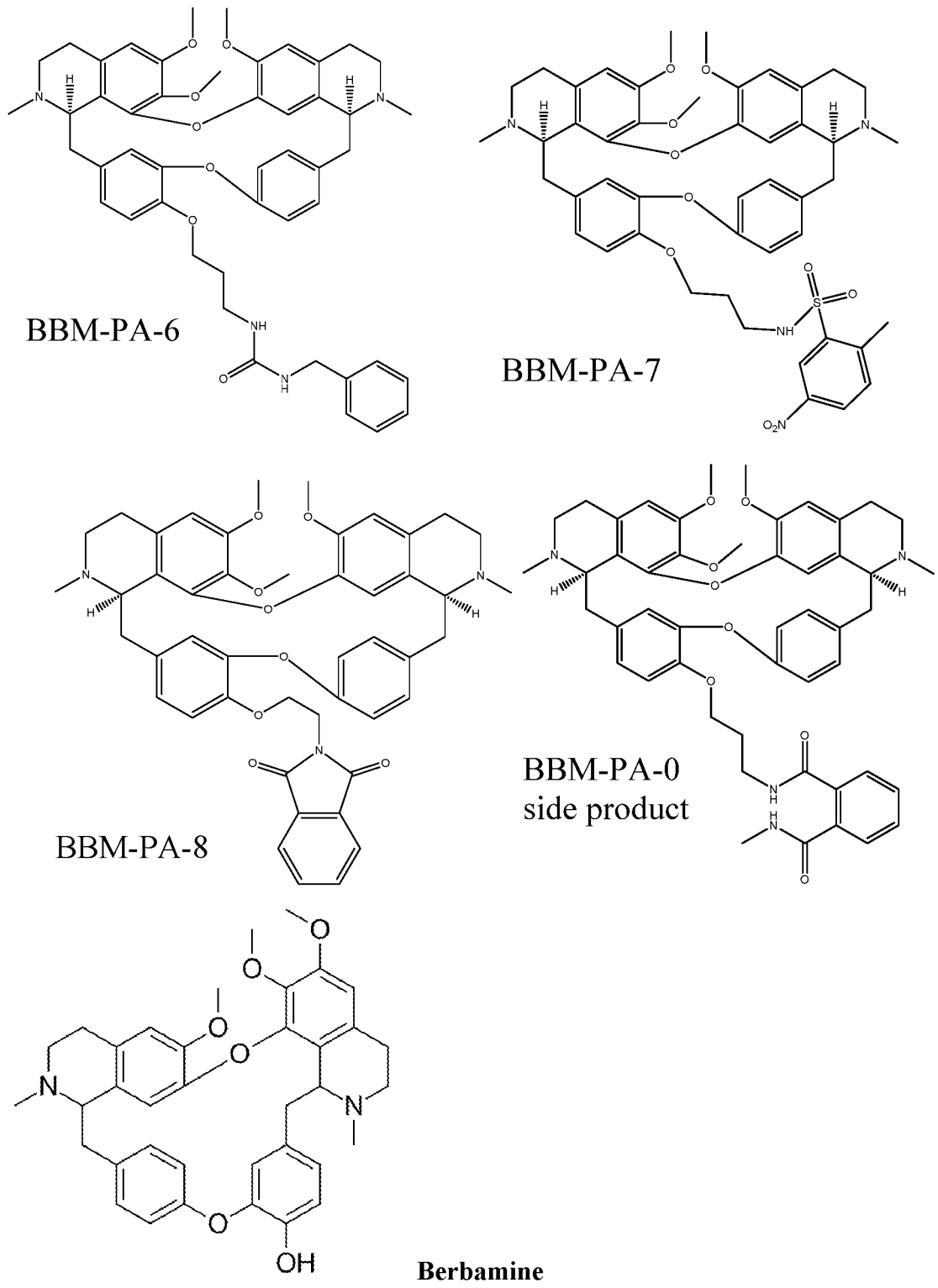

IC$_{50}$ for BBMD3 and new BBM derivatives (FIGS. 1A-1C)

| Compound | IC$_{50}$ (µM) |
|---|---|
| BBMD3 | 2.122078 |
| BBM-PA1 | 0.74115 |
| BBM-PA2 | 1.263003 |
| BBM-PA3 | 0.952185 |
| BBM-PA4 | 0.755429 |
| BBM-PA5 | 1.829833 |
| BBM-PA6 | 1.803583 |
| BBM-PA7 | 0.824738 |
| BBM-PA8 | 3.744766 |

Example 3

To determine the efficacy of the compounds in inhibiting cancer cell growth, BBM-PA4 ("PA4") was selected as an example to show its anti-cancer effect. Double-hit lymphoma (DHL) is an aggressive type of B-cell non-Hodgkin lymphoma (NHL) without effective treatment clinically. We selected DHL to test the effects of PA4 compared to berbamine ("BBM").

Figures 2A, 2B:
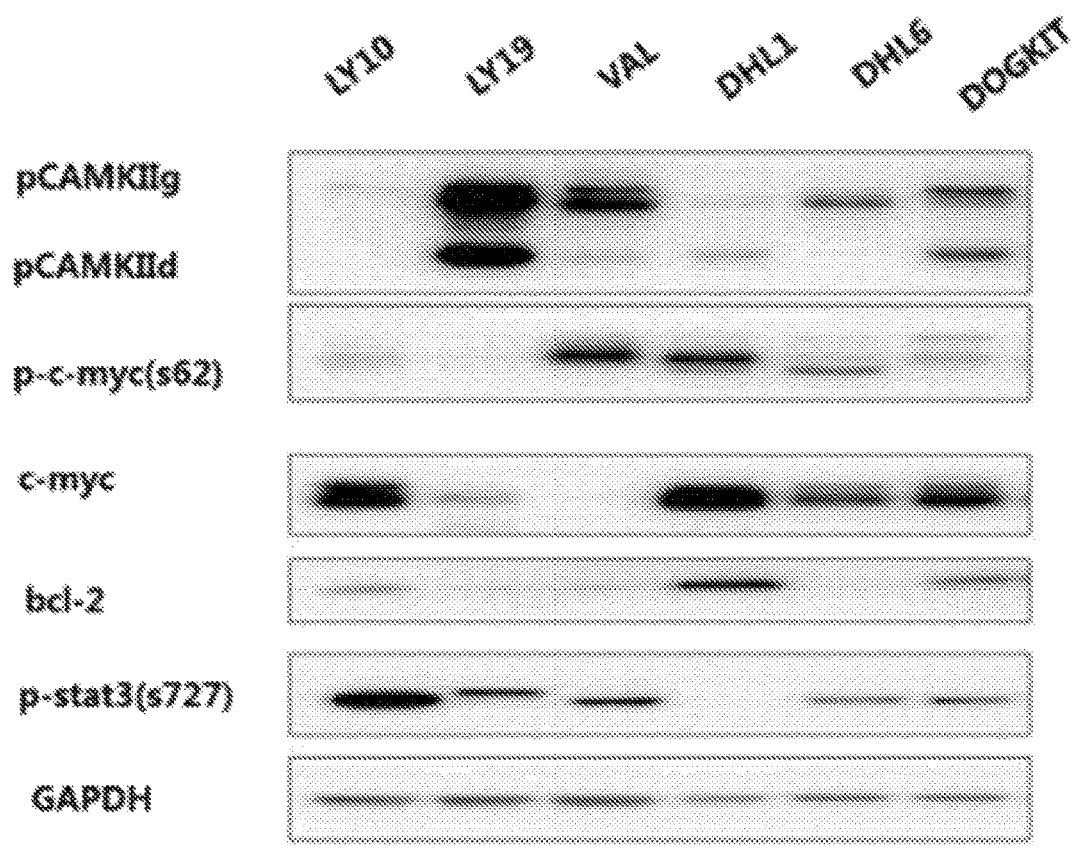
FIGS. 2A-2C show growth inhibitory effect of BBM-PA4 ("PA4") on five DHL cell lines in comparison to the effect of berbamine ("BBM").
Figure 2C:
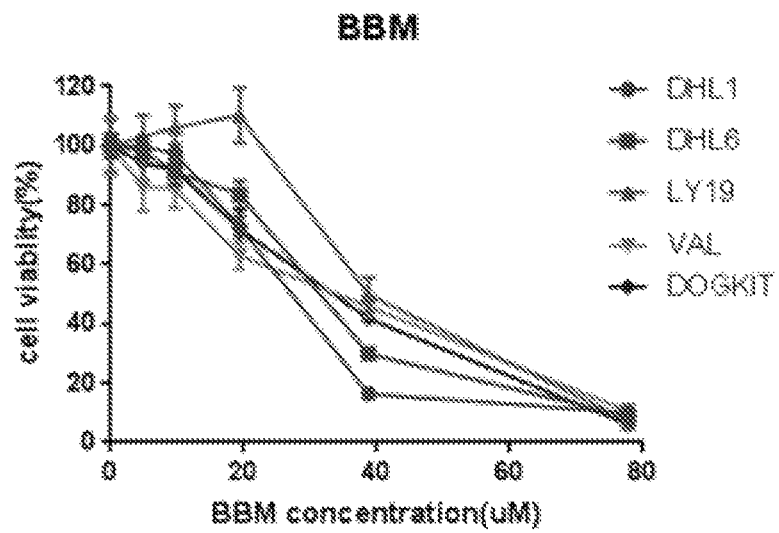
Figure 2D:
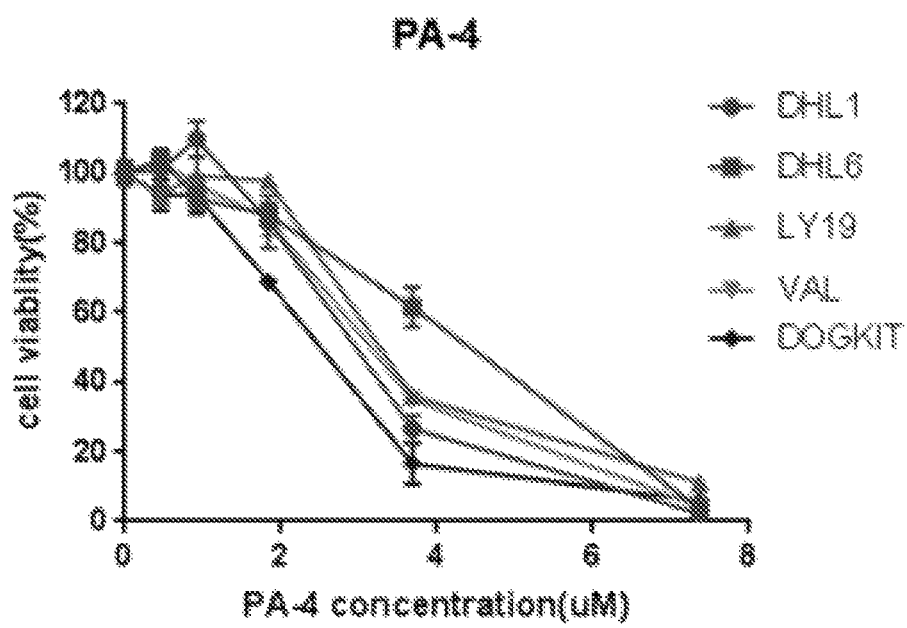

Five double-hit lymphoma (DHL) cell lines (NU-DHL-1, SU-DHL-6, LY19, DOGKIT and VAL. NU-DHL-1, SU-DHL-6 and LY19) were cultured in IMDM (Thermo Fisher Scientific, USA)+10% FBS (Omega Scientific, USA)+P/S. DOGKIT and VAL were cultured in RPMI 1640 (Thermo Fisher Scientific, USA)+10% FBS+P/S. All the cells were cultured at 37° C. in a 95% air, 5% CO2 humidified incubator. The expression levels of several proteins, including pCAMKIIg, p-c-Myc, Bcl-2 and Stat3 were measured as shown in FIG. 2A. The MTS assay, which measures cell viability and survival, was conducted with the CellTiter 96 Aqueous Cell Proliferation Kit (Promega, USA). 1-3×10$^5$ cells cultured in 96-well plate were treated with increasing concentration of BBM or PA4 for 24 hours. MTS was added to the culture 3 hours before detecting OD value. Incubate the plate at 37° C. for 3 hours in a humidified, 5% CO$_2$ atmosphere. The plate was read with a 96-well spectrometer using a 490 nm filter. The IC$_{50}$ was defined as the drug concentration that induced a 50% viability decrease normalized to vehicle control. The results showed lower IC$_{50}$ PA4 compared to BBM (FIG. 2B, table and FIGS. 2C-2D).

Figure 3A:
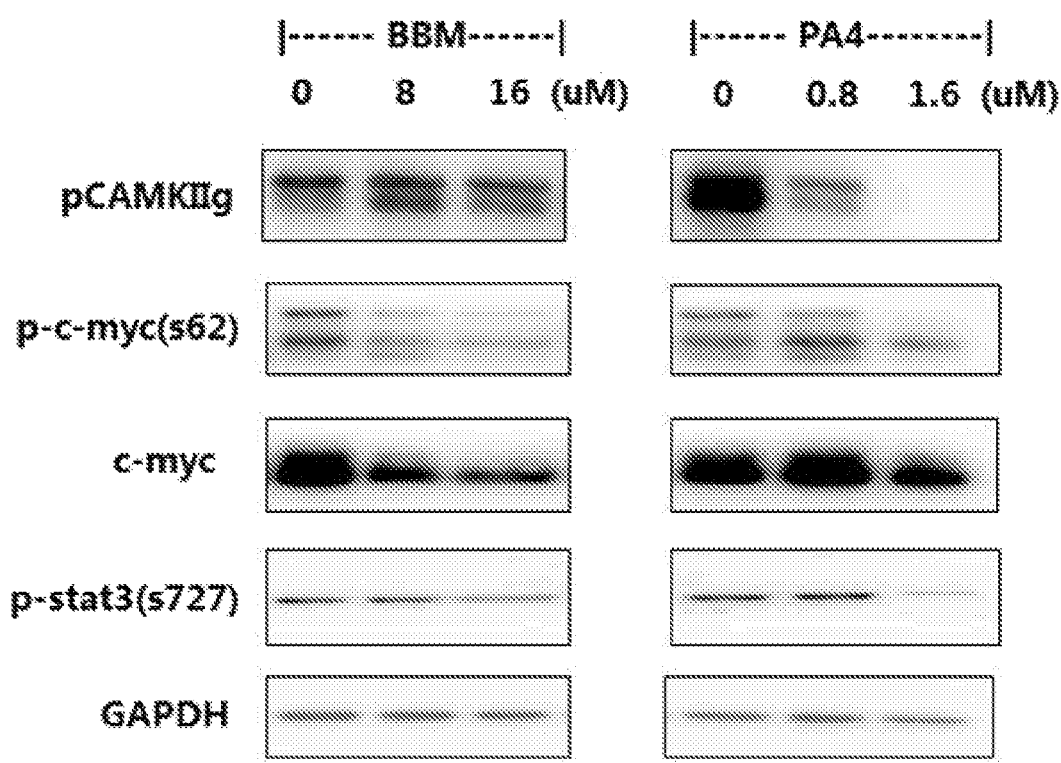
FIGS. 3A-3C show inhibitory effects of berbamine ("BBM") and BBM-PA4 ("PA4") on CAMKII and c-Myc axis. DOGKIT (FIG. 3A), DHL-6 (FIG. 3B) and VAL (FIG. 3C) cells were treated with BBM or PA4 at indicated concentrations for 24 h. Cell extract was subjected to western blotting using the antibodies as indicated. Protein levels of phosphorylated CAMKIIg (pCAMKIIg), Phosphorylated c-Myc, total c-Myc and phosphorylated STAT3 (s727) are decreased in a dose-dependent manner.
Figure 3B:
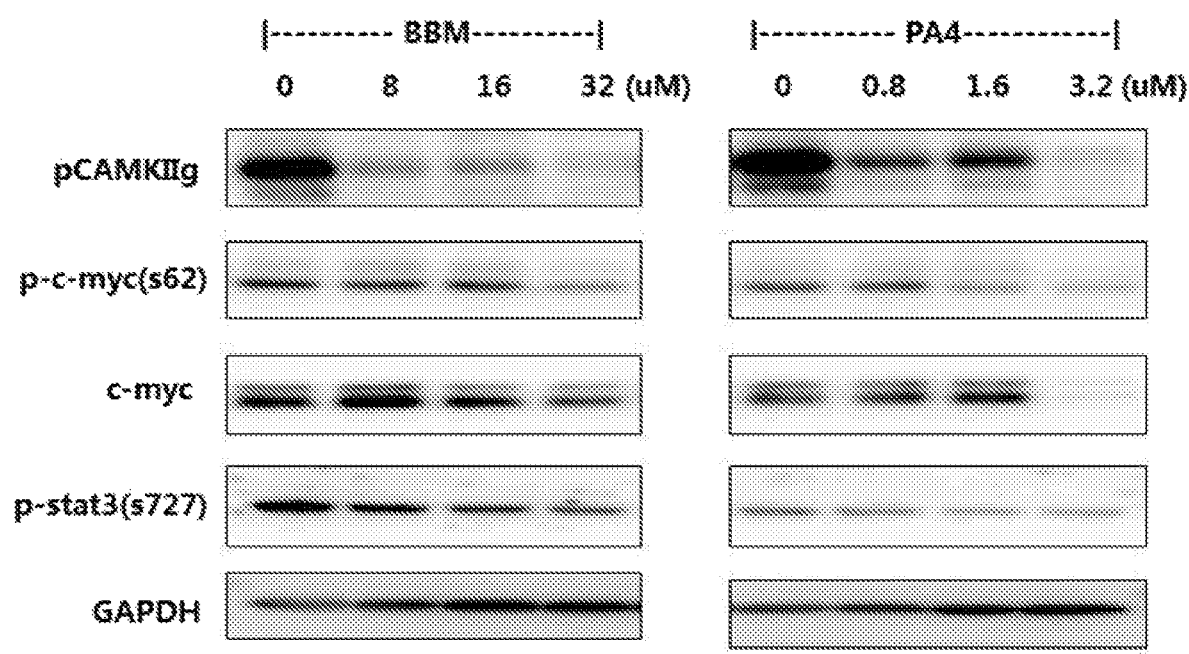
Figure 3C:
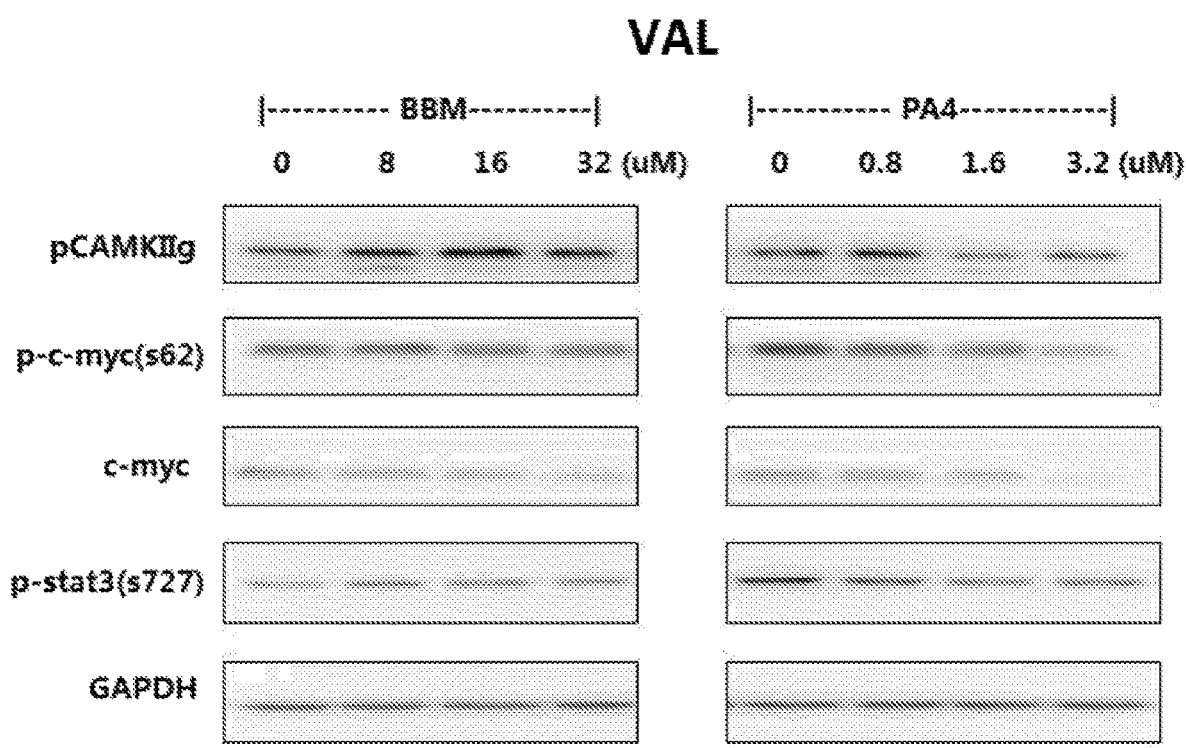

Total cellular protein was extracted using M-PER® Mammalian Protein Extraction Reagent (thermo fisher) or T-PER™ Tissue Protein Extraction Reagent with Protease/Phosphatase inhibitor cocktail. Extracts were loaded to sodium dodecyl sulfate-polyacrylamide gel electrophoresis (SDS-PAGE; 8% polyacrylamidegels); and then transferred to polyvinylidene difluoride (PVDF) membranes (Bio-Rad) and blocked with 5% nonfat milk (Bio-Rad) in TBS-Tween 20 (TBST). The membranes were incubated with primary antibodies overnight at 4° C. and a horseradish peroxidase-conjugated secondary antibody for 1 hr at room temperature. After reacting with ECL or Femto, the fluorescence was detected with Imager. The results showed that PA4 can be more potent than BBM to reduce pCAMKIIg and c-Myc (FIGS. 3A-3C).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed:

1. A compound having a formula:

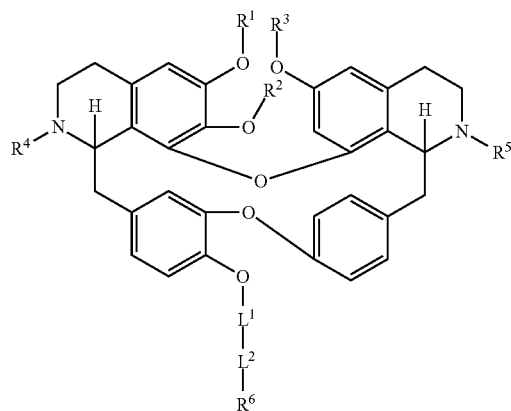

(I)

wherein:

Each $R^1$, $R^2$, $R^3$, $R^4$, and $R^5$ is independently hydrogen, or substituted or unsubstituted $C_1$-$C_{10}$ alkyl;

$L^1$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$L^2$ is —$NR^{2A}S(O)_2$— or —$S(O)_2NR^{2B}$—;

$R^6$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{2A}$ and $R^{2B}$ are independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

X is independently —F, —Cl, —Br or —I, or a salt thereof.

2. The compound of claim 1 having a formula:

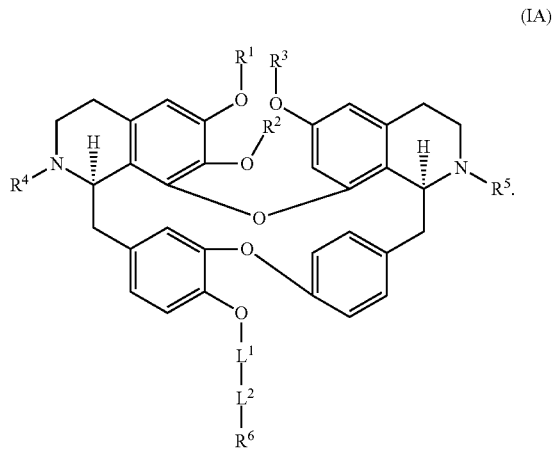

(IA)

3. The compound of claim 1, wherein $L^1$ is substituted or unsubstituted $C_1$-$C_{10}$ alkylene.

4. The compound of claim 1, wherein $L^1$ is unsubstituted $C_1$-$C_{10}$ alkylene.

5. The compound of claim 1, wherein $L^1$ is substituted or unsubstituted $C_1$-$C_5$ alkylene.

6. The compound of claim 1, wherein $L^1$ is unsubstituted $C_1$-$C_5$ alkylene.

7. The compound of claim 1, wherein each $R^{2A}$ and $R^{2B}$ is independently hydrogen or substituted or unsubstituted $C_1$-$C_5$ alkyl.

8. The compound of claim 1, wherein each $R^{2A}$ and $R^{2B}$ is independently hydrogen or unsubstituted $C_1$-$C_5$ alkyl.

9. The compound of claim 1, wherein $R^{2A}$ and $R^{2B}$ are hydrogen.

10. The compound of claim 1, wherein $L^2$ is —NHS(O)$_2$—.

11. The compound of claim 1, wherein the compound has a formula:

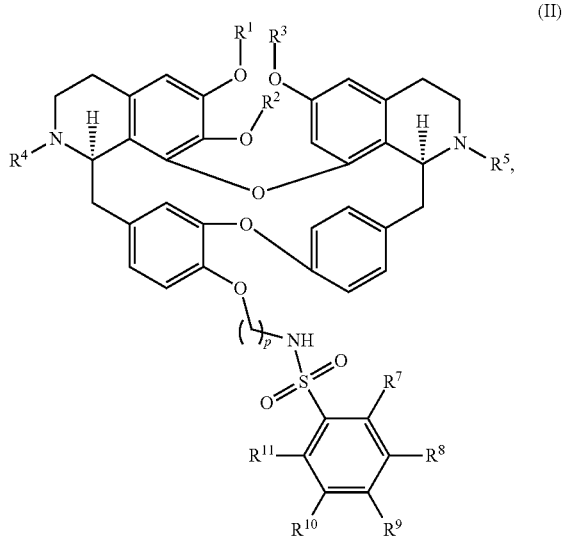

(II)

wherein:

$R^7$ is hydrogen, halogen, —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —$NHC(O)NR^{7A}R^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ and R$^8$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^8$ and R$^9$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^9$ and R$^{10}$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^{10}$ and R$^{11}$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{10C}$, R$^{10D}$, R$^{10A}$, R$^{10B}$, R$^{10C}$, R$^{10D}$, R$^{11A}$, R$^{11B}$, R$^{11C}$, and R$^{11D}$ are independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

n7, n8, n9, n10, and n11 are independently an integer from 0 to 4;

m7, m8, m9, m10, m11, v7, v8, v9, v10, and v11 are independently an integer from 1 to 2; and X$^7$, X$^8$, X$^9$, X$^{10}$, and X$^{11}$ are independently —F, —Cl, —Br or —I.

12. The compound of claim 1, wherein the compound has a formula:

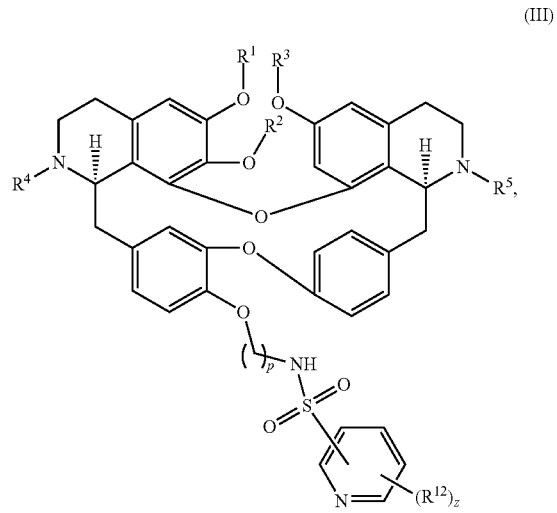

(III)

wherein:

R$^{12}$ is independently halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12A}$, R$^{12B}$, R$^{12C}$, and R$^{12D}$ are independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

z is an integer from 0 to 4;

n12 is independently an integer from 0 to 4;

m12 and v12 are independently an integer from 1 to 2; and

X$^{12}$ is independently —F, —Cl, —Br or —I.

13. The compound of claim 1, wherein the compound has a formula:

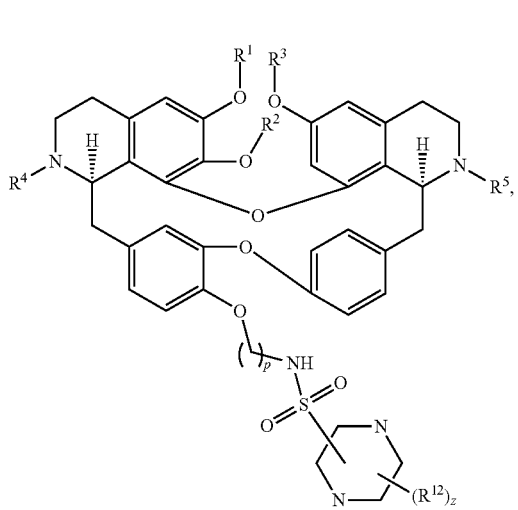

(IV)

wherein:

$R^{12}$ is independently halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12}C$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12A}$, $R^{12B}$, $R^{12C}$, and $R^{12D}$ are independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

p is an integer from 1 to 10;

z is an integer from 0 to 9;

n12 is independently an integer from 0 to 4;

m12 and v12 are independently an integer from 1 to 2; and $X^{12}$ is independently $-F$, $-Cl$, $-Br$ or $-I$.

14. The compound of claim 11, wherein each $R^1$, $R^2$, $R^3$, $R^4$, and $R^5$ is independently unsubstituted $C_1$-$C_{10}$ alkyl.

15. The compound of claim 11, wherein each $R^1$, $R^2$, $R^3$, $R^4$, and $R^5$ is independently unsubstituted $C_1$-$C_5$ alkyl.

16. The compound of claim 11, wherein each $R^1$, $R^2$, $R^3$, $R^4$, and $R^5$ are independently unsubstituted methyl.

17. The compound of claim 11, wherein p is an integer from 2 to 4.

18. The compound of claim 11, wherein p is 2 or 3.

19. The compound of claim 11, wherein each $R^7$, $R^8$, $R^9$, $R^{10}$, and $R^{11}$ is independently hydrogen, $-F$, $-Cl$, $-NO_2$ or unsubstituted methyl.

20. The compound of claim 11, wherein the compound has a formula

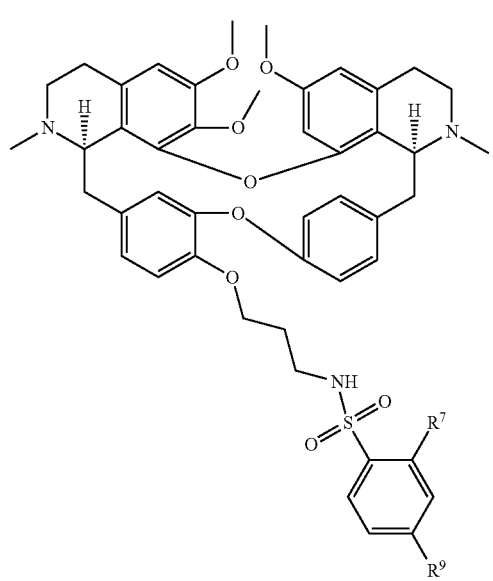

(V)

21. The compound of claim 20, wherein each $R^7$ and $R^9$ is independently hydrogen, $-F$ or $-NO_2$.

22. The compound of claim 11, wherein the compound has a formula:

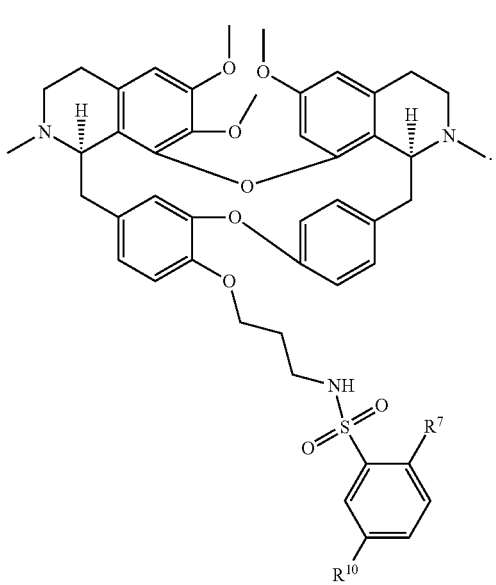

(VI)

23. The compound of claim 22, wherein each $R^7$ and $R^{10}$ is independently $-Cl$, $-NO_2$ or unsubstituted methyl.

24. The compound of claim 1, wherein the compound is
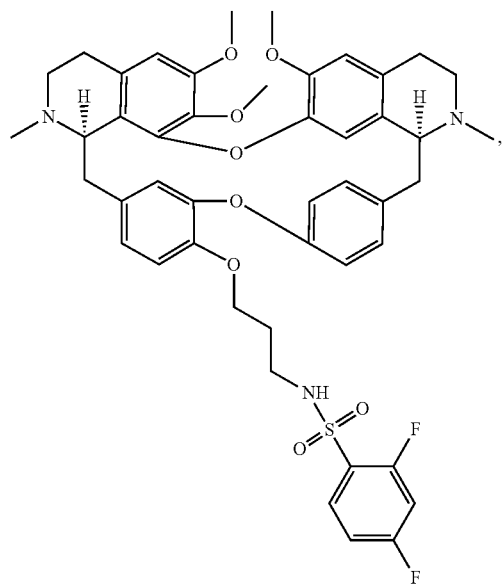
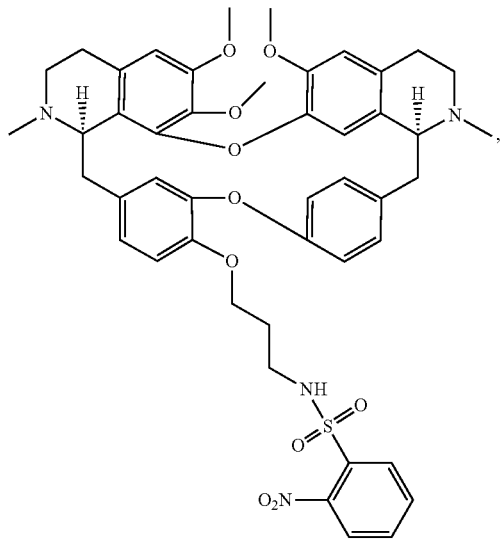
-continued
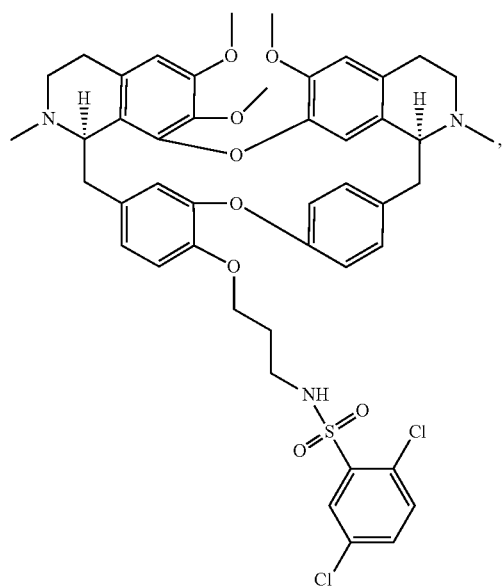
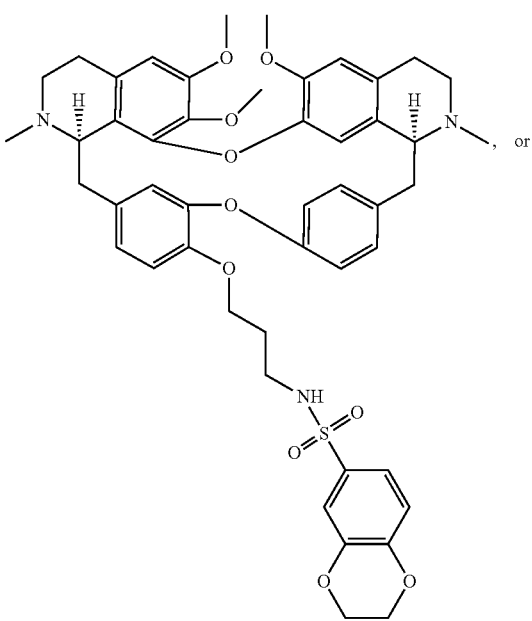
, or -continued

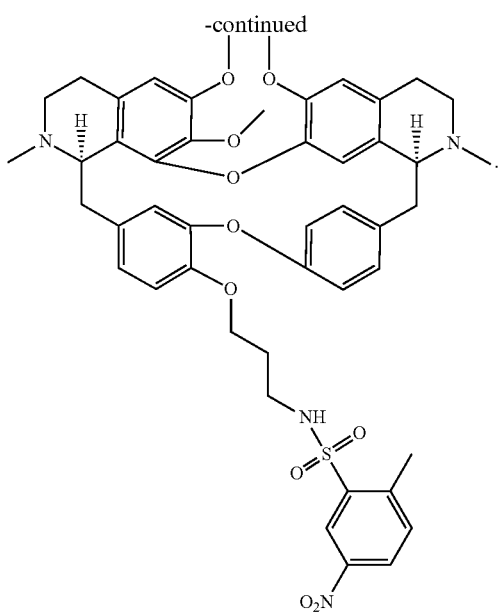

25. A pharmaceutical composition comprising a compound of claim 1, or a salt thereof, and a pharmaceutically acceptable carrier.

26. A method of treating a cancer comprising administering a therapeutically effective amount of a pharmaceutical composition of claim 25 to a subject in need thereof.

27. The method of claim 26, wherein the cancer is a Ca$^{2+}$/calmodulin-dependent protein kinase (CAMK) associated cancer.

28. The method of claim 26, wherein the cancer is a Ca$^{2+}$/calmodulin-dependent protein kinase II (CAMKIIγ) associated cancer.

29. The method of claim 26, wherein the cancer is benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia, acute lymphoblastic leukemia, acute lymphocytic leukemia, erythroleukemia, multiple myeloma, blood cancer, and lymphatic tissues cancer.

30. The method of claim 26, wherein the cancer is T-cell lymphoma.

31. A method of inhibiting a Ca$^{2+}$/calmodulin-dependent protein kinase (CAMK) in a cancer cell comprising contacting the cell with a compound of claim 1, or a salt thereof.

32. The method of claim 31, wherein the CAMK comprises Ca$^{2+}$/calmodulin-dependent protein kinase II (CAMKII).

33. The method of claim 31, wherein the CAMK comprises Ca$^{2+}$/calmodulin-dependent protein kinase II γ (CAMKIIγ).

34. The method of claim 31, wherein the cancer cell is a benign tumor cell, solid tumor cell, breast cancer cell, colon-rectal cancer cell, oral cancer cell, lung cancer cell, respiratory system cancers cell, melanoma cell, skin cancers cell, uterine cancer cell, pancreatic cancer cell, liver cancer cell, prostate cancer cell, cervical cancer cell, testicular cancer cell, genital cancer cell, bladder cancer cell, kidney cancer cell, urinary organs cancers cell, ovarian cancer cell, leukemia cancer cell, acute lymphoblastic leukemia cancer cell, acute lymphocytic leukemia cancer cell, erythroleukemia cancer cell, multiple myeloma cancer cell, blood cancer cell, or lymphatic tissues cancer cell.

35. The method of claim 31, wherein the cancer cell is T-cell lymphoma cancer cell.

36. A method of treating a cancer comprising administering a therapeutically effective amount of a compound of claim 1, or a salt thereof, to a subject in need thereof.

37. The method of claim 36, wherein the cancer is a Ca$^{2+}$/calmodulin-dependent protein kinase (CAMK) associated cancer.

38. The method of claim 36, wherein the cancer is a Ca$^{2+}$/calmodulin-dependent protein kinase II (CAMKII) associated cancer.

39. The method of claim 36, wherein the cancer is a Ca$^{2+}$/calmodulin-dependent protein kinase II γ (CAMKIIγ) associated cancer.

40. The method of claim 36, wherein the cancer is benign tumor, solid tumor, breast cancer, colon-rectal cancer, oral cancer, lung cancer, respiratory system cancers, melanoma, skin cancers, uterine cancer, pancreatic cancer, liver cancer, prostate cancer, cervical cancer, testicular cancer, genital cancer, bladder cancer, kidney cancer, urinary organs cancers, ovarian cancer, leukemia, acute lymphoblastic leukemia, acute lymphocytic leukemia, erythroleukemia, multiple myeloma, blood cancer, and lymphatic tissues cancer.

41. The method of claim 36, wherein the cancer is T-cell lymphoma.

* * * * *